US005622829A

United States Patent [19]
King et al.

[11] Patent Number: 5,622,829
[45] Date of Patent: Apr. 22, 1997

[54] GENETIC MARKERS FOR BREAST, OVARIAN, AND PROSTATIC CANCER

[75] Inventors: Mary-Claire King, Berkeley; Lori Friedman; Beth Ostermeyer, both of Albany; Sarah Rowell, Kensington; Eric Lynch, Albany; Csilla Szabo, Richmond; Ming Lee, Union City, all of Calif.

[73] Assignee: The Regents of the University of California, Oakland, Calif.

[21] Appl. No.: 425,061

[22] Filed: Apr. 19, 1995

Related U.S. Application Data

[63] Continuation of Ser. No. 326,983, Oct. 20, 1994, abandoned, which is a continuation of Ser. No. 232,535, Apr. 18, 1994, abandoned, which is a continuation of Ser. No. 163,959, Dec. 8, 1993, abandoned.

[51] Int. Cl.$^6$ .............................. C12Q 1/68; C12P 19/34; C07H 21/02; C07H 21/04
[52] U.S. Cl. .......................... 435/6; 435/91.2; 536/23.1; 536/24.3
[58] Field of Search .................. 536/23.1, 24.3–24.33; 435/6, 91.2

[56] References Cited

PUBLICATIONS

Hovig et al., "Searching Candidate Genes for Mutations", In Current Protocols in Human Genetics, published by Current Protocols, pp. 7.3.1–7.4.6 1994.
Gayther et al, Rapid Detection of Regionally Clustered Germ–Line BRCA 1 "Mutations by Multiplex Heteroduplex Analysis", Am. J. of Hum. Genet 58:451–456 1995.
Manak et al. in DNA Probes,, McMillan Publishers 1993, pp. 422–427 1993.
Zhang et al. Nar 19: 3929–3933, 1991.
Merajver et al. Nature Genetics 9: 439–443 1995.
Hosking et al. Nature Genetics 9: 343–344, 1995.
Futreal et al. Science 266: 120–122 1994.
Boyd, Nature Gentics 9: 335–336 1995.
Goldgar et al. J. of the Nat. Cancer Inst 86: 200–209 1994.
Simard, et al. Nature Genetics 8: 392–398 1994.
Castilla et al. Nature Genetics 8:387–391 1994.
Shattuck–Eidens JAMA 273: 535–541 1995.
Miki et al. Science 266: 6671 1994.
Neuhausen et al. Human Molecular Genetics 3: 1919–1926, 1994.
Barany, PNAS 88: 189–193, 1991.
Roberts, Science 259: 622–625 1993.
Goldberg et al. Clin Chem 39: 2360–2374 1993.

Primary Examiner—W. Gary Jones
Assistant Examiner—Dianne Rees
Attorney, Agent, or Firm—Richard Aron Osman, PhD

[57] ABSTRACT

Specific BRCA1 mutations, PCR primers and hybridization probes are used in nucleic acid-based methods for diagnostic of inheritable breast cancer susceptibility. Additionally, binding agents, such as antibodies, specific for peptides encoded by the subject BRCA1 mutants are used to identify expression products of diagnostic mutations/rare alleles in patient derived fluid or tissue samples. Compositions with high binding affinity for transcription or translation products of the disclosed BRCA1 mutations and alleles are used in therapeutic intervention. Such products include anti-sense nucleic acids, peptides encoded by the subject nucleic acids, and binding agents such as antibodies, specific for such peptides.

26 Claims, No Drawings

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 5656 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGCTCGCTGA  GACTTCCTGG  ACCCCGCACC  AGGCTGTGGG  GTTTCTCAGA  TAACTGGGCC      60

CCTGCGCTCA  GGAGGCCTTC  ACCCTCTGCT  CTGGGTAAAG  TTCATTGGAA  CAGAAAGAAA     120

TGGATTTATC  TGCTCTTCGC  GTTGAAGAAG  TACAAAATGT  CATTAATGCT  ATGCAGAAAA     180

TCTTAGAGTG  TCCCATCTGA  TTTTGCATGC  TGAAACTTCT  CAACCAGAAG  AAAGGGCCTT     240

CACAGTGTCC  TTTATGTAAG  AATGATATAA  CCAAAAGGAG  CCTACAAGAA  AGTACGAGAT     300

TTAGTCAACT  TGTTGAAGAG  CTATTGAAAA  TCATTTGTGC  TTTTCAGCTT  GACACAGGTT     360

TGGAGTATGC  AAACAGCTAT  AATTTTGCAA  AAAAGGAAAA  TAACTCTCCT  GAACATCTAA     420

AAGATGAAGT  TTCTATCATC  CAAAGTATGG  GCTACAGAAA  CCGTGCCAAA  AGACTTCTAC     480

AGAGTGAACC  CGAAAATCCT  TCCTTGCAGG  AAACCAGTCT  CAGTGTCCAA  CTCTCTAACC     540

TTGGAACTGT  GAGAACTCTG  AGGACAAAGC  AGCGGATACA  ACCTCAAAAG  ACGTCTGTCT     600

ACATTGAATT  GGGATCTGAT  TCTTCTGAAG  ATACCGTTAA  TAAGGCAACT  TATTGCAGTG     660
```

```
TGGGAGATCA AGAATTGTTA CAAATCACCC CTCAAGGAAC CAGGGATGAA ATCAGTTTGG      720

ATTCTGCAAA AAAGGCTGCT TGTGAATTTT CTGAGACGGA TGTAACAAAT ACTGAACATC      780

ATCAACCCAG TAATAATGAT TTGAACACCA CTGAGAAGCG TGCAGCTGAG AGGCATCCAG      840

AAAAGTATCA GGGTAGTTCT GTTTCAAACT TGCATGTGGA GCCATGTGGC ACAAATACTC      900

ATGCCAGCTC ATTACAGCAT GAGAACAGCA GTTTATTACT CACTAAAGAC AGAATGAATG      960

TAGAAAAGGC TGAATTCTGT AATAAAAGCA AACAGCCTGG CTTAGCAAGG AGCCAACATA     1020

ACAGATGGGC TGGAAGTAAG GAAACATGTA ATGATAGGCG GACTCCCAGC ACAGAAAAAA     1080

AGGTAGATCT GAATGCTGAT CCCCTGTGTG AGAGAAAAGA ATGGAATAAG CAGAAACTGC     1140

CATGCTCAGA GAATCCTAGA GATACTGAAG ATGTTCCTTG GATAACACTA AATAGCAGCA     1200

TTCAGAAAGT TAATGAGTGG TTTTCCAGAA GTGATGAACT GTTAGGTTCT GATGACTCAC     1260

ATGATGGGGA GTCTGAATCA AATGCCAAAG TAGCTGATGT ATTGGACGTT CTAAATGAGG     1320

TAGATGAATA TTCTGGTTCT TCAGAGAAAA TAGACTTACT GGCCAGTGAT CCTCATGAGG     1380

CTTTAATATG TAAAAGTGAA AGAGTTCACT CCAAATCAGT AGAGAGTAAT ATTGAAGACA     1440

AAATATTTGG GAAAACCTAT CGGAAGAAGG CAAGCCTCCC CAACTTAAGC CATGTAACTG     1500

AAAATCTAAT TATAGGAGCA TTTGTTACTG AGCCACAGAT AATACAAGAG CGTCCCCTCA     1560

CAAATAAATT AAAGCGTAAA AGGAGACCTA CATCAGGCCT TCATCCTGAG GATTTTATCA     1620

AGAAAGCAGA TTTGGCAGTT CAAAAGACTC CTGAAATGAT AAATCAGGGA ACTAACCAAA     1680

CGGAGCAGAA TGGTCAAGTG ATGAATATTA CTAATAGTGG TCATGAGAAT AAAACAAAAG     1740

GTGATTCTAT TCAGAATGAG AAAAATCCTA ACCCAATAGA ATCACTCGAA AAGAATCTG      1800

CTTTCAAAAC GAAAGCTGAA CCTATAAGCA GCAGTATAAG CAATATGGAA CTCGAATTAA     1860

ATATCCACAA TTCAAAAGCA CCTAAAAAGA ATAGGCTGAG GAGGAAGTCT TCTACCAGGC     1920

ATATTCATGC GCTTGAACTA GTAGTCAGTA GAAATCTAAG CCCACCTAAT TGTACTGAAT     1980

TGCAAATTGA TAGTTGTTCT AGCAGTGAAG AGATAAAGAA AAAAAAGTAC AACCAAATGC     2040

CAGTCAGGCA CAGCAGAAAC CTACAACTCA TGGAAGGTAA AGAACCTGCA ACTGGAGCCA     2100

AGAAGAGTAA CAAGCCAAAT GAACAGACAA GTAAAAGACA TGACAGCGAT ACTTTCCCAG     2160

AGCTGAAGTT AACAAATGCA CCTGGTTCTT TTACTAAGTG TTCAAATACC AGTGAACTTA     2220

AAGAATTTGT CAATCCTAGC CTTCCAAGAG AAGAAAAAGA AGAGAAACTA GAAACAGTTA     2280

AAGTGTCTAA TAATGCTGAA GACCCCAAAG ATCTCATGTT AAGTGGAGAA AGGGTTTTGC     2340

AAACTGAAAG ATCTGTAGAG AGTAGCAGTA TTTCATTGGT ACCTGGTACT GATTATGGCA     2400

CTCAGGAAAG TATCTCGTTA CTGGAAGTTA GCACTCTAGG GAAGGCAAAA ACAGAACCAA     2460

ATAAATGTGT GAGTCAGTGT GCAGCATTTG AAAACCCCAA GGGACTAATT CATGGTTGTT     2520

CCAAAGATAA TAGAAATGAC ACAGAAGGCT TTAAGTATCC ATTGGGACAT GAAGTTAACC     2580

ACAGTCGGGA AACAAGCATA GAAATGGAAG AAAGTGAACT TGATGCTCAG TATTTGCAGA     2640

ATACATTCAA GGTTTCAAAG CGCCAGTCAT TTGCTCCGTT TTCAAATCCA GGAAATGCAG     2700

AAGAGGAATG TGCAACATTC TCTGCCCACT CTGGGTCCTT AAAGAAACAA AGTCCAAAAG     2760

TCACTTTTGA ATGTGAACAA AAGGAAGAAA ATCAAGGAAA GAATGAGTCT AATATCAAGC     2820

CTGTACAGAC AGTTAATATC ACTGCAGGCT TTCCTGTGGT TGGTCAGAAA GATAAGCCAG     2880

TTGATAATGC CAAATGTAGT ATCAAAGGAG GCTCTAGGTT TTGTCTATCA TCTCAGTTCA     2940

GAGGCAACGA AACTGGACTC ATTACTCCAA ATAAACATGG ACTTTTACAA AACCCATATC     3000

GTATACCACC ACTTTTTCCC ATCAAGTCAT TTGTTAAAAC TAAATGTAAG AAAAATCTGC     3060
```

```
TAGAGGAAAA  CTTTGAGGAA  CATTCAATGT  CACCTGAAAG  AGAAATGGGA  AATGAGAACA   3120
TTCCAAGTAC  AGTGAGCACA  ATTAGCCGTA  ATAACATTAG  AGAAATGTT   TTTAAAGAAG   3180
CCAGCTCAAG  CAATATTAAT  GAAGTAGGTT  CCAGTACTAA  TGAAGTGGGC  TCCAGTATTA   3240
ATGAAATAGG  TTCCAGTGAT  GAAAACATTC  AAGCAGAACT  AGGTAGAAAC  AGAGGGCCAA   3300
AATTGAATGC  TATGCTTAGA  TTAGGGGTTT  TGCAACCTGA  GGTCTATAAA  CAAAGTCTTC   3360
CTGGAAGTAA  TTGTAAGCAT  CCTGAAATAA  AAAAGCAAGA  ATATGAAGAA  GTAGTTCAGA   3420
CTGTTAATAC  AGATTTCTCT  CCATATCTGA  TTTCAGATAA  CTTAGAACAG  CCTATGGGAA   3480
GTAGTCATGC  ATCTCAGGTT  TGTTCTGAGA  CACCTGATGA  CCTGTTAGAT  GATGGTGAAA   3540
TAAAGGAAGA  TACTAGTTTT  GCTGAAAATG  ACATTAAGGA  AAGTTCTGCT  GTTTTTAGCA   3600
AAAGCGTCCA  GAAAGGAGAG  CTTAGCAGGA  GTCCTAGCCC  TTTCACCCAT  ACACATTTGG   3660
CTCAGGGTTA  CCGAAGAGGG  GCCAAGAAAT  TAGAGTCCTC  AGAAGAGAAC  TTATCTAGTG   3720
AGGATGAAGA  GCTTCCCTGC  TTCCAACACT  TGTTATTTGG  TAAAGTAAAC  AATATACCTT   3780
CTCAGTCTAC  TAGGCATAGC  ACCGTTGCTA  CCGAGTGTCT  GTCTAAGAAC  ACAGAGGAGA   3840
ATTATTATC   ATTGAAGAAT  AGCTTAAATG  ACTGCAGTAA  CCAGGTAATA  TTGGCAAAGG   3900
CATCTCAGGA  ACATCACCTT  AGTGAGGAAA  CAAAATGTTC  TGCTAGCTTG  TTTTCTTCAC   3960
AGTGCAGTGA  ATTGGAAGAC  TTGACTGCAA  ATACAAACAC  CAGGATCCT   TTCTTGATTG   4020
GTTCTTCCAA  ACAAATGAGG  CATCAGTCTG  AAAGCCAGGG  AGTTGGTCTG  AGTGACAAGG   4080
AATTGGTTTC  AGATGATGAA  GAAAGAGGAA  CGGGCTTGGA  AGAAAATAAT  CAAGAAGAGC   4140
AAAGCATGGA  TTCAAACTTA  GGTGAAGCAG  CATCTGGGTG  TGAGAGTGAA  ACAAGCGTCT   4200
CTGAAGACTG  CTCAGGGCTA  TCCTCTCAGA  GTGACATTTT  AACCACTCAG  CAGAGGGATA   4260
CCATGCAACA  TAACCTGATA  AAGCTCCAGC  AGGAAATGGC  TGAACTAGAA  GCTGTGTTAG   4320
AACAGCATGG  GAGCCAGCCT  TCTAACAGCT  ACCCTTCCAT  CATAAGTGAC  TCTTCTGCCC   4380
TTGAGGACCT  GCGAAATCCA  GAACAAAGCA  CATCAGAAAA  AGCAGTATTA  ACTTCACAGA   4440
AAAGTAGTGA  ATACCCTATA  AGCCAGAATC  CAGAAGGCCT  TTCTGCTGAC  AAGTTTGAGG   4500
TGTCTGCAGA  TAGTTCTACC  AGTAAAAATA  AAGAACCAGG  AGTGGAAAGG  TCATCCCCTT   4560
CTAAATGCCC  ATCATTAGAT  GATAGGTGGT  ACATGCACAG  TTGCTCTGGG  AGTCTTCAGA   4620
ATAGAAACTA  CCCATCTCAA  GAGGAGCTCA  TTAAGGTTGT  TGATGTGGAG  GAGCAACAGC   4680
TGGAAGAGTC  TGGGCCACAC  GATTTGACGG  AAACATCTTA  CTTGCCAAGG  CAAGATCTAG   4740
AGGGAACCCC  TTACCTGGAA  TCTGGAATCA  GCCTCTTCTC  TGATGACCCT  GAATCTGATC   4800
CTTCTGAAGA  CAGAGCCCCA  GAGTCAGCTC  GTGTTGGCAA  CATACCATCT  TCAACCTCTG   4860
CATTGAAAGT  TCCCCAATTG  AAAGTTGCAG  AATCTGCCCA  GAGTCCAGCT  GCTGCTCATA   4920
CTACTGATAC  TGCTGGGTAT  AATGCAATGG  AAGAAAGTGT  GAGCAGGGAG  AAGCCAGAAT   4980
TGACAGCTTC  AACAGAAAGG  GTCAACAAAA  GAATGTCCAT  GGTGGTGTCT  GGCCTGACCC   5040
CAGAAGAATT  TATGCTCGTG  TACAAGTTTG  CCAGAAAACA  CCACATCACT  TTAACTAATC   5100
TAATTACTGA  AGAGACTACT  CATGTTGTTA  TGAAAACAGA  TGCTGAGTTT  GTGTGTGAAC   5160
GGACACTGAA  ATATTTTCTA  GGAATTGCGG  GAGGAAAATG  GGTAGTTAGC  TATTTCTGGG   5220
TGACCCAGTC  TATTAAAGAA  AGAAAAATGC  TGAATGAGCA  TGATTTTGAA  GTCAGAGGAG   5280
ATGTGGTCAA  TGGAAGAAAC  CACCAAGGTC  CAAAGCGAGC  AAGAGAATCC  CAGGACAGAA   5340
AGATCTTCAG  GGGGCTAGAA  ATCTGTTGCT  ATGGGCCCTT  CACCAACATG  CCCACAGATC   5400
AACTGGAATG  GATGGTACAG  CTGTGTGGTG  CTTCTGTGGT  GAAGGAGCTT  TCATCATTCA   5460
```

-continued

| | | | | | |
|---|---|---|---|---|---|
| CCCTTGGCAC | AGGTGTCCAC | CCAATTGTGG | TTGTGCAGCC | AGATGCCTGG | ACAGAGGACA | 5520 |
| ATGGCTTCCA | TGCAATTGGG | CAGATGTGTG | AGGCACCTGT | GGTGACCCGA | GAGTGGGTGT | 5580 |
| TGGACAGTGT | AGCACTCTAC | CAGTGCCAGG | AGCTGGACAC | CTACCTGATA | CCCCAGATCC | 5640 |
| CCCACAGCCA | CTACTG | | | | | 5656 |

(2) INFORMATION FOR SEQ ID NO:2:

(i) SEQUENCE CHARACTERISTICS:
        (A) LENGTH: 5709 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | GTGTGACCAC | 240 |
| ATATTTTGCA | AATTTTGCAT | GCTGAAACTT | CTCAACCAGA | AGAAAGGGCC | TTCACAGTGT | 300 |
| CCTTTATGTA | AGAATGATAT | AACCAAAAGG | AGCCTACAAG | AAAGTACGAG | ATTTAGTCAA | 360 |
| CTTGTTGAAG | AGCTATTGAA | AATCATTTGT | GCTTTTCAGC | TTGACACAGG | TTTGGAGTAT | 420 |
| GCAAACAGCT | ATAATTTTGC | AAAAAAGGAA | AATAACTCTC | CTGAACATCT | AAAAGATGAA | 480 |
| GTTTCTATCA | TCCAAAGTAT | GGGCTACAGA | AACCGTGCCA | AAAGACTTCT | ACAGAGTGAA | 540 |
| CCCGAAAATC | CTTCCTTGCA | GGAAACCAGT | CTCAGTGTCC | AACTCTCTAA | CCTTGGAACT | 600 |
| GTGAGAACTC | TGAGGACAAA | GCAGCGGATA | CAACCTCAAA | AGACGTCTGT | CTACATTGAA | 660 |
| TTGGGATCTG | ATTCTTCTGA | AGATACCGTT | AATAAGGCAA | CTTATTGCAG | TGTGGGAGAT | 720 |
| CAAGAATTGT | TACAAATCAC | CCCTCAAGGA | ACCAGGGATG | AAATCAGTTT | GGATTCTGCA | 780 |
| AAAAAGGCTG | CTTGTGAATT | TTCTGAGACG | GATGTAACAA | ATACTGAACA | TCATCAACCC | 840 |
| AGTAATAATG | ATTTGAACAC | CACTGAGAAG | CGTGCAGCTG | AGAGGCATCC | AGAAAAGTAT | 900 |
| CAGGGTAGTT | CTGTTTCAAA | CTTGCATGTG | GAGCCATGTG | GCACAAATAC | TCATGCCAGC | 960 |
| TCATTACAGC | ATGAGAACAG | CAGTTTATTA | CTCACTAAAG | ACAGAATGAA | TGTAGAAAAG | 1020 |
| GCTGAATTCT | GTAATAAAAG | CAAACAGCCT | GGCTTAGCAA | GGAGCCAACA | TAACAGATGG | 1080 |
| GCTGGAAGTA | AGGAAACATG | TAATGATAGG | CGGACTCCCA | GCACAGAAAA | AAAGGTAGAT | 1140 |
| CTGAATGCTG | ATCCCCTGTG | TGAGAGAAAA | GAATGGAATA | AGCAGAAACT | GCCATGCTCA | 1200 |
| GAGAATCCTA | GAGATACTGA | AGATGTTCCT | TGGATAACAC | TAAATAGCAG | CATTCAGAAA | 1260 |
| GTTAATGAGT | GGTTTTCCAG | AAGTGATGAA | CTGTTAGGTT | CTGATGACTC | ACATGATGGG | 1320 |
| GAGTCTGAAT | CAAATGCCAA | AGTAGCTGAT | GTATTGGACG | TTCTAAATGA | GGTAGATGAA | 1380 |
| TATTCTGGTT | CTTCAGAGAA | AATAGACTTA | CTGGCCAGTG | ATCCTCATGA | GGCTTTAATA | 1440 |
| TGTAAAAGTG | AAAGAGTTCA | CTCCAAATCA | GTAGAGAGTA | ATATTGAAGA | CAAAATATTT | 1500 |
| GGGAAAACCT | ATCGGAAGAA | GGCAAGCCTC | CCCAACTTAA | GCCATGTAAC | TGAAAATCTA | 1560 |
| ATTATAGGAG | CATTTGTTAC | TGAGCCACAG | ATAATACAAG | AGCGTCCCCT | CACAAATAAA | 1620 |
| TTAAAGCGTA | AAAGGAGACC | TACATCAGGC | CTTCATCCTG | AGGATTTTAT | CAAGAAAGCA | 1680 |
| GATTTGGCAG | TTCAAAAGAC | TCCTGAAATG | ATAAATCAGG | GAACTAACCA | AACGGAGCAG | 1740 |

| | | | | | | |
|---|---|---|---|---|---|---|
|AATGGTCAAG|TGATGAATAT|TACTAATAGT|GGTCATGAGA|ATAAAACAAA|AGGTGATTCT|1800|
|ATTCAGAATG|AGAAAAATCC|TAACCCAATA|GAATCACTCG|AAAAGAATC|TGCTTTCAAA|1860|
|ACGAAAGCTG|AACCTATAAG|CAGCAGTATA|AGCAATATGG|AACTCGAATT|AAATATCCAC|1920|
|AATTCAAAAG|CACCTAAAAA|GAATAGGCTG|AGGAGGAAGT|CTTCTACCAG|GCATATTCAT|1980|
|GCGCTTGAAC|TAGTAGTCAG|TAGAAATCTA|AGCCCACCTA|ATTGTACTGA|ATTGCAAATT|2040|
|GATAGTTGTT|CTAGCAGTGA|AGAGATAAAG|AAAAAAAGT|ACAACCAAAT|GCCAGTCAGG|2100|
|CACAGCAGAA|ACCTACAACT|CATGGAAGGT|AAAGAACCTG|CAACTGGAGC|CAAGAAGAGT|2160|
|AACAAGCCAA|ATGAACAGAC|AAGTAAAAGA|CATGACAGCG|ATACTTTCCC|AGAGCTGAAG|2220|
|TTAACAAATG|CACCTGGTTC|TTTTACTAAG|TGTTCAAATA|CCAGTGAACT|TAAAGAATTT|2280|
|GTCAATCCTA|GCCTTCCAAG|AGAAGAAAAA|GAAGAGAAAC|TAGAAACAGT|TAAAGTGTCT|2340|
|AATAATGCTG|AAGACCCCAA|AGATCTCATG|TTAAGTGGAG|AAAGGGTTTT|GCAAACTGAA|2400|
|AGATCTGTAG|AGAGTAGCAG|TATTTCATTG|GTACCTGGTA|CTGATTATGG|CACTCAGGAA|2460|
|AGTATCTCGT|TACTGGAAGT|TAGCACTCTA|GGGAAGGCAA|AAACAGAACC|AAATAAATGT|2520|
|GTGAGTCAGT|GTGCAGCATT|TGAAAACCCC|AAGGGACTAA|TTCATGGTTG|TTCCAAAGAT|2580|
|AATAGAAATG|ACACAGAAGG|CTTTAAGTAT|CCATTGGGAC|ATGAAGTTAA|CCACAGTCGG|2640|
|GAAACAAGCA|TAGAAATGGA|AGAAAGTGAA|CTTGATGCTC|AGTATTTGCA|GAATACATTC|2700|
|AAGGTTTCAA|AGCGCCAGTC|ATTTGCTCCG|TTTTCAAATC|CAGGAAATGC|AGAAGAGGAA|2760|
|TGTGCAACAT|TCTCTGCCCA|CTCTGGGTCC|TTAAAGAAAC|AAAGTCCAAA|AGTCACTTTT|2820|
|GAATGTGAAC|AAAAGGAAGA|AAATCAAGGA|AAGAATGAGT|CTAATATCAA|GCCTGTACAG|2880|
|ACAGTTAATA|TCACTGCAGG|CTTTCCTGTG|GTTGGTCAGA|AAGATAAGCC|AGTTGATAAT|2940|
|GCCAAATGTA|GTATCAAAGG|AGGCTCTAGG|TTTTGTCTAT|CATCTCAGTT|CAGAGGCAAC|3000|
|GAAACTGGAC|TCATTACTCC|AAATAAACAT|GGACTTTTAC|AAAACCCATA|TCGTATACCA|3060|
|CCACTTTTTC|CCATCAAGTC|ATTTGTTAAA|ACTAAATGTA|AGAAAATCT|GCTAGAGGAA|3120|
|AACTTTGAGG|AACATTCAAT|GTCACCTGAA|AGAGAAATGG|GAAATGAGAA|CATTCCAAGT|3180|
|ACAGTGAGCA|CAATTAGCCG|TAATAACATT|AGAGAAAATG|TTTTTAAAGA|AGCCAGCTCA|3240|
|AGCAATATTA|ATGAAGTAGG|TTCCAGTACT|AATGAAGTGG|GCTCCAGTAT|TAATGAAATA|3300|
|GGTTCCAGTG|ATGAAAACAT|TCAAGCAGAA|CTAGGTAGAA|ACAGAGGGCC|AAAATTGAAT|3360|
|GCTATGCTTA|GATTAGGGGT|TTTGCAACCT|GAGGTCTATA|AACAAAGTCT|TCCTGGAAGT|3420|
|AATTGTAAGC|ATCCTGAAAT|AAAAAAGCAA|GAATATGAAG|AAGTAGTTCA|GACTGTTAAT|3480|
|ACAGATTTCT|CTCCATATCT|GATTTCAGAT|AACTTAGAAC|AGCCTATGGG|AAGTAGTCAT|3540|
|GCATCTCAGG|TTTGTTCTGA|GACACCTGAT|GACCTGTTAG|ATGATGGTGA|AATAAAGGAA|3600|
|GATACTAGTT|TTGCTGAAAA|TGACATTAAG|GAAAGTTCTG|CTGTTTTTAG|CAAAAGCGTC|3660|
|CAGAAAGGAG|AGCTTAGCAG|GAGTCCTAGC|CCTTTCACCC|ATACACATTT|GGCTCAGGGT|3720|
|TACCGAAGAG|GGGCCAAGAA|ATTAGAGTCC|TCAGAAGAGA|ACTTATCTAG|TGAGGATGAA|3780|
|GAGCTTCCCT|GCTTCCAACA|CTTGTTATTT|GGTAAAGTAA|ACAATATACC|TTCTCAGTCT|3840|
|ACTAGGCATA|GCACCGTTGC|TACCGAGTGT|CTGTCTAAGA|ACACAGAGGA|GAATTTATTA|3900|
|TCATTGAAGA|ATAGCTTAAA|TGACTGCAGT|AACCAGGTAA|TATTGGCAAA|GGCATCTCAG|3960|
|GAACATCACC|TTAGTGAGGA|AACAAAATGT|TCTGCTAGCT|TGTTTTCTTC|ACAGTGCAGT|4020|
|GAATTGGAAG|ACTTGACTGC|AAATACAAAC|ACCCAGGATC|CTTTCTTGAT|TGGTTCTTCC|4080|
|AAACAAATGA|GGCATCAGTC|TGAAAGCCAG|GGAGTTGGTC|TGAGTGACAA|GGAATTGGTT|4140|

| | | | | | | |
|---|---|---|---|---|---|---|
| TCAGATGATG | AAGAAAGAGG | AACGGGCTTG | GAAGAAAATA | ATCAAGAAGA | GCAAAGCATG | 4200 |
| GATTCAAACT | TAGGTGAAGC | AGCATCTGGG | TGTGAGAGTG | AAACAAGCGT | CTCTGAAGAC | 4260 |
| TGCTCAGGGC | TATCCTCTCA | GAGTGACATT | TTAACCACTC | AGCAGAGGGA | TACCATGCAA | 4320 |
| CATAACCTGA | TAAAGCTCCA | GCAGGAAATG | GCTGAACTAG | AAGCTGTGTT | AGAACAGCAT | 4380 |
| GGGAGCCAGC | CTTCTAACAG | CTACCCTTCC | ATCATAAGTG | ACTCTTCTGC | CCTTGAGGAC | 4440 |
| CTGCGAAATC | CAGAACAAAG | CACATCAGAA | AAAGCAGTAT | TAACTTCACA | GAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | CAGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AAGAATGTCC | ATGGTGGTGT | CTGGCCTGAC | CCCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |
| GTAGCACTCT | ACCAGTGCCA | GGAGCTGGAC | ACCTACCTGA | TACCCCAGAT | CCCCCACAGC | 5700 |
| CACTACTGA | | | | | | 5709 |

( 2 ) INFORMATION FOR SEQ ID NO:3:

( i ) SEQUENCE CHARACTERISTICS:
        ( A ) LENGTH: 5689 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | AGCCTACAAG | AAAGTACGAG | ATTTAGTCAA | CTTGTTGAAG | AGCTATTGAA | 360 |
| AATCATTTGT | GCTTTTCAGC | TTGACACAGG | TTTGGAGTAT | GCAAACAGCT | ATAATTTTGC | 420 |

| | | | | | | |
|---|---|---|---|---|---|---|
| AAAAAAGGAA | AATAACTCTC | CTGAACATCT | AAAAGATGAA | GTTTCTATCA | TCCAAAGTAT | 480 |
| GGGCTACAGA | AACCGTGCCA | AAAGACTTCT | ACAGAGTGAA | CCCGAAAATC | CTTCCTTGCA | 540 |
| GGAAACCAGT | CTCAGTGTCC | AACTCTCTAA | CCTTGGAACT | GTGAGAACTC | TGAGGACAAA | 600 |
| GCAGCGGATA | CAACCTCAAA | AGACGTCTGT | CTACATTGAA | TTGGGATCTG | ATTCTTCTGA | 660 |
| AGATACCGTT | AATAAGGCAA | CTTATTGCAG | TGTGGGAGAT | CAAGAATTGT | TACAAATCAC | 720 |
| CCCTCAAGGA | ACCAGGGATG | AAATCAGTTT | GGATTCTGCA | AAAAAGGCTG | CTTGTGAATT | 780 |
| TTCTGAGACG | GATGTAACAA | ATACTGAACA | TCATCAACCC | AGTAATAATG | ATTTGAACAC | 840 |
| CACTGAGAAG | CGTGCAGCTG | AGAGGCATCC | AGAAAAGTAT | CAGGGTAGTT | CTGTTTCAAA | 900 |
| CTTGCATGTG | GAGCCATGTG | GCACAAATAC | TCATGCCAGC | TCATTACAGC | ATGAAACAG | 960 |
| CAGTTTATTA | CTCACTAAAG | ACAGAATGAA | TGTAGAAAAG | GCTGAATTCT | GTAATAAAAG | 1020 |
| CAAACAGCCT | GGCTTAGCAA | GGAGCCAACA | TAACAGATGG | GCTGGAAGTA | AGGAAACATG | 1080 |
| TAATGATAGG | CGGACTCCCA | GCACAGAAAA | AAAGGTAGAT | CTGAATGCTG | ATCCCCTGTG | 1140 |
| TGAGAGAAAA | GAATGGAATA | AGCAGAAACT | GCCATGCTCA | GAGAATCCTA | GAGATACTGA | 1200 |
| AGATGTTCCT | TGGATAACAC | TAAATAGCAG | CATTCAGAAA | GTTAATGAGT | GGTTTTCCAG | 1260 |
| AAGTGATGAA | CTGTTAGGTT | CTGATGACTC | ACATGATGGG | GAGTCTGAAT | CAAATGCCAA | 1320 |
| AGTAGCTGAT | GTATTGGACG | TTCTAAATGA | GGTAGATGAA | TATTCTGGTT | CTTCAGAGAA | 1380 |
| AATAGACTTA | CTGGCCAGTG | ATCCTCATGA | GGCTTTAATA | TGTAAAAGTG | AAAGAGTTCA | 1440 |
| CTCCAAATCA | GTAGAGAGTA | ATATTGAAGA | CAAATATTT | GGGAAAACCT | ATCGGAAGAA | 1500 |
| GGCAAGCCTC | CCCAACTTAA | GCCATGTAAC | TGAAAATCTA | ATTATAGGAG | CATTTGTTAC | 1560 |
| TGAGCCACAG | ATAATACAAG | AGCGTCCCCT | CACAAATAAA | TTAAAGCGTA | AAAGGAGACC | 1620 |
| TACATCAGGC | CTTCATCCTG | AGGATTTTAT | CAAGAAAGCA | GATTTGGCAG | TTCAAAAGAC | 1680 |
| TCCTGAAATG | ATAAATCAGG | GAACTAACCA | AACGGAGCAG | AATGGTCAAG | TGATGAATAT | 1740 |
| TACTAATAGT | GGTCATGAGA | ATAAAACAAA | AGGTGATTCT | ATTCAGAATG | AGAAAAATCC | 1800 |
| TAACCCAATA | GAATCACTCG | AAAAAGAATC | TGCTTTCAAA | ACGAAAGCTG | AACCTATAAG | 1860 |
| CAGCAGTATA | AGCAATATGG | AACTCGAATT | AAATATCCAC | AATTCAAAAG | CACCTAAAAA | 1920 |
| GAATAGGCTG | AGGAGGAAGT | CTTCTACCAG | GCATATTCAT | GCGCTTGAAC | TAGTAGTCAG | 1980 |
| TAGAAATCTA | AGCCCACCTA | ATTGTACTGA | ATTGCAAATT | GATAGTTGTT | CTAGCAGTGA | 2040 |
| AGAGATAAAG | AAAAAAAAGT | ACAACCAAAT | GCCAGTCAGG | CACAGCAGAA | ACCTACAACT | 2100 |
| CATGGAAGGT | AAAGAACCTG | CAACTGGAGC | CAAGAAGAGT | AACAAGCCAA | ATGAACAGAC | 2160 |
| AAGTAAAAGA | CATGACAGCG | ATACTTTCCC | AGAGCTGAAG | TTAACAAATG | CACCTGGTTC | 2220 |
| TTTTACTAAG | TGTTCAAATA | CCAGTGAACT | TAAAGAATTT | GTCAATCCTA | GCCTTCCAAG | 2280 |
| AGAAGAAAAA | GAAGAGAAAC | TAGAAACAGT | TAAAGTGTCT | AATAATGCTG | AAGACCCCAA | 2340 |
| AGATCTCATG | TTAAGTGGAG | AAAGGGTTTT | GCAAACTGAA | AGATCTGTAG | AGAGTAGCAG | 2400 |
| TATTTCATTG | GTACCTGGTA | CTGATTATGG | CACTCAGGAA | AGTATCTCGT | TACTGGAAGT | 2460 |
| TAGCACTCTA | GGGAAGGCAA | AAACAGAACC | AAATAAATGT | GTGAGTCAGT | GTGCAGCATT | 2520 |
| TGAAAACCCC | AAGGGACTAA | TTCATGGTTG | TTCCAAAGAT | AATAGAAATG | ACACAGAAGG | 2580 |
| CTTTAAGTAT | CCATTGGGAC | ATGAAGTTAA | CCACAGTCGG | GAAACAAGCA | TAGAAATGGA | 2640 |
| AGAAAGTGAA | CTTGATGCTC | AGTATTTGCA | GAATACATTC | AAGGTTTCAA | AGCGCCAGTC | 2700 |
| ATTTGCTCCG | TTTTCAAATC | CAGGAAATGC | AGAAGAGGAA | TGTGCAACAT | TCTCTGCCCA | 2760 |
| CTCTGGGTCC | TTAAAGAAAC | AAAGTCCAAA | AGTCACTTTT | GAATGTGAAC | AAAAGGAAGA | 2820 |

```
AAATCAAGGA AAGAATGAGT CTAATATCAA GCCTGTACAG ACAGTTAATA TCACTGCAGG    2880
CTTTCCTGTG GTTGGTCAGA AAGATAAGCC AGTTGATAAT GCCAAATGTA GTATCAAAGG    2940
AGGCTCTAGG TTTTGTCTAT CATCTCAGTT CAGAGGCAAC GAAACTGGAC TCATTACTCC    3000
AAATAAACAT GGACTTTTAC AAAACCCATA TCGTATACCA CCACTTTTTC CCATCAAGTC    3060
ATTTGTTAAA ACTAAATGTA AGAAAAATCT GCTAGAGGAA AACTTTGAGG AACATTCAAT    3120
GTCACCTGAA AGAGAAATGG GAAATGAGAA CATTCCAAGT ACAGTGAGCA CAATTAGCCG    3180
TAATAACATT AGAGAAAATG TTTTAAAGA AGCCAGCTCA AGCAATATTA ATGAAGTAGG     3240
TTCCAGTACT AATGAAGTGG GCTCCAGTAT TAATGAAATA GGTTCCAGTG ATGAAAACAT    3300
TCAAGCAGAA CTAGGTAGAA ACAGAGGGCC AAAATTGAAT GCTATGCTTA GATTAGGGGT    3360
TTTGCAACCT GAGGTCTATA AACAAAGTCT TCCTGGAAGT AATTGTAAGC ATCCTGAAAT    3420
AAAAAAGCAA GAATATGAAG AAGTAGTTCA GACTGTTAAT ACAGATTTCT CTCCATATCT    3480
GATTTCAGAT AACTTAGAAC AGCCTATGGG AAGTAGTCAT GCATCTCAGG TTTGTTCTGA    3540
GACACCTGAT GACCTGTTAG ATGATGGTGA AATAAAGGAA GATACTAGTT TTGCTGAAAA    3600
TGACATTAAG GAAAGTTCTG CTGTTTTTAG CAAAAGCGTC CAGAAAGGAG AGCTTAGCAG    3660
GAGTCCTAGC CCTTTCACCC ATACACATTT GGCTCAGGGT TACCGAAGAG GGCCAAGAA    3720
ATTAGAGTCC TCAGAAGAGA ACTTATCTAG TGAGGATGAA GAGCTTCCCT GCTTCCAACA    3780
CTTGTTATTT GGTAAAGTAA ACAATATACC TTCTCAGTCT ACTAGGCATA GCACCGTTGC    3840
TACCGAGTGT CTGTCTAAGA ACACAGAGGA GAATTTATTA TCATTGAAGA ATAGCTTAAA    3900
TGACTGCAGT AACCAGGTAA TATTGGCAAA GGCATCTCAG GAACATCACC TTAGTGAGGA    3960
AACAAAATGT TCTGCTAGCT TGTTTTCTTC ACAGTGCAGT GAATTGGAAG ACTTGACTGC    4020
AAATACAAAC ACCCAGGATC CTTTCTTGAT TGGTTCTTCC AAACAAATGA GGCATCAGTC    4080
TGAAAGCCAG GGAGTTGGTC TGAGTGACAA GGAATTGGTT TCAGATGATG AAGAAAGAGG    4140
AACGGGCTTG GAAGAAAATA ATCAAGAAGA GCAAAGCATG GATTCAAACT AGGTGAAGC    4200
AGCATCTGGG TGTGAGAGTG AAACAAGCGT CTCTGAAGAC TGCTCAGGGC TATCCTCTCA    4260
GAGTGACATT TTAACCACTC AGCAGAGGGA TACCATGCAA CATAACCTGA TAAAGCTCCA    4320
GCAGGAAATG GCTGAACTAG AAGCTGTGTT AGAACAGCAT GGGAGCCAGC CTTCTAACAG    4380
CTACCCTTCC ATCATAAGTG ACTCTTCTGC CCTTGAGGAC CTGCGAAATC CAGAACAAAG    4440
CACATCAGAA AAAGCAGTAT TAACTTCACA GAAAAGTAGT GAATACCCTA TAAGCCAGAA    4500
TCCAGAAGGC CTTTCTGCTG ACAAGTTTGA GGTGTCTGCA GATAGTTCTA CCAGTAAAAA    4560
TAAAGAACCA GGAGTGGAAA GGTCATCCCC TTCTAAATGC CCATCATTAG ATGATAGGTG    4620
GTACATGCAC AGTTGCTCTG GGAGTCTTCA GAATAGAAAC TACCCATCTC AAGAGGAGCT    4680
CATTAAGGTT GTTGATGTGG AGGAGCAACA GCTGGAAGAG TCTGGGCCAC ACGATTTGAC    4740
GGAAACATCT TACTTGCCAA GGCAAGATCT AGAGGGAACC CCTTACCTGG AATCTGGAAT    4800
CAGCCTCTTC TCTGATGACC CTGAATCTGA TCCTTCTGAA GACAGAGCCC CAGAGTCAGC    4860
TCGTGTTGGC AACATACCAT CTTCAACCTC TGCATTGAAA GTTCCCCAAT TGAAAGTTGC    4920
AGAATCTGCC CAGAGTCCAG CTGCTGCTCA TACTACTGAT ACTGCTGGGT ATAATGCAAT    4980
GGAAGAAAGT GTGAGCAGGG AGAAGCCAGA ATTGACAGCT TCAACAGAAA GGGTCAACAA    5040
AGAATGTCC ATGGTGGTGT CTGGCCTGAC CCCAGAAGAA TTTATGCTCG TGTACAAGTT     5100
TGCCAGAAAA CACCACATCA CTTTAACTAA TCTAATTACT GAAGAGACTA CTCATGTTGT    5160
TATGAAAACA GATGCTGAGT TTGTGTGTGA ACGGACACTG AAATATTTTC TAGGAATTGC    5220
```

-continued

| | | | | | |
|---|---|---|---|---|---|
| GGGAGGAAAA | TGGGTAGTTA | GCTATTTCTG | GGTGACCCAG | TCTATTAAAG | AAAGAAAAAT | 5280
| GCTGAATGAG | CATGATTTTG | AAGTCAGAGG | AGATGTGGTC | AATGGAAGAA | ACCACCAAGG | 5340
| TCCAAAGCGA | GCAAGAGAAT | CCCAGGACAG | AAAGATCTTC | AGGGGGCTAG | AAATCTGTTG | 5400
| CTATGGGCCC | TTCACCAACA | TGCCCACAGA | TCAACTGGAA | TGGATGGTAC | AGCTGTGTGG | 5460
| TGCTTCTGTG | GTGAAGGAGC | TTTCATCATT | CACCCTTGGC | ACAGGTGTCC | ACCCAATTGT | 5520
| GGTTGTGCAG | CCAGATGCCT | GGACAGAGGA | CAATGGCTTC | CATGCAATTG | GCAGATGTG | 5580
| TGAGGCACCT | GTGGTGACCC | GAGAGTGGGT | GTTGGACAGT | GTAGCACTCT | ACCAGTGCCA | 5640
| GGAGCTGGAC | ACCTACCTGA | TACCCCAGAT | CCCCCACAGC | CACTACTGA | | 5689

( 2 ) INFORMATION FOR SEQ ID NO:4:

( i ) SEQUENCE CHARACTERISTICS:
    ( A ) LENGTH: 5711 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60
| CCTGCGCTCA | GGAGGCCTTC | ACCCTCTGCT | CTGGGTAAAG | TTCATTGGAA | CAGAAAGAAA | 120
| TGGATTTATC | TGCTCTTCGC | GTTGAAGAAG | TACAAAATGT | CATTAATGCT | ATGCAGAAAA | 180
| TCTTAGAGTG | TCCCATCTGT | CTGGAGTTGA | TCAAGGAACC | TGTCTCCACA | AAGTGTGACC | 240
| ACATATTTTG | CAAATTTTGC | ATGCTGAAAC | TTCTCAACCA | GAAGAAAGGG | CCTTCACAGG | 300
| GTCCTTTATG | TAAGAATGAT | ATAACCAAAA | GGAGCCTACA | AGAAAGTACG | AGATTTAGTC | 360
| AACTTGTTGA | AGAGCTATTG | AAAATCATTT | GTGCTTTTCA | GCTTGACACA | GGTTTGGAGT | 420
| ATGCAAACAG | CTATAATTTT | GCAAAAAAGG | AAAATAACTC | TCCTGAACAT | CTAAAAGATG | 480
| AAGTTTCTAT | CATCCAAAGT | ATGGGCTACA | GAAACCGTGC | CAAAAGACTT | CTACAGAGTG | 540
| AACCCGAAAA | TCCTTCCTTG | CAGGAAACCA | GTCTCAGTGT | CCAACTCTCT | AACCTTGGAA | 600
| CTGTGAGAAC | TCTGAGGACA | AAGCAGCGGA | TACAACCTCA | AAAGACGTCT | GTCTACATTG | 660
| AATTGGGATC | TGATTCTTCT | GAAGATACCG | TTAATAAGGC | AACTTATTGC | AGTGTGGGAG | 720
| ATCAAGAATT | GTTACAAATC | ACCCCTCAAG | GAACCAGGGA | TGAAATCAGT | TTGGATTCTG | 780
| CAAAAAAGGC | TGCTTGTGAA | TTTTCTGAGA | CGGATGTAAC | AAATACTGAA | CATCATCAAC | 840
| CCAGTAATAA | TGATTTGAAC | ACCACTGAGA | AGCGTGCAGC | TGAGAGGCAT | CCAGAAAAGT | 900
| ATCAGGGTAG | TTCTGTTTCA | AACTTGCATG | TGGAGCCATG | TGGCACAAAT | ACTCATGCCA | 960
| GCTCATTACA | GCATGAGAAC | AGCAGTTTAT | TACTCACTAA | AGACAGAATG | AATGTAGAAA | 1020
| AGGCTGAATT | CTGTAATAAA | AGCAAACAGC | CTGGCTTAGC | AAGGAGCCAA | CATAACAGAT | 1080
| GGGCTGGAAG | TAAGGAAACA | TGTAATGATA | GGCGGACTCC | CAGCACAGAA | AAAAGGTAG | 1140
| ATCTGAATGC | TGATCCCCTG | TGTGAGAGAA | AAGAATGGAA | TAAGCAGAAA | CTGCCATGCT | 1200
| CAGAGAATCC | TAGAGATACT | GAAGATGTTC | CTTGGATAAC | ACTAAATAGC | AGCATTCAGA | 1260
| AAGTTAATGA | GTGGTTTTCC | AGAAGTGATG | AACTGTTAGG | TTCTGATGAC | TCACATGATG | 1320
| GGGAGTCTGA | ATCAAATGCC | AAAGTAGCTG | ATGTATTGGA | CGTTCTAAAT | GAGGTAGATG | 1380
| AATATTCTGG | TTCTTCAGAG | AAAATAGACT | TACTGGCCAG | TGATCCTCAT | GAGGCTTTAA | 1440
| TATGTAAAAG | TGAAAGAGTT | CACTCCAAAT | CAGTAGAGAG | TAATATTGAA | GACAAAATAT | 1500

| | | | | | | |
|---|---|---|---|---|---|---|
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTTGTCT | ATCATCTCAG | TTCAGAGGCA | 3000 |
| ACGAAACTGG | ACTCATTACT | CCAAATAAAC | ATGGACTTTT | ACAAAACCCA | TATCGTATAC | 3060 |
| CACCACTTTT | TCCCATCAAG | TCATTTGTTA | AAACTAAATG | TAAGAAAAAT | CTGCTAGAGG | 3120 |
| AAAACTTTGA | GGAACATTCA | ATGTCACCTG | AAAGAGAAAT | GGGAAATGAG | AACATTCCAA | 3180 |
| GTACAGTGAG | CACAATTAGC | CGTAATAACA | TTAGAGAAAA | TGTTTTTAAA | GAAGCCAGCT | 3240 |
| CAAGCAATAT | TAATGAAGTA | GGTTCCAGTA | CTAATGAAGT | GGGCTCCAGT | ATTAATGAAA | 3300 |
| TAGGTTCCAG | TGATGAAAAC | ATTCAAGCAG | AACTAGGTAG | AAACAGAGGG | CCAAAATTGA | 3360 |
| ATGCTATGCT | TAGATTAGGG | GTTTTGCAAC | CTGAGGTCTA | TAAACAAAGT | CTTCCTGGAA | 3420 |
| GTAATTGTAA | GCATCCTGAA | ATAAAAAGC | AAGAATATGA | AGAAGTAGTT | CAGACTGTTA | 3480 |
| ATACAGATTT | CTCTCCATAT | CTGATTTCAG | ATAACTTAGA | ACAGCCTATG | GGAAGTAGTC | 3540 |
| ATGCATCTCA | GGTTTGTTCT | GAGACACCTG | ATGACCTGTT | AGATGATGGT | GAAATAAAGG | 3600 |
| AAGATACTAG | TTTTGCTGAA | AATGACATTA | AGGAAAGTTC | TGCTGTTTTT | AGCAAAAGCG | 3660 |
| TCCAGAAAGG | AGAGCTTAGC | AGGAGTCCTA | GCCCTTTCAC | CCATACACAT | TTGGCTCAGG | 3720 |
| GTTACCGAAG | AGGGGCCAAG | AAATTAGAGT | CCTCAGAAGA | GAACTTATCT | AGTGAGGATG | 3780 |
| AAGAGCTTCC | CTGCTTCCAA | CACTTGTTAT | TTGGTAAAGT | AAACAATATA | CCTTCTCAGT | 3840 |
| CTACTAGGCA | TAGCACCGTT | GCTACCGAGT | GTCTGTCTAA | GAACACAGAG | GAGAATTTAT | 3900 |

| | | | | | | |
|---|---|---|---|---|---|---|
| TATCATTGAA | GAATAGCTTA | AATGACTGCA | GTAACCAGGT | AATATTGGCA | AAGGCATCTC | 3960 |
| AGGAACATCA | CCTTAGTGAG | GAAACAAAAT | GTTCTGCTAG | CTTGTTTTCT | TCACAGTGCA | 4020 |
| GTGAATTGGA | AGACTTGACT | GCAAATACAA | ACACCCAGGA | TCCTTTCTTG | ATTGGTTCTT | 4080 |
| CCAAACAAAT | GAGGCATCAG | TCTGAAAGCC | AGGGAGTTGG | TCTGAGTGAC | AAGGAATTGG | 4140 |
| TTTCAGATGA | TGAAGAAAGA | GGAACGGGCT | TGGAAGAAAA | TAATCAAGAA | GAGCAAAGCA | 4200 |
| TGGATTCAAA | CTTAGGTGAA | GCAGCATCTG | GGTGTGAGAG | TGAAACAAGC | GTCTCTGAAG | 4260 |
| ACTGCTCAGG | GCTATCCTCT | CAGAGTGACA | TTTTAACCAC | TCAGCAGAGG | GATACCATGC | 4320 |
| AACATAACCT | GATAAAGCTC | CAGCAGGAAA | TGGCTGAACT | AGAAGCTGTG | TTAGAACAGC | 4380 |
| ATGGGAGCCA | GCCTTCTAAC | AGCTACCCTT | CCATCATAAG | TGACTCTTCT | GCCCTTGAGG | 4440 |
| ACCTGCGAAA | TCCAGAACAA | AGCACATCAG | AAAAGCAGT | ATTAACTTCA | CAGAAAAGTA | 4500 |
| GTGAATACCC | TATAAGCCAG | AATCCAGAAG | GCCTTTCTGC | TGACAAGTTT | GAGGTGTCTG | 4560 |
| CAGATAGTTC | TACCAGTAAA | AATAAGAAC | CAGGAGTGGA | AAGGTCATCC | CCTTCTAAAT | 4620 |
| GCCCATCATT | AGATGATAGG | TGGTACATGC | ACAGTTGCTC | TGGGAGTCTT | CAGAATAGAA | 4680 |
| ACTACCCATC | TCAAGAGGAG | CTCATTAAGG | TTGTTGATGT | GGAGGAGCAA | CAGCTGGAAG | 4740 |
| AGTCTGGGCC | ACACGATTTG | ACGGAAACAT | CTTACTTGCC | AAGGCAAGAT | CTAGAGGGAA | 4800 |
| CCCCTTACCT | GGAATCTGGA | ATCAGCCTCT | TCTCTGATGA | CCCTGAATCT | GATCCTTCTG | 4860 |
| AAGACAGAGC | CCCAGAGTCA | GCTCGTGTTG | GCAACATACC | ATCTTCAACC | TCTGCATTGA | 4920 |
| AAGTTCCCCA | ATTGAAAGTT | GCAGAATCTG | CCCAGAGTCC | AGCTGCTGCT | CATACTACTG | 4980 |
| ATACTGCTGG | GTATAATGCA | ATGGAAGAAA | GTGTGAGCAG | GGAGAAGCCA | GAATTGACAG | 5040 |
| CTTCAACAGA | AAGGGTCAAC | AAAAGAATGT | CCATGGTGGT | GTCTGGCCTG | ACCCCAGAAG | 5100 |
| AATTTATGCT | CGTGTACAAG | TTTGCCAGAA | ACACCACAT | CACTTAACT | AATCTAATTA | 5160 |
| CTGAAGAGAC | TACTCATGTT | GTTATGAAAA | CAGATGCTGA | GTTTGTGTGT | GAACGGACAC | 5220 |
| TGAAATATTT | TCTAGGAATT | GCGGGAGGAA | AATGGGTAGT | TAGCTATTTC | TGGGTGACCC | 5280 |
| AGTCTATTAA | AGAAAGAAAA | ATGCTGAATG | AGCATGATTT | TGAAGTCAGA | GGAGATGTGG | 5340 |
| TCAATGGAAG | AAACCACCAA | GGTCCAAAGC | GAGCAAGAGA | ATCCCAGGAC | AGAAAGATCT | 5400 |
| TCAGGGGGCT | AGAAATCTGT | TGCTATGGGC | CCTTCACCAA | CATGCCCACA | GATCAACTGG | 5460 |
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCAG | ATCCCCCACA | 5700 |
| GCCACTACTG | A | | | | | 5711 |

( 2 ) INFORMATION FOR SEQ ID NO:5:

( i ) SEQUENCE CHARACTERISTICS:
( A ) LENGTH: 5770 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |

-continued

| | | | | | |
|---|---|---|---|---|---|
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GTGTCCTTAA | AAGGTTGATA | ATCACTTGCT | 360 |
| GAGTGTGTTT | CTCAAACAAG | TTAATTTCAG | GAGCCTACAA | GAAAGTACGA | GATTTAGTCA | 420 |
| ACTTGTTGAA | GAGCTATTGA | AAATCATTTG | TGCTTTTCAG | CTTGACACAG | GTTTGGAGTA | 480 |
| TGCAAACAGC | TATAATTTTG | CAAAAAAGGA | AAATAACTCT | CCTGAACATC | TAAAAGATGA | 540 |
| AGTTTCTATC | ATCCAAAGTA | TGGGCTACAG | AAACCGTGCC | AAAAGACTTC | TACAGAGTGA | 600 |
| ACCCGAAAAT | CCTTCCTTGC | AGGAAACCAG | TCTCAGTGTC | CAACTCTCTA | ACCTTGGAAC | 660 |
| TGTGAGAACT | CTGAGGACAA | AGCAGCGGAT | ACAACCTCAA | AAGACGTCTG | TCTACATTGA | 720 |
| ATTGGGATCT | GATTCTTCTG | AAGATACCGT | TAATAAGGCA | ACTTATTGCA | GTGTGGGAGA | 780 |
| TCAAGAATTG | TTACAAATCA | CCCCTCAAGG | AACCAGGGAT | GAAATCAGTT | TGGATTCTGC | 840 |
| AAAAAAGGCT | GCTTGTGAAT | TTTCTGAGAC | GGATGTAACA | AATACTGAAC | ATCATCAACC | 900 |
| CAGTAATAAT | GATTTGAACA | CCACTGAGAA | GCGTGCAGCT | GAGAGGCATC | CAGAAAAGTA | 960 |
| TCAGGGTAGT | TCTGTTTCAA | ACTTGCATGT | GGAGCCATGT | GGCACAAATA | CTCATGCCAG | 1020 |
| CTCATTACAG | CATGAGAACA | GCAGTTTATT | ACTCACTAAA | GACAGAATGA | ATGTAGAAAA | 1080 |
| GGCTGAATTC | TGTAATAAAA | GCAAACAGCC | TGGCTTAGCA | AGGAGCCAAC | ATAACAGATG | 1140 |
| GGCTGGAAGT | AAGGAAACAT | GTAATGATAG | GCGGACTCCC | AGCACAGAAA | AAAAGGTAGA | 1200 |
| TCTGAATGCT | GATCCCCTGT | GTGAGAGAAA | AGAATGGAAT | AAGCAGAAAC | TGCCATGCTC | 1260 |
| AGAGAATCCT | AGAGATACTG | AAGATGTTCC | TTGGATAACA | CTAAATAGCA | GCATTCAGAA | 1320 |
| AGTTAATGAG | TGGTTTTCCA | GAAGTGATGA | ACTGTTAGGT | TCTGATGACT | CACATGATGG | 1380 |
| GGAGTCTGAA | TCAAATGCCA | AAGTAGCTGA | TGTATTGGAC | GTTCTAAATG | AGGTAGATGA | 1440 |
| ATATTCTGGT | TCTTCAGAGA | AAATAGACTT | ACTGGCCAGT | GATCCTCATG | AGGCTTTAAT | 1500 |
| ATGTAAAAGT | GAAAGAGTTC | ACTCCAAATC | AGTAGAGAGT | AATATTGAAG | ACAAAATATT | 1560 |
| TGGGAAAACC | TATCGGAAGA | AGGCAAGCCT | CCCCAACTTA | AGCCATGTAA | CTGAAAATCT | 1620 |
| AATTATAGGA | GCATTTGTTA | CTGAGCCACA | GATAATACAA | GAGCGTCCCC | TCACAAATAA | 1680 |
| ATTAAAGCGT | AAAAGGAGAC | CTACATCAGG | CCTTCATCCT | GAGGATTTTA | TCAAGAAAGC | 1740 |
| AGATTTGGCA | GTTCAAAAGA | CTCCTGAAAT | GATAAATCAG | GGAACTAACC | AAACGGAGCA | 1800 |
| GAATGGTCAA | GTGATGAATA | TTACTAATAG | TGGTCATGAG | AATAAAACAA | AAGGTGATTC | 1860 |
| TATTCAGAAT | GAGAAAAATC | CTAACCCAAT | AGAATCACTC | GAAAAAGAAT | CTGCTTTCAA | 1920 |
| AACGAAAGCT | GAACCTATAA | GCAGCAGTAT | AAGCAATATG | GAACTCGAAT | TAAATATCCA | 1980 |
| CAATTCAAAA | GCACCTAAAA | AGAATAGGCT | GAGGAGGAAG | TCTTCTACCA | GGCATATTCA | 2040 |
| TGCGCTTGAA | CTAGTAGTCA | GTAGAAATCT | AAGCCCACCT | AATTGTACTG | AATTGCAAAT | 2100 |
| TGATAGTTGT | TCTAGCAGTG | AAGAGATAAA | GAAAAAAAAG | TACAACCAAA | TGCCAGTCAG | 2160 |
| GCACAGCAGA | AACCTACAAC | TCATGGAAGG | TAAAGAACCT | GCAACTGGAG | CCAAGAAGAG | 2220 |
| TAACAAGCCA | AATGAACAGA | CAAGTAAAAG | ACATGACAGC | GATACTTTCC | CAGAGCTGAA | 2280 |
| GTTAACAAAT | GCACCTGGTT | CTTTTACTAA | GTGTTCAAAT | ACCAGTGAAC | TTAAAGAATT | 2340 |
| TGTCAATCCT | AGCCTTCCAA | GAGAAGAAAA | AGAAGAGAAA | CTAGAAACAG | TTAAAGTGTC | 2400 |
| TAATAATGCT | GAAGACCCCA | AAGATCTCAT | GTTAAGTGGA | GAAAGGGTTT | TGCAAACTGA | 2460 |
| AAGATCTGTA | GAGAGTAGCA | GTATTTCATT | GGTACCTGGT | ACTGATTATG | GCACTCAGGA | 2520 |
| AAGTATCTCG | TTACTGGAAG | TTAGCACTCT | AGGGAAGGCA | AAAACAGAAC | CAAATAAATG | 2580 |

| | | | | | |
|---|---|---|---|---|---|
| TGTGAGTCAG | TGTGCAGCAT | TTGAAAACCC | CAAGGGACTA | ATTCATGGTT | GTTCCAAAGA 2640 |
| TAATAGAAAT | GACACAGAAG | GCTTTAAGTA | TCCATTGGGA | CATGAAGTTA | ACCACAGTCG 2700 |
| GGAAACAAGC | ATAGAAATGG | AAGAAAGTGA | ACTTGATGCT | CAGTATTTGC | AGAATACATT 2760 |
| CAAGGTTTCA | AAGCGCCAGT | CATTTGCTCC | GTTTTCAAAT | CCAGGAAATG | CAGAAGAGGA 2820 |
| ATGTGCAACA | TTCTCTGCCC | ACTCTGGGTC | CTTAAAGAAA | CAAAGTCCAA | AAGTCACTTT 2880 |
| TGAATGTGAA | CAAAAGGAAG | AAAATCAAGG | AAAGAATGAG | TCTAATATCA | AGCCTGTACA 2940 |
| GACAGTTAAT | ATCACTGCAG | GCTTTCCTGT | GGTTGGTCAG | AAAGATAAGC | CAGTTGATAA 3000 |
| TGCCAAATGT | AGTATCAAAG | GAGGCTCTAG | GTTTTGTCTA | TCATCTCAGT | TCAGAGGCAA 3060 |
| CGAAACTGGA | CTCATTACTC | CAAATAAACA | TGGACTTTTA | CAAAACCCAT | ATCGTATACC 3120 |
| ACCACTTTTT | CCCATCAAGT | CATTTGTTAA | AACTAAATGT | AAGAAAATC | TGCTAGAGGA 3180 |
| AAACTTTGAG | GAACATTCAA | TGTCACCTGA | AAGAGAAATG | GAAATGAGA | ACATTCCAAG 3240 |
| TACAGTGAGC | ACAATTAGCC | GTAATAACAT | TAGAGAAAAT | GTTTTAAAG | AAGCCAGCTC 3300 |
| AAGCAATATT | AATGAAGTAG | GTTCCAGTAC | TAATGAAGTG | GGCTCCAGTA | TTAATGAAAT 3360 |
| AGGTTCCAGT | GATGAAAACA | TTCAAGCAGA | ACTAGGTAGA | AACAGAGGGC | CAAAATTGAA 3420 |
| TGCTATGCTT | AGATTAGGGG | TTTTGCAACC | TGAGGTCTAT | AAACAAAGTC | TTCCTGGAAG 3480 |
| TAATTGTAAG | CATCCTGAAA | TAAAAAAGCA | AGAATATGAA | GAAGTAGTTC | AGACTGTTAA 3540 |
| TACAGATTTC | TCTCCATATC | TGATTTCAGA | TAACTTAGAA | CAGCCTATGG | GAAGTAGTCA 3600 |
| TGCATCTCAG | GTTTGTTCTG | AGACACCTGA | TGACCTGTTA | GATGATGGTG | AAATAAAGGA 3660 |
| AGATACTAGT | TTTGCTGAAA | ATGACATTAA | GGAAAGTTCT | GCTGTTTTTA | GCAAAAGCGT 3720 |
| CCAGAAAGGA | GAGCTTAGCA | GGAGTCCTAG | CCCTTTCACC | CATACACATT | TGGCTCAGGG 3780 |
| TTACCGAAGA | GGGGCCAAGA | AATTAGAGTC | CTCAGAAGAG | AACTTATCTA | GTGAGGATGA 3840 |
| AGAGCTTCCC | TGCTTCCAAC | ACTTGTTATT | TGGTAAAGTA | AACAATATAC | CTTCTCAGTC 3900 |
| TACTAGGCAT | AGCACCGTTG | CTACCGAGTG | TCTGTCTAAG | AACACAGAGG | AGAATTTATT 3960 |
| ATCATTGAAG | AATAGCTTAA | ATGACTGCAG | TAACCAGGTA | ATATTGGCAA | AGGCATCTCA 4020 |
| GGAACATCAC | CTTAGTGAGG | AAACAAAATG | TTCTGCTAGC | TTGTTTTCTT | CACAGTGCAG 4080 |
| TGAATTGGAA | GACTTGACTG | CAAATACAAA | CACCCAGGAT | CCTTTCTTGA | TTGGTTCTTC 4140 |
| CAAACAAATG | AGGCATCAGT | CTGAAAGCCA | GGGAGTTGGT | CTGAGTGACA | AGGAATTGGT 4200 |
| TTCAGATGAT | GAAGAAAGAG | GAACGGGCTT | GGAAGAAAAT | AATCAAGAAG | AGCAAAGCAT 4260 |
| GGATTCAAAC | TTAGGTGAAG | CAGCATCTGG | GTGTGAGAGT | GAAACAAGCG | TCTCTGAAGA 4320 |
| CTGCTCAGGG | CTATCCTCTC | AGAGTGACAT | TTTAACCACT | CAGCAGAGGG | ATACCATGCA 4380 |
| ACATAACCTG | ATAAAGCTCC | AGCAGGAAAT | GGCTGAACTA | GAAGCTGTGT | TAGAACAGCA 4440 |
| TGGGAGCCAG | CCTTCTAACA | GCTACCCTTC | CATCATAAGT | GACTCTTCTG | CCCTTGAGGA 4500 |
| CCTGCGAAAT | CCAGAACAAA | GCACATCAGA | AAAAGCAGTA | TTAACTTCAC | AGAAAAGTAG 4560 |
| TGAATACCCT | ATAAGCCAGA | ATCCAGAAGG | CCTTTCTGCT | GACAAGTTTG | AGGTGTCTGC 4620 |
| AGATAGTTCT | ACCAGTAAAA | ATAAAGAACC | AGGAGTGGAA | AGGTCATCCC | CTTCTAAATG 4680 |
| CCCATCATTA | GATGATAGGT | GGTACATGCA | CAGTTGCTCT | GGGAGTCTTC | AGAATAGAAA 4740 |
| CTACCCATCT | CAAGAGGAGC | TCATTAAGGT | TGTTGATGTG | GAGGAGCAAC | AGCTGGAAGA 4800 |
| GTCTGGGCCA | CACGATTTGA | CGGAAACATC | TTACTTGCCA | AGGCAAGATC | TAGAGGGAAC 4860 |
| CCCTTACCTG | GAATCTGGAA | TCAGCCTCTT | CTCTGATGAC | CCTGAATCTG | ATCCTTCTGA 4920 |
| AGACAGAGCC | CCAGAGTCAG | CTCGTGTTGG | CAACATACCA | TCTTCAACCT | CTGCATTGAA 4980 |

| | | | | | |
|---|---|---|---|---|---|
| AGTTCCCCAA | TTGAAAGTTG | CAGAATCTGC | CCAGAGTCCA | GCTGCTGCTC | ATACTACTGA | 5040 |
| TACTGCTGGG | TATAATGCAA | TGGAAGAAAG | TGTGAGCAGG | GAGAAGCCAG | AATTGACAGC | 5100 |
| TTCAACAGAA | AGGGTCAACA | AAAGAATGTC | CATGGTGGTG | TCTGGCCTGA | CCCCAGAAGA | 5160 |
| ATTTATGCTC | GTGTACAAGT | TTGCCAGAAA | ACACCACATC | ACTTAACTA | ATCTAATTAC | 5220 |
| TGAAGAGACT | ACTCATGTTG | TTATGAAAAC | AGATGCTGAG | TTTGTGTGTG | AACGGACACT | 5280 |
| GAAATATTTT | CTAGGAATTG | CGGGAGGAAA | ATGGGTAGTT | AGCTATTTCT | GGGTGACCCA | 5340 |
| GTCTATTAAA | GAAAGAAAAA | TGCTGAATGA | GCATGATTTT | GAAGTCAGAG | GAGATGTGGT | 5400 |
| CAATGGAAGA | AACCACCAAG | GTCCAAAGCG | AGCAAGAGAA | TCCCAGGACA | GAAAGATCTT | 5460 |
| CAGGGGGCTA | GAAATCTGTT | GCTATGGGCC | CTTCACCAAC | ATGCCCACAG | ATCAACTGGA | 5520 |
| ATGGATGGTA | CAGCTGTGTG | GTGCTTCTGT | GGTGAAGGAG | CTTTCATCAT | TCACCCTTGG | 5580 |
| CACAGGTGTC | CACCCAATTG | TGGTTGTGCA | GCCAGATGCC | TGGACAGAGG | ACAATGGCTT | 5640 |
| CCATGCAATT | GGGCAGATGT | GTGAGGCACC | TGTGGTGACC | CGAGAGTGGG | TGTTGGACAG | 5700 |
| TGTAGCACTC | TACCAGTGCC | AGGAGCGGAC | ACCTAACCTG | ATACCCCAGA | TCCCCCACAG | 5760 |
| CCACTACTGA | | | | | | 5770 |

( 2 ) INFORMATION FOR SEQ ID NO:6:

( i ) SEQUENCE CHARACTERISTICS:
( A ) LENGTH: 5710 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACGCC | TGGCTTAGCA | AGGAGCCAAC | ATAACAGATG | 1080 |
| GGCTGGAAGT | AAGGAAACAT | GTAATGATAG | GCGGACTCCC | AGCACAGAAA | AAAGGTAGA | 1140 |

```
TCTGAATGCT GATCCCCTGT GTGAGAGAAA AGAATGGAAT AAGCAGAAAC TGCCATGCTC      1200
AGAGAATCCT AGAGATACTG AAGATGTTCC TTGGATAACA CTAAATAGCA GCATTCAGAA      1260
AGTTAATGAG TGGTTTTCCA GAAGTGATGA ACTGTTAGGT TCTGATGACT CACATGATGG      1320
GGAGTCTGAA TCAAATGCCA AAGTAGCTGA TGTATTGGAC GTTCTAAATG AGGTAGATGA      1380
ATATTCTGGT TCTTCAGAGA AAATAGACTT ACTGGCCAGT GATCCTCATG AGGCTTTAAT      1440
ATGTAAAAGT GAAAGAGTTC ACTCCAAATC AGTAGAGAGT AATATTGAAG ACAAAATATT      1500
TGGGAAAACC TATCGGAAGA AGGCAAGCCT CCCCAACTTA AGCCATGTAA CTGAAAATCT      1560
AATTATAGGA GCATTTGTTA CTGAGCCACA GATAATACAA GAGCGTCCCC TCACAAATAA      1620
ATTAAAGCGT AAAAGGAGAC CTACATCAGG CCTTCATCCT GAGGATTTTA TCAAGAAAGC      1680
AGATTTGGCA GTTCAAAAGA CTCCTGAAAT GATAAATCAG GAACTAACC AAACGGAGCA       1740
GAATGGTCAA GTGATGAATA TTACTAATAG TGGTCATGAG AATAAACAA AAGGTGATTC       1800
TATTCAGAAT GAGAAAAATC CTAACCCAAT AGAATCACTC GAAAAGAAT CTGCTTTCAA       1860
AACGAAAGCT GAACCTATAA GCAGCAGTAT AAGCAATATG GAACTCGAAT TAAATATCCA      1920
CAATTCAAAA GCACCTAAAA AGAATAGGCT GAGGAGGAAG TCTTCTACCA GGCATATTCA      1980
TGCGCTTGAA CTAGTAGTCA GTAGAAATCT AAGCCCACCT AATTGTACTG AATTGCAAAT      2040
TGATAGTTGT TCTAGCAGTG AAGAGATAAA GAAAAAAAG TACAACCAAA TGCCAGTCAG       2100
GCACAGCAGA AACCTACAAC TCATGGAAGG TAAAGAACCT GCAACTGGAG CCAAGAAGAG      2160
TAACAAGCCA AATGAACAGA CAAGTAAAAG ACATGACAGC GATACTTTCC CAGAGCTGAA      2220
GTTAACAAAT GCACCTGGTT CTTTTACTAA GTGTTCAAAT ACCAGTGAAC TTAAAGAATT      2280
TGTCAATCCT AGCCTTCCAA GAGAAGAAAA AGAAGAGAAA CTAGAAACAG TTAAAGTGTC      2340
TAATAATGCT GAAGACCCCA AAGATCTCAT GTTAAGTGGA GAAAGGGTTT GCAAACTGA       2400
AAGATCTGTA GAGAGTAGCA GTATTTCATT GGTACCTGGT ACTGATTATG GCACTCAGGA      2460
AAGTATCTCG TTACTGGAAG TTAGCACTCT AGGGAAGGCA AAAACAGAAC CAAATAAATG      2520
TGTGAGTCAG TGTGCAGCAT TTGAAAACCC CAAGGGACTA ATTCATGGTT GTTCCAAAGA      2580
TAATAGAAAT GACACAGAAG CTTTAAGTA TCCATTGGGA CATGAAGTTA ACCACAGTCG       2640
GGAAACAAGC ATAGAAATGG AAGAAAGTGA ACTTGATGCT CAGTATTTGC AGAATACATT      2700
CAAGGTTTCA AAGCGCCAGT CATTTGCTCC GTTTTCAAAT CCAGGAAATG CAGAAGAGGA      2760
ATGTGCAACA TTCTCTGCCC ACTCTGGGTC CTTAAAGAAA CAAAGTCCAA AAGTCACTTT      2820
TGAATGTGAA CAAAAGGAAG AAAATCAAGG AAAGAATGAG TCTAATATCA AGCCTGTACA      2880
GACAGTTAAT ATCACTGCAG GCTTTCCTGT GGTTGGTCAG AAAGATAAGC CAGTTGATAA      2940
TGCCAAATGT AGTATCAAAG GAGGCTCTAG GTTTTGTCTA TCATCTCAGT TCAGAGGCAA      3000
CGAAACTGGA CTCATTACTC CAAATAAACA TGGACTTTTA CAAAACCCAT ATCGTATACC      3060
ACCACTTTTT CCCATCAAGT CATTTGTTAA AACTAAATGT AAGAAAATC TGCTAGAGGA       3120
AAACTTTGAG GAACATTCAA TGTCACCTGA AAGAGAAATG GGAAATGAGA CATTCCAAG       3180
TACAGTGAGC ACAATTAGCC GTAATAACAT TAGAGAAAAT GTTTTTAAAG AAGCCAGCTC      3240
AAGCAATATT AATGAAGTAG GTTCCAGTAC TAATGAAGTG GGCTCCAGTA TTAATGAAAT      3300
AGGTTCCAGT GATGAAAACA TTCAAGCAGA ACTAGGTAGA AACAGAGGGC CAAAATTGAA      3360
TGCTATGCTT AGATTAGGGG TTTTGCAACC TGAGGTCTAT AAACAAAGTC TTCCTGGAAG      3420
TAATTGTAAG CATCCTGAAA TAAAAAAGCA AGAATATGAA GAAGTAGTTC AGACTGTTAA      3480
TACAGATTTC TCTCCATATC TGATTTCAGA TAACTTAGAA CAGCCTATGG GAAGTAGTCA      3540
```

```
TGCATCTCAG GTTTGTTCTG AGACACCTGA TGACCTGTTA GATGATGGTG AAATAAAGGA    3600
AGATACTAGT TTTGCTGAAA ATGACATTAA GGAAAGTTCT GCTGTTTTTA GCAAAAGCGT    3660
CCAGAAAGGA GAGCTTAGCA GGAGTCCTAG CCCTTTCACC CATACACATT TGGCTCAGGG    3720
TTACCGAAGA GGGGCCAAGA AATTAGAGTC CTCAGAAGAG AACTTATCTA GTGAGGATGA    3780
AGAGCTTCCC TGCTTCCAAC ACTTGTTATT TGGTAAAGTA AACAATATAC CTTCTCAGTC    3840
TACTAGGCAT AGCACCGTTG CTACCGAGTG TCTGTCTAAG AACACAGAGG AGAATTTATT    3900
ATCATTGAAG AATAGCTTAA ATGACTGCAG TAACCAGGTA ATATTGGCAA AGGCATCTCA    3960
GGAACATCAC CTTAGTGAGG AAACAAAATG TTCTGCTAGC TTGTTTTCTT CACAGTGCAG    4020
TGAATTGGAA GACTTGACTG CAAATACAAA CACCCAGGAT CCTTTCTTGA TTGGTTCTTC    4080
CAAACAAATG AGGCATCAGT CTGAAAGCCA GGGAGTTGGT CTGAGTGACA AGGAATTGGT    4140
TTCAGATGAT GAAGAAAGAG GAACGGGCTT GGAAGAAAAT AATCAAGAAG AGCAAAGCAT    4200
GGATTCAAAC TTAGGTGAAG CAGCATCTGG GTGTGAGAGT GAAACAAGCG TCTCTGAAGA    4260
CTGCTCAGGG CTATCCTCTC AGAGTGACAT TTTAACCACT CAGCAGAGGG ATACCATGCA    4320
ACATAACCTG ATAAAGCTCC AGCAGGAAAT GGCTGAACTA GAAGCTGTGT TAGAACAGCA    4380
TGGGAGCCAG CCTTCTAACA GCTACCCTTC CATCATAAGT GACTCTTCTG CCCTTGAGGA    4440
CCTGCGAAAT CCAGAACAAA GCACATCAGA AAAGCAGTA TTAACTTCAC AGAAAAGTAG    4500
TGAATACCCT ATAAGCCAGA ATCCAGAAGG CCTTTCTGCT GACAAGTTTG AGGTGTCTGC    4560
AGATAGTTCT ACCAGTAAAA ATAAAGAACC AGGAGTGGAA AGGTCATCCC CTTCTAAATG    4620
CCCATCATTA GATGATAGGT GGTACATGCA CAGTTGCTCT GGGAGTCTTC AGAATAGAAA    4680
CTACCCATCT CAAGAGGAGC TCATTAAGGT TGTTGATGTG GAGGAGCAAC AGCTGGAAGA    4740
GTCTGGGCCA CACGATTTGA CGGAAACATC TTACTTGCCA AGGCAAGATC TAGAGGGAAC    4800
CCCTTACCTG GAATCTGGAA TCAGCCTCTT CTCTGATGAC CCTGAATCTG ATCCTTCTGA    4860
AGACAGAGCC CCAGAGTCAG CTCGTGTTGG CAACATACCA TCTTCAACCT CTGCATTGAA    4920
AGTTCCCCAA TTGAAAGTTG CAGAATCTGC CCAGAGTCCA GCTGCTGCTC ATACTACTGA    4980
TACTGCTGGG TATAATGCAA TGGAAGAAAG TGTGAGCAGG GAGAAGCCAG AATTGACAGC    5040
TTCAACAGAA AGGGTCAACA AAGAATGTC CATGGTGGTG TCTGGCCTGA CCCCAGAAGA    5100
ATTTATGCTC GTGTACAAGT TTGCCAGAAA ACACCACATC ACTTTAACTA ATCTAATTAC    5160
TGAAGAGACT ACTCATGTTG TTATGAAAAC AGATGCTGAG TTTGTGTGTG AACGGACACT    5220
GAAATATTTT CTAGGAATTG CGGGAGGAAA ATGGGTAGTT AGCTATTTCT GGGTGACCCA    5280
GTCTATTAAA GAAAGAAAAA TGCTGAATGA GCATGATTTT GAAGTCAGAG GAGATGTGGT    5340
CAATGGAAGA AACCACCAAG GTCCAAAGCG AGCAAGAGAA TCCCAGGACA GAAAGATCTT    5400
CAGGGGGCTA GAAATCTGTT GCTATGGGCC CTTCACCAAC ATGCCCACAG ATCAACTGGA    5460
ATGGATGGTA CAGCTGTGTG GTGCTTCTGT GGTGAAGGAG CTTTCATCAT TCACCCTTGG    5520
CACAGGTGTC CACCCAATTG TGGTTGTGCA GCCAGATGCC TGGACAGAGG ACAATGGCTT    5580
CCATGCAATT GGGCAGATGT GTGAGGCACC TGTGGTGACC CGAGAGTGGG TGTTGGACAG    5640
TGTAGCACTC TACCAGTGCC AGGAGCTGGA CACCTACCTG ATACCCCAGA TCCCCCACAG    5700
CCACTACTGA                                                          5710
```

( 2 ) INFORMATION FOR SEQ ID NO:7:

( i ) SEQUENCE CHARACTERISTICS:
( A ) LENGTH: 5709 base pairs
( B ) TYPE: nucleic acid ( C ) STRANDEDNESS: double
( D ) TOPOLOGY: linear ( i i ) MOLECULE TYPE: cDNA ( x i ) SEQUENCE DESCRIPTION: SEQ ID NO:7:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |

| | | | | | |
|---|---|---|---|---|---|
| AGTTAACAAA | TGCACCTGGT | TCTTTTACTA | AGTGTTCAAA | TACCAGTGAA | CTTAAAGAAT 2280 |
| TTGTCAATCC | TAGCCTTCCA | AGAGAAGAAA | AAGAAGAGAA | ACTAGAAACA | GTTAAAGTGT 2340 |
| CTAATAATGC | TGAAGACCCC | AAAGATCTCA | TGTTAAGTGG | AGAAAGGGTT | TTGCAAACTG 2400 |
| AAAGATCTGT | AGAGTAGCAG | TATTTCATTG | GTACCTGGTA | CTGATTATGG | CACTCAGGAA 2460 |
| AGTATCTCGT | TACTGGAAGT | TAGCACTCTA | GGGAAGGCAA | AAACAGAACC | AAATAAATGT 2520 |
| GTGAGTCAGT | GTGCAGCATT | TGAAAACCCC | AAGGGACTAA | TTCATGGTTG | TTCCAAAGAT 2580 |
| AATAGAAATG | ACACAGAAGG | CTTTAAGTAT | CCATTGGGAC | ATGAAGTTAA | CCACAGTCGG 2640 |
| GAAACAAGCA | TAGAAATGGA | AGAAAGTGAA | CTTGATGCTC | AGTATTTGCA | GAATACATTC 2700 |
| AAGGTTTCAA | AGCGCCAGTC | ATTTGCTCCG | TTTTCAAATC | CAGGAAATGC | AGAAGAGGAA 2760 |
| TGTGCAACAT | TCTCTGCCCA | CTCTGGGTCC | TTAAAGAAAC | AAAGTCCAAA | AGTCACTTTT 2820 |
| GAATGTGAAC | AAAAGGAAGA | AAATCAAGGA | AAGAATGAGT | CTAATATCAA | GCCTGTACAG 2880 |
| ACAGTTAATA | TCACTGCAGG | CTTTCCTGTG | GTTGGTCAGA | AAGATAAGCC | AGTTGATAAT 2940 |
| GCCAAATGTA | GTATCAAGG | AGGCTCTAGG | TTTTGTCTAT | CATCTCAGTT | CAGAGGCAAC 3000 |
| GAAACTGGAC | TCATTACTCC | AAATAAACAT | GGACTTTTAC | AAAACCCATA | TCGTATACCA 3060 |
| CCACTTTTTC | CCATCAAGTC | ATTTGTTAAA | ACTAAATGTA | AGAAAATCT | GCTAGAGGAA 3120 |
| AACTTTGAGG | AACATTCAAT | GTCACCTGAA | AGAGAAATGG | GAAATGAGAA | CATTCCAAGT 3180 |
| ACAGTGAGCA | CAATTAGCCG | TAATAACATT | AGAGAAAATG | TTTTTAAAGA | AGCCAGCTCA 3240 |
| AGCAATATTA | ATGAAGTAGG | TTCCAGTACT | AATGAAGTGG | GCTCCAGTAT | TAATGAAATA 3300 |
| GGTTCCAGTG | ATGAAAACAT | TCAAGCAGAA | CTAGGTAGAA | ACAGAGGGCC | AAAATTGAAT 3360 |
| GCTATGCTTA | GATTAGGGGT | TTTGCAACCT | GAGGTCTATA | AACAAAGTCT | TCCTGGAAGT 3420 |
| AATTGTAAGC | ATCCTGAAAT | AAAAAAGCAA | GAATATGAAG | AAGTAGTTCA | GACTGTTAAT 3480 |
| ACAGATTTCT | CTCCATATCT | GATTTCAGAT | AACTTAGAAC | AGCCTATGGG | AAGTAGTCAT 3540 |
| GCATCTCAGG | TTTGTTCTGA | GACACCTGAT | GACCTGTTAG | ATGATGGTGA | AATAAAGGAA 3600 |
| GATACTAGTT | TTGCTGAAAA | TGACATTAAG | GAAAGTTCTG | CTGTTTTTAG | CAAAAGCGTC 3660 |
| CAGAAAGGAG | AGCTTAGCAG | GAGTCCTAGC | CCTTTCACCC | ATACACATTT | GGCTCAGGGT 3720 |
| TACCGAAGAG | GGGCCAAGAA | ATTAGAGTCC | TCAGAAGAGA | ACTTATCTAG | TGAGGATGAA 3780 |
| GAGCTTCCCT | GCTTCCAACA | CTTGTTATTT | GGTAAAGTAA | ACAATATACC | TTCTCAGTCT 3840 |
| ACTAGGCATA | GCACCGTTGC | TACCGAGTGT | CTGTCTAAGA | ACACAGAGGA | GAATTTATTA 3900 |
| TCATTGAAGA | ATAGCTTAAA | TGACTGCAGT | AACCAGGTAA | TATTGGCAAA | GGCATCTCAG 3960 |
| GAACATCACC | TTAGTGAGGA | AACAAAATGT | TCTGCTAGCT | TGTTTTCTTC | ACAGTGCAGT 4020 |
| GAATTGGAAG | ACTTGACTGC | AAATACAAAC | ACCCAGGATC | CTTTCTTGAT | TGGTTCTTCC 4080 |
| AAACAAATGA | GGCATCAGTC | TGAAAGCCAG | GGAGTTGGTC | TGAGTGACAA | GGAATTGGTT 4140 |
| TCAGATGATG | AAGAAGAGG | AACGGGCTTG | GAAGAAAATA | ATCAAGAAGA | GCAAAGCATG 4200 |
| GATTCAAACT | TAGGTGAAGC | AGCATCTGGG | TGTGAGAGTG | AAACAAGCGT | CTCTGAAGAC 4260 |
| TGCTCAGGGC | TATCCTCTCA | GAGTGACATT | TTAACCACTC | AGCAGAGGGA | TACCATGCAA 4320 |
| CATAACCTGA | TAAAGCTCCA | GCAGGAAATG | GCTGAACTAG | AAGCTGTGTT | AGAACAGCAT 4380 |
| GGGAGCCAGC | CTTCTAACAG | CTACCCTTCC | ATCATAAGTG | ACTCTTCTGC | CCTTGAGGAC 4440 |
| CTGCGAAATC | CAGAACAAAG | CACATCAGAA | AAAGCAGTAT | TAACTTCACA | GAAAAGTAGT 4500 |
| GAATACCCTA | TAAGCCAGAA | TCCAGAAGGC | CTTTCTGCTG | ACAAGTTTGA | GGTGTCTGCA 4560 |
| GATAGTTCTA | CCAGTAAAAA | TAAAGAACCA | GGAGTGGAAA | GGTCATCCCC | TTCTAAATGC 4620 |

-continued

| | | | | | |
|---|---|---|---|---|---|
| CCATCATTAG | ATGATAGGTG | GTACATGCAC | AGTTGCTCTG | GGAGTCTTCA | GAATAGAAAC | 4680
| TACCCATCTC | AAGAGGAGCT | CATTAAGGTT | GTTGATGTGG | AGGAGCAACA | GCTGGAAGAG | 4740
| TCTGGGCCAC | ACGATTTGAC | GGAAACATCT | TACTTGCCAA | GGCAAGATCT | AGAGGGAACC | 4800
| CCTTACCTGG | AATCTGGAAT | CAGCCTCTTC | TCTGATGACC | CTGAATCTGA | TCCTTCTGAA | 4860
| GACAGAGCCC | CAGAGTCAGC | TCGTGTTGGC | AACATACCAT | CTTCAACCTC | TGCATTGAAA | 4920
| GTTCCCCAAT | TGAAAGTTGC | AGAATCTGCC | CAGAGTCCAG | CTGCTGCTCA | TACTACTGAT | 4980
| ACTGCTGGGT | ATAATGCAAT | GGAAGAAAGT | GTGAGCAGGG | AGAAGCCAGA | ATTGACAGCT | 5040
| TCAACAGAAA | GGGTCAACAA | AAGAATGTCC | ATGGTGGTGT | CTGGCCTGAC | CCCAGAAGAA | 5100
| TTTATGCTCG | TGTACAAGTT | TGCCAGAAAA | CACCACATCA | CTTTAACTAA | TCTAATTACT | 5160
| GAAGAGACTA | CTCATGTTGT | TATGAAAACA | GATGCTGAGT | TTGTGTGTGA | ACGGACACTG | 5220
| AAATATTTTC | TAGGAATTGC | GGGAGGAAAA | TGGGTAGTTA | GCTATTTCTG | GGTGACCCAG | 5280
| TCTATTAAAG | AAAGAAAAAT | GCTGAATGAG | CATGATTTTG | AAGTCAGAGG | AGATGTGGTC | 5340
| AATGGAAGAA | ACCACCAAGG | TCCAAAGCGA | GCAAGAGAAT | CCCAGGACAG | AAAGATCTTC | 5400
| AGGGGCTAG | AAATCTGTTG | CTATGGGCCC | TTCACCAACA | TGCCCACAGA | TCAACTGGAA | 5460
| TGGATGGTAC | AGCTGTGTGG | TGCTTCTGTG | GTGAAGGAGC | TTTCATCATT | CACCCTTGGC | 5520
| ACAGGTGTCC | ACCCAATTGT | GGTTGTGCAG | CCAGATGCCT | GGACAGAGGA | CAATGGCTTC | 5580
| CATGCAATTG | GGCAGATGTG | TGAGGCACCT | GTGGTGACCC | GAGAGTGGGT | GTTGGACAGT | 5640
| GTAGCACTCT | ACCAGTGCCA | GGAGCTGGAC | ACCTACCTGA | TACCCAGAT | CCCCCACAGC | 5700
| CACTACTGA | | | | | | 5709

( 2 ) INFORMATION FOR SEQ ID NO:8:

( i ) SEQUENCE CHARACTERISTICS:
        ( A ) LENGTH: 5709 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60
| CCTGCGCTCA | GGAGGCCTTC | ACCCTCTGCT | CTGGGTAAAG | TTCATTGGAA | CAGAAAGAAA | 120
| TGGATTTATC | TGCTCTTCGC | GTTGAAGAAG | TACAAAATGT | CATTAATGCT | ATGCAGAAAA | 180
| TCTTAGAGTG | TCCCATCTGT | CTGGAGTTGA | TCAAGGAACC | TGTCTCCACA | AAGTGTGACC | 240
| ACATATTTTG | CAAATTTTGC | ATGCTGAAAC | TTCTCAACCA | GAAGAAAGGG | CCTTCACAGT | 300
| GTCCTTTATG | TAAGAATGAT | ATAACCAAAA | GGAGCCTACA | AGAAAGTACG | AGATTTAGTC | 360
| AACTTGTTGA | AGAGCTATTG | AAAATCATTT | GTGCTTTTCA | GCTTGACACA | GGTTTGGAGT | 420
| ATGCAAACAG | CTATAATTTT | GCAAAAAAGG | AAAATAACTC | TCCTGAACAT | CTAAAAGATG | 480
| AAGTTTCTAT | CATCCAAAGT | ATGGGCTACA | GAAACCGTGC | CAAAAGACTT | CTACAGAGTG | 540
| AACCCGAAAA | TCCTTCCTTG | CAGGAAACCA | GTCTCAGTGT | CCAACTCTCT | AACCTTGGAA | 600
| CTGTGAGAAC | TCTGAGGACA | AAGCAGCGGA | TACAACCTCA | AAAGACGTCT | GTCTACATTG | 660
| AATTGGGATC | TGATTCTTCT | GAAGATACCG | TTAATAAGGC | AACTTATTGC | AGTGTGGGAG | 720
| ATCAAGAATT | GTTACAAATC | ACCCCTCAAG | GAACCAGGGA | TGAAATCAGT | TTGGATTCTG | 780
| CAAAAAAGGC | TGCTTGTGAA | TTTTCTGAGA | CGGATGTAAC | AAATACTGAA | CATCATCAAC | 840

| | | | | | |
|---|---|---|---|---|---|
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAC | AAAGTCCAAA | AGTCACTTTT | 2820 |
| GAATGTGAAC | AAAAGGAAGA | AAATCAAGGA | AGAATGAGT | CTAATATCAA | GCCTGTACAG | 2880 |
| ACAGTTAATA | TCACTGCAGG | CTTTCCTGTG | GTTGGTCAGA | AAGATAAGCC | AGTTGATAAT | 2940 |
| GCCAAATGTA | GTATCAAAGG | AGGCTCTAGG | TTTTGTCTAT | CATCTCAGTT | CAGAGGCAAC | 3000 |
| GAAACTGGAC | TCATTACTCC | AAATAAACAT | GGACTTTTAC | AAAACCCATA | TCGTATACCA | 3060 |
| CCACTTTTTC | CCATCAAGTC | ATTTGTTAAA | ACTAAATGTA | AGAAAAATCT | GCTAGAGGAA | 3120 |
| AACTTTGAGG | AACATTCAAT | GTCACCTGAA | AGAGAAATGG | GAAATGAGAA | CATTCCAAGT | 3180 |
| ACAGTGAGCA | CAATTAGCCG | TAATAACATT | AGAGAAAATG | TTTTTAAAGA | AGCCAGCTCA | 3240 |

| | | | | | | |
|---|---|---|---|---|---|---|
| AGCAATATTA | ATGAAGTAGG | TTCCAGTACT | AATGAAGTGG | GCTCCAGTAT | TAATGAAATA | 3300 |
| GGTTCCAGTG | ATGAAAACAT | TCAAGCAGAA | CTAGGTAGAA | ACAGAGGGCC | AAAATTGAAT | 3360 |
| GCTATGCTTA | GATTAGGGGT | TTTGCAACCT | GAGGTCTATA | AACAAAGTCT | TCCTGGAAGT | 3420 |
| AATTGTAAGC | ATCCTGAAAT | AAAAAAGCAA | GAATATGAAG | AAGTAGTTCA | GACTGTTAAT | 3480 |
| ACAGATTTCT | CTCCATATCT | GATTTCAGAT | AACTTAGAAC | AGCCTATGGG | AAGTAGTCAT | 3540 |
| GCATCTCAGG | TTTGTTCTGA | GACACCTGAT | GACCTGTTAG | ATGATGGTGA | AATAAAGGAA | 3600 |
| GATACTAGTT | TTGCTGAAAA | TGACATTAAG | GAAAGTTCTG | CTGTTTTTAG | CAAAAGCGTC | 3660 |
| CAGAAAGGAG | AGCTTAGCAG | GAGTCCTAGC | CCTTTCACCC | ATACACATTT | GGCTCAGGGT | 3720 |
| TACCGAAGAG | GGGCCAAGAA | ATTAGAGTCC | TCAGAAGAGA | ACTTATCTAG | TGAGGATGAA | 3780 |
| GAGCTTCCCT | GCTTCCAACA | CTTGTTATTT | GGTAAAGTAA | ACAATATACC | TTCTCAGTCT | 3840 |
| ACTAGGCATA | GCACCGTTGC | TACCGAGTGT | CTGTCTAAGA | ACACAGAGGA | GAATTTATTA | 3900 |
| TCATTGAAGA | ATAGCTAAA | TGACTGCAGT | AACCAGGTAA | TATTGGCAAA | GGCATCTCAG | 3960 |
| GAACATCACC | TTAGTGAGGA | AACAAAATGT | TCTGCTAGCT | TGTTTTCTTC | ACAGTGCAGT | 4020 |
| GAATTGGAAG | ACTTGACTGC | AAATACAAAC | ACCCAGGATC | CTTTCTTGAT | TGGTTCTTCC | 4080 |
| AAACAAATGA | GGCATCAGTC | TGAAAGCCAG | GGAGTTGGTC | TGAGTGACAA | GGAATTGGTT | 4140 |
| TCAGATGATG | AAGAAAGAGG | AACGGGCTTG | GAAGAAAATA | ATCAAGAAGA | GCAAAGCATG | 4200 |
| GATTCAAACT | TAGGTGAAGC | AGCATCTGGG | TGTGAGAGTG | AAACAAGCGT | CTCTGAAGAC | 4260 |
| TGCTCAGGGC | TATCCTCTCA | GAGTGACATT | TTAACCACTC | AGCAGAGGGA | TACCATGCAA | 4320 |
| CATAACCTGA | TAAAGCTCCA | GCAGGAAATG | GCTGAACTAG | AAGCTGTGTT | AGAACAGCAT | 4380 |
| GGGAGCCAGC | CTTCTAACAG | CTACCCTTCC | ATCATAAGTG | ACTCTTCTGC | CCTTGAGGAC | 4440 |
| CTGCGAAATC | CAGAACAAAG | CACATCAGAA | AAAGCAGTAT | TAACTTCACA | GAAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | CAGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AAGAATGTCC | ATGGTGGTGT | CTGGCCTGAC | CCCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |

| | | | | | | |
|---|---|---|---|---|---|---|
| GTAGCACTCT | ACCAGTGCCA | GGAGCTGGAC | ACCTACCTGA | TACCCCAGAT | CCCCCACAGC | 5700 |
| CACTACTGA | | | | | | 5709 |

( 2 ) INFORMATION FOR SEQ ID NO:9:

( i ) SEQUENCE CHARACTERISTICS:
        ( A ) LENGTH: 5709 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |

| | | | | | |
|---|---|---|---|---|---|
| ACAATTCAAA | AGCACCTAAA | AAGAATAGGC | TGAGGAGGAA | GTCTTCTACC | AGGCATATTC | 1980
| ATGCGCTTGA | ACTAGTAGTC | AGTAGAAATC | TAAGCCCACC | TAATTGTACT | GAATTGCAAA | 2040
| TTGATAGTTG | TTCTAGCAGT | GAAGAGATAA | AGAAAAAAAA | GTACAACCAA | ATGCCAGTCA | 2100
| GGCACAGCAG | AAACCTACAA | CTCATGGAAG | GTAAAGAACC | TGCAACTGGA | GCCAAGAAGA | 2160
| GTAACAAGCC | AAATGAACAG | ACAAGTAAAA | GACATGACAG | CGATACTTTC | CCAGAGCTGA | 2220
| AGTTAACAAA | TGCACCTGGT | TCTTTTACTA | AGTGTTCAAA | TACCAGTGAA | CTTAAAGAAT | 2280
| TTGTCAATCC | TAGCCTTCCA | AGAGAAGAAA | AAGAAGAGAA | ACTAGAAACA | GTTAAAGTGT | 2340
| CTAATAATGC | TGAAGACCCC | AAAGATCTCA | TGTTAAGTGG | AGAAAGGGTT | TTGCAAACTG | 2400
| AAAGATCTGT | AGAGAGTAGC | AGTATTTCAT | TGGTACCTGG | TACTGATTAT | GGCACTCAGG | 2460
| AAAGTATCTC | GTTACTGGAA | GTTAGCACTC | TAGGGAAGGC | AAAAACAGAA | CCAAATAAAT | 2520
| GTGTGAGTCA | GTGTGCAGCA | TTTGAAAACC | CCAAGGGACT | AATTCATGGT | TGTTCCAAAG | 2580
| ATAATAGAAA | TGACACAGAA | GGCTTTAAGT | ATCCATTGGG | ACATGAAGTT | AACCACAGTC | 2640
| GGGAAACAAG | CATAGAAATG | GAAGAAAGTG | AACTTGATGC | TCAGTATTTG | CAGAATACAT | 2700
| TCAAGGTTTC | AAAGCGCCAG | TCATTTGCTC | CGTTTTCAAA | TCCAGGAAAT | GCAGAAGAGG | 2760
| AATGTGCAAC | ATTCTCTGCC | CACTCTGGGT | CCTTAAAGAA | ACAAAGTCCA | AAAGTCACTT | 2820
| TTGAATGTGA | ACAAAAGGAA | GAAAATCAAG | GAAAGAATGA | GTAATATCAA | GCCTGTACAG | 2880
| ACAGTTAATA | TCACTGCAGG | CTTTCCTGTG | GTTGGTCAGA | AAGATAAGCC | AGTTGATAAT | 2940
| GCCAAATGTA | GTATCAAAGG | AGGCTCTAGG | TTTTGTCTAT | CATCTCAGTT | CAGAGGCAAC | 3000
| GAAACTGGAC | TCATTACTCC | AAATAAACAT | GGACTTTTAC | AAAACCCATA | TCGTATACCA | 3060
| CCACTTTTTC | CCATCAAGTC | ATTTGTTAAA | ACTAAATGTA | AGAAAATCT | GCTAGAGGAA | 3120
| AACTTTGAGG | AACATTCAAT | GTCACCTGAA | AGAGAAATGG | GAAATGAGAA | CATTCCAAGT | 3180
| ACAGTGAGCA | CAATTAGCCG | TAATAACATT | AGAGAAAATG | TTTTTAAAGA | AGCCAGCTCA | 3240
| AGCAATATTA | ATGAAGTAGG | TTCCAGTACT | AATGAAGTGG | GCTCCAGTAT | TAATGAAATA | 3300
| GGTTCCAGTG | ATGAAAACAT | TCAAGCAGAA | CTAGGTAGAA | ACAGAGGGCC | AAAATTGAAT | 3360
| GCTATGCTTA | GATTAGGGGT | TTTGCAACCT | GAGGTCTATA | AACAAAGTCT | TCCTGGAAGT | 3420
| AATTGTAAGC | ATCCTGAAAT | AAAAAAGCAA | GAATATGAAG | AAGTAGTTCA | GACTGTTAAT | 3480
| ACAGATTTCT | CTCCATATCT | GATTTCAGAT | AACTTAGAAC | AGCCTATGGG | AAGTAGTCAT | 3540
| GCATCTCAGG | TTTGTTCTGA | GACACCTGAT | GACCTGTTAG | ATGATGGTGA | AATAAAGGAA | 3600
| GATACTAGTT | TTGCTGAAAA | TGACATTAAG | GAAAGTTCTG | CTGTTTTTAG | CAAAAGCGTC | 3660
| CAGAAAGGAG | AGCTTAGCAG | GAGTCCTAGC | CCTTTCACCC | ATACACATTT | GGCTCAGGGT | 3720
| TACCGAAGAG | GGGCCAAGAA | ATTAGAGTCC | TCAGAAGAGA | ACTTATCTAG | TGAGGATGAA | 3780
| GAGCTTCCCT | GCTTCCAACA | CTTGTTATTT | GGTAAAGTAA | ACAATATACC | TTCTCAGTCT | 3840
| ACTAGGCATA | GCACCGTTGC | TACCGAGTGT | CTGTCTAAGA | ACACAGAGGA | GAATTTATTA | 3900
| TCATTGAAGA | ATAGCTTAAA | TGACTGCAGT | AACCAGGTAA | TATTGGCAAA | GGCATCTCAG | 3960
| GAACATCACC | TTAGTGAGGA | AACAAAATGT | TCTGCTAGCT | TGTTTTCTTC | ACAGTGCAGT | 4020
| GAATTGGAAG | ACTTGACTGC | AAATACAAAC | ACCCAGGATC | CTTTCTTGAT | TGGTTCTTCC | 4080
| AAACAAATGA | GGCATCAGTC | TGAAAGCCAG | GGAGTTGGTC | TGAGTGACAA | GGAATTGGTT | 4140
| TCAGATGATG | AAGAAAGAGG | AACGGGCTTG | GAAGAAAATA | ATCAAGAAGA | GCAAAGCATG | 4200
| GATTCAAACT | TAGGTGAAGC | AGCATCTGGG | TGTGAGAGTG | AAACAAGCGT | CTCTGAAGAC | 4260
| TGCTCAGGGC | TATCCTCTCA | GAGTGACATT | TTAACCACTC | AGCAGAGGGA | TACCATGCAA | 4320

| | | | | | | |
|---|---|---|---|---|---|---|
| CATAACCTGA | TAAAGCTCCA | GCAGGAAATG | GCTGAACTAG | AAGCTGTGTT | AGAACAGCAT | 4380 |
| GGGAGCCAGC | CTTCTAACAG | CTACCCTTCC | ATCATAAGTG | ACTCTTCTGC | CCTTGAGGAC | 4440 |
| CTGCGAAATC | CAGAACAAAG | CACATCAGAA | AAAGCAGTAT | TAACTTCACA | GAAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | AGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AAGAATGTCC | ATGGTGGTGT | CTGGCCTGAC | CCCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |
| GTAGCACTCT | ACCAGTGCCA | GGAGCTGGAC | ACCTACCTGA | TACCCAGAT | CCCCCACAGC | 5700 |
| CACTACTGA | | | | | | 5709 |

( 2 ) INFORMATION FOR SEQ ID NO:10:

( i ) SEQUENCE CHARACTERISTICS:
( A ) LENGTH: 5711 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:10:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |

| | | | | | | |
|---|---|---|---|---|---|---|
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | GGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |

| | | | | | |
|---|---|---|---|---|---|
| ATGCCAAATG | TAGTATCAAA | GGAGGCTCTA | GGTTTTGTCT | ATCATCTCAG | TTCAGAGGCA | 3000
| ACGAAACTGG | ACTCATTACT | CCAAATAAAC | ATGGACTTTT | ACAAACCCA | TATCGTATAC | 3060
| CACCACTTTT | TCCCATCAAG | TCATTTGTTA | AAACTAAATG | TAAGAAAAT | CTGCTAGAGG | 3120
| AAAACTTTGA | GGAACATTCA | ATGTCACCTG | AAAGAGAAAT | GGGAAATGAG | AACATTCCAA | 3180
| GTACAGTGAG | CACAATTAGC | CGTAATAACA | TTAGAGAAAA | TGTTTTTAAA | GAAGCCAGCT | 3240
| CAAGCAATAT | TAATGAAGTA | GGTTCCAGTA | CTAATGAAGT | GGGCTCCAGT | ATTAATGAAA | 3300
| TAGGTTCCAG | TGATGAAAAC | ATTCAAGCAG | AACTAGGTAG | AAACAGAGGG | CCAAAATTGA | 3360
| ATGCTATGCT | TAGATTAGGG | GTTTTGCAAC | CTGAGGTCTA | TAAACAAAGT | CTTCCTGGAA | 3420
| GTAATTGTAA | GCATCCTGAA | ATAAAAAGC | AAGAATATGA | AGAAGTAGTT | CAGACTGTTA | 3480
| ATACAGATTT | CTCTCCATAT | CTGATTTCAG | ATAACTTAGA | ACAGCCTATG | GGAAGTAGTC | 3540
| ATGCATCTCA | GGTTTGTTCT | GAGACACCTG | ATGACCTGTT | AGATGATGGT | GAAATAAAGG | 3600
| AAGATACTAG | TTTTGCTGAA | AATGACATTA | AGGAAAGTTC | TGCTGTTTTT | AGCAAAAGCG | 3660
| TCCAGAAAGG | AGAGCTTAGC | AGGAGTCCTA | GCCCTTTCAC | CCATACACAT | TTGGCTCAGG | 3720
| GTTACTGAAG | AGGGGCCAAG | AAATTAGAGT | CCTCAGAAGA | GAACTTATCT | AGTGAGGATG | 3780
| AAGAGCTTCC | CTGCTTCCAA | CACTTGTTAT | TTGGTAAAGT | AAACAATATA | CCTTCTCAGT | 3840
| CTACTAGGCA | TAGCACCGTT | GCTACCGAGT | GTCTGTCTAA | GAACACAGAG | GAGAATTTAT | 3900
| TATCATTGAA | GAATAGCTTA | AATGACTGCA | GTAACCAGGT | AATATTGGCA | AAGGCATCTC | 3960
| AGGAACATCA | CCTTAGTGAG | GAAACAAAAT | GTTCTGCTAG | CTTGTTTTCT | TCACAGTGCA | 4020
| GTGAATTGGA | AGACTTGACT | GCAAATACAA | ACACCCAGGA | TCCTTTCTTG | ATTGGTTCTT | 4080
| CCAAACAAAT | GAGGCATCAG | TCTGAAAGCC | AGGGAGTTGG | TCTGAGTGAC | AAGGAATTGG | 4140
| TTTCAGATGA | TGAAGAAAGA | GGAACGGGCT | TGGAAGAAAA | TAATCAAGAA | GAGCAAAGCA | 4200
| TGGATTCAAA | CTTAGGTGAA | GCAGCATCTG | GGTGTGAGAG | TGAAACAAGC | GTCTCTGAAG | 4260
| ACTGCTCAGG | GCTATCCTCT | CAGAGTGACA | TTTTAACCAC | TCAGCAGAGG | GATACCATGC | 4320
| AACATAACCT | GATAAAGCTC | CAGCAGGAAA | TGGCTGAACT | AGAAGCTGTG | TTAGAACAGC | 4380
| ATGGGAGCCA | GCCTTCTAAC | AGCTACCCTT | CCATCATAAG | TGACTCTTCT | GCCCTTGAGG | 4440
| ACCTGCGAAA | TCCAGAACAA | AGCACATCAG | AAAAAGCAGT | ATTAACTTCA | CAGAAAAGTA | 4500
| GTGAATACCC | TATAAGCCAG | AATCCAGAAG | GCCTTTCTGC | TGACAAGTTT | GAGGTGTCTG | 4560
| CAGATAGTTC | TACCAGTAAA | AATAAAGAAC | CAGGAGTGGA | AAGGTCATCC | CCTTCTAAAT | 4620
| GCCCATCATT | AGATGATAGG | TGGTACATGC | ACAGTTGCTC | TGGGAGTCTT | CAGAATAGAA | 4680
| ACTACCCATC | TCAAGAGGAG | CTCATTAAGG | TTGTTGATGT | GGAGGAGCAA | CAGCTGGAAG | 4740
| AGTCTGGGCC | ACACGATTTG | ACGGAAACAT | CTTACTTGCC | AAGGCAAGAT | CTAGAGGGAA | 4800
| CCCCTTACCT | GGAATCTGGA | ATCAGCCTCT | TCTCTGATGA | CCCTGAATCT | GATCCTTCTG | 4860
| AAGACAGAGC | CCCAGAGTCA | GCTCGTGTTG | GCAACATACC | ATCTTCAACC | TCTGCATTGA | 4920
| AAGTTCCCCA | ATTGAAAGTT | GCAGAATCTG | CCCAGAGTCC | AGCTGCTGCT | CATACTACTG | 4980
| ATACTGCTGG | GTATAATGCA | ATGGAAGAAA | GTGTGAGCAG | GGAGAAGCCA | GAATTGACAG | 5040
| CTTCAACAGA | AAGGGTCAAC | AAAAGAATGT | CCATGGTGGT | GTCTGGCCTG | ACCCCAGAAG | 5100
| AATTTATGCT | CGTGTACAAG | TTTGCCAGAA | ACACCACAT | CACTTTAACT | AATCTAATTA | 5160
| CTGAAGAGAC | TACTCATGTT | GTTATGAAAA | CAGATGCTGA | GTTTGTGTGT | GAACGGACAC | 5220
| TGAAATATTT | TCTAGGAATT | GCGGGAGGAA | AATGGGTAGT | TAGCTATTTC | TGGGTGACCC | 5280
| AGTCTATTAA | AGAAAGAAAA | ATGCTGAATG | AGCATGATTT | TGAAGTCAGA | GGAGATGTGG | 5340

|              |              |              |              |              |              |      |
|---|---|---|---|---|---|---|
| TCAATGGAAG | AAACCACCAA | GGTCCAAAGC | GAGCAAGAGA | ATCCCAGGAC | AGAAAGATCT | 5400 |
| TCAGGGGGCT | AGAAATCTGT | TGCTATGGGC | CCTTCACCAA | CATGCCCACA | GATCAACTGG | 5460 |
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCCAG | ATCCCCCACA | 5700 |
| GCCACTACTG | A | | | | | 5711 |

(2) INFORMATION FOR SEQ ID NO:11:

(i) SEQUENCE CHARACTERISTICS:
        (A) LENGTH: 5707 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

|              |              |              |              |              |              |      |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |

```
AATTAAAGCG  TAAAAGGAGA  CCTACATCAG  GCCTTCATCC  TGAGGATTTT  ATCAAGAAAG    1680
CAGATTTGGC  AGTTCAAAAG  ACTCCTGAAA  TGATAAATCA  GGGAACTAAC  CAAACGGAGC    1740
AGAATGGTCA  AGTGATGAAT  ATTACTAATA  GTGGTCATGA  GAATAAAACA  AAAGGTGATT    1800
CTATTCAGAA  TGAGAAAAAT  CCTAACCCAA  TAGAATCACT  CGAAAAGAA   TCTGCTTTCA    1860
AAACGAAAGC  TGAACCTATA  AGCAGCAGTA  TAAGCAATAT  GGAACTCGAA  TTAAATATCC    1920
ACAATTCAAA  AGCACCTAAA  AAGAATAGGC  TGAGGAGGAA  GTCTTCTACC  AGGCATATTC    1980
ATGCGCTTGA  ACTAGTAGTC  AGTAGAAATC  TAAGCCCACC  TAATTGTACT  GAATTGCAAA    2040
TTGATAGTTG  TTCTAGCAGT  GAAGAGATAA  AGAAAAAAA   GTACAACCAA  ATGCCAGTCA    2100
GGCACAGCAG  AAACCTACAA  CTCATGGAAG  GTAAAGAACC  TGCAACTGGA  GCCAAGAAGA    2160
GTAACAAGCC  AAATGAACAG  ACAAGTAAAA  GACATGACAG  CGATACTTTC  CCAGAGCTGA    2220
AGTTAACAAA  TGCACCTGGT  TCTTTTACTA  AGTGTTCAAA  TACCAGTGAA  CTTAAAGAAT    2280
TTGTCAATCC  TAGCCTTCCA  AGAGAAGAAA  AAGAAGAGAA  ACTAGAAACA  GTTAAAGTGT    2340
CTAATAATGC  TGAAGACCCC  AAAGATCTCA  TGTTAAGTGG  AGAAAGGGTT  TTGCAAACTG    2400
AAAGATCTGT  AGAGAGTAGC  AGTATTTCAT  TGGTACCTGG  TACTGATTAT  GGCACTCAGG    2460
AAAGTATCTC  GTTACTGGAA  GTTAGCACTC  TAGGGAAGGC  AAAAACAGAA  CCAAATAAAT    2520
GTGTGAGTCA  GTGTGCAGCA  TTTGAAAACC  CCAAGGGACT  AATTCATGGT  TGTTCCAAAG    2580
ATAATAGAAA  TGACACAGAA  GGCTTTAAGT  ATCCATTGGG  ACATGAAGTT  AACCACAGTC    2640
GGGAAACAAG  CATAGAAATG  GAAGAAAGTG  AACTTGATGC  TCAGTATTTG  CAGAATACAT    2700
TCAAGGTTTC  AAAGCGCCAG  TCATTGCTC   CGTTTTCAAA  TCCAGGAAAT  GCAGAAGAGG    2760
AATGTGCAAC  ATTCTCTGCC  CACTCTGGGT  CCTTAAAGAA  ACAAGTCCA   AAAGTCACTT    2820
TTGAATGTGA  ACAAAGGAA   GAAAATCAAG  GAAGAATGA   GTCTAATATC  AAGCCTGTAC    2880
AGACAGTTAA  TATCACTGCA  GGCTTTCCTG  TGGTTGGTCA  GAAAGATAAG  CCAGTTGATA    2940
ATGCCAAATG  TAGTATCAAA  GGAGGCTCTA  GGTTTTGTCT  ATCATCTCAG  TTCAGAGGCA    3000
ACGAAACTGG  ACTCATTACT  CCAAATAAAC  ATGGACTTTT  ACAAACCCA   TATCGTATAC    3060
CACCACTTTT  TCCCATCAAG  TCATTTGTTA  AAACTAAATG  TAAGAAAAAT  CTGCTAGAGG    3120
AAAACTTTGA  GGAACATTCA  ATGTCACCTG  AAAGAGAAAT  GGGAAATGAG  AACATTCCAA    3180
GTACAGTGAG  CACAATTAGC  CGTAATAACA  TTAGAGAAAA  TGTTTTTAAA  GAAGCCAGCT    3240
CAAGCAATAT  TAATGAAGTA  GGTTCCAGTA  CTAATGAAGT  GGGCTCCAGT  ATTAATGAAA    3300
TAGGTTCCAG  TGATGAAAAC  ATTCAAGCAG  AACTAGGTAG  AAACAGAGGG  CCAAAATTGA    3360
ATGCTATGCT  TAGATTAGGG  GTTTTGCAAC  CTGAGGTCTA  TAAACAAAGT  CTTCCTGGAA    3420
GTAATTGTAA  GCATCCTGAA  ATAAAAAGC   AAGAATATGA  AGAAGTAGTT  CAGACTGTTA    3480
ATACAGATTT  CTCTCCATAT  CTGATTTCAG  ATAACTTAGA  ACAGCCTATG  GGAAGTAGTC    3540
ATGCATCTCA  GGTTTGTTCT  GAGACACCTG  ATGACCTGTT  AGATGATGGT  GAAATAAAGG    3600
AAGATACTAG  TTTTGCTGAA  AATGACATTA  AGGAAAGTTC  TGCTGTTTTT  AGCAAAAGCG    3660
TCCAGAAAGG  AGAGCTTAGC  AGGAGTCCTA  GCCCTTTCAC  CCATACACAT  TTGGCTCAGG    3720
GTTACCGAAG  AGGGGCCAAG  AAATTAGAGT  CCTCAGAAGA  GAACTTATCT  AGTGAGGATG    3780
AAGAGCTTCC  CTGCTTCCAA  CACTTGTTAT  TTGGTAAAGT  AAACAATATA  CCTTCTCAGT    3840
CTACTAGGCA  TAGCACCGTT  GCTACCGAGT  GTCTGTCTAA  GAACACAGAG  GAGAATTTAT    3900
TATCATTGAA  GAATAGCTTA  AATGACTGCA  GTAACCAGGT  AATATTGGCA  AAGGCATCTC    3960
AGGAACATCA  CCTTAGTGAG  GAAACAAAAT  GTTCTGCTAG  CTTGTTTTCT  TCACAGTGCA    4020
```

| | | | | | |
|---|---|---|---|---|---|
|GTGAATTGGA|AGACTTGACT|GCAAATACAA|ACACCCAGGA|TCCTTTCTTG|ATTGGTTCTT|4080|
|CCAAACAAAT|GAGGCATCAG|TCTGAAAGCC|AGGGAGTTGG|TCTGAGTGAC|AAGGAATTGG|4140|
|TTTCAGATGA|TGAAGAAAGA|GGAACGGGCT|TGGAAGAAAA|TAAGAAGAGC|AAAGCATGGA|4200|
|TTCAAACTTA|GGTGAAGCAG|CATCTGGGTG|TGAGAGTGAA|ACAAGCGTCT|CTGAAGACTG|4260|
|CTCAGGGCTA|TCCTCTCAGA|GTGACATTTT|AACCACTCAG|CAGAGGGATA|CCATGCAACA|4320|
|TAACCTGATA|AAGCTCCAGC|AGGAAATGGC|TGAACTAGAA|GCTGTGTTAG|AACAGCATGG|4380|
|GAGCCAGCCT|TCTAACAGCT|ACCCTTCCAT|CATAAGTGAC|TCTTCTGCCC|TTGAGGACCT|4440|
|GCGAAATCCA|GAACAAAGCA|CATCAGAAAA|AGCAGTATTA|ACTTCACAGA|AAAGTAGTGA|4500|
|ATACCCTATA|AGCCAGAATC|CAGAAGGCCT|TTCTGCTGAC|AAGTTTGAGG|TGTCTGCAGA|4560|
|TAGTTCTACC|AGTAAAAATA|AAGAACCAGG|AGTGGAAAGG|TCATCCCCTT|CTAAATGCCC|4620|
|ATCATTAGAT|GATAGGTGGT|ACATGCACAG|TTGCTCTGGG|AGTCTTCAGA|ATAGAAACTA|4680|
|CCCATCTCAA|GAGGAGCTCA|TTAAGGTTGT|TGATGTGGAG|GAGCAACAGC|TGGAAGAGTC|4740|
|TGGGCCACAC|GATTTGACGG|AAACATCTTA|CTTGCCAAGG|CAAGATCTAG|AGGGAACCCC|4800|
|TTACCTGGAA|TCTGGAATCA|GCCTCTTCTC|TGATGACCCT|GAATCTGATC|CTTCTGAAGA|4860|
|CAGAGCCCCA|GAGTCAGCTC|GTGTTGGCAA|CATACCATCT|TCAACCTCTG|CATTGAAAGT|4920|
|TCCCCAATTG|AAAGTTGCAG|AATCTGCCCA|GAGTCCAGCT|GCTGCTCATA|CTACTGATAC|4980|
|TGCTGGGTAT|AATGCAATGG|AAGAAAGTGT|GAGCAGGGAG|AAGCCAGAAT|TGACAGCTTC|5040|
|AACAGAAAGG|GTCAACAAAA|GAATGTCCAT|GGTGGTGTCT|GGCCTGACCC|CAGAAGAATT|5100|
|TATGCTCGTG|TACAAGTTTG|CCAGAAAACA|CCACATCACT|TTAACTAATC|TAATTACTGA|5160|
|AGAGACTACT|CATGTTGTTA|TGAAAACAGA|TGCTGAGTTT|GTGTGTGAAC|GGACACTGAA|5220|
|ATATTTTCTA|GGAATTGCGG|GAGGAAAATG|GGTAGTTAGC|TATTTCTGGG|TGACCCAGTC|5280|
|TATTAAAGAA|AGAAAAATGC|TGAATGAGCA|TGATTTTGAA|GTCAGAGGAG|ATGTGGTCAA|5340|
|TGGAAGAAAC|CACCAAGGTC|CAAAGCGAGC|AAGAGAATCC|CAGGACAGAA|AGATCTTCAG|5400|
|GGGGCTAGAA|ATCTGTTGCT|ATGGGCCCTT|CACCAACATG|CCCACAGATC|AACTGGAATG|5460|
|GATGGTACAG|CTGTGTGGTG|CTTCTGTGGT|GAAGGAGCTT|TCATCATTCA|CCCTTGGCAC|5520|
|AGGTGTCCAC|CCAATTGTGG|TTGTGCAGCC|AGATGCCTGG|ACAGAGGACA|ATGGCTTCCA|5580|
|TGCAATTGGG|CAGATGTGTG|AGGCACCTGT|GGTGACCCGA|GAGTGGGTGT|TGGACAGTGT|5640|
|AGCACTCTAC|CAGTGCCAGG|AGCTGGACAC|CTACCTGATA|CCCCAGATCC|CCACAGCCA|5700|
|CTACTGA| | | | | |5707|

(2) INFORMATION FOR SEQ ID NO:12:

(i) SEQUENCE CHARACTERISTICS:
(A) LENGTH: 5712 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:12:

| | | | | | |
|---|---|---|---|---|---|
|AGCTCGCTGA|GACTTCCTGG|ACCCCGCACC|AGGCTGTGGG|GTTTCTCAGA|TAACTGGGCC|60|
|CCTGCGCTCA|GGAGGCCTTC|ACCCTCTGCT|CTGGGTAAAG|TTCATTGGAA|CAGAAAGAAA|120|
|TGGATTTATC|TGCTCTTCGC|GTTGAAGAAG|TACAAAATGT|CATTAATGCT|ATGCAGAAAA|180|
|TCTTAGAGTG|TCCCATCTGT|CTGGAGTTGA|TCAAGGAACC|TGTCTCCACA|AAGTGTGACC|240|

| | | | | | | |
|---|---|---|---|---|---|---|
| ACATATTTTG | CAAATTTTGC | ATGCTGAAAC | TTCTCAACCA | GAAGAAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAGG | AAAATAACTC | TCCTGAACAT | CTAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |

| | | | | | | |
|---|---|---|---|---|---|---|
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAGAATGA | GTCAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTTGTCT | ATCATCTCAG | TTCAGAGGCA | 3000 |
| ACGAAACTGG | ACTCATTACT | CCAAATAAAC | ATGGACTTTT | ACAAACCCA | TATCGTATAC | 3060 |
| CACCACTTTT | TCCCATCAAG | TCATTTGTTA | AAACTAAATG | TAAGAAAAT | CTGCTAGAGG | 3120 |
| AAAACTTTGA | GGAACATTCA | ATGTCACCTG | AAAGAGAAAT | GGGAAATGAG | AACATTCCAA | 3180 |
| GTACAGTGAG | CACAATTAGC | CGTAATAACA | TTAGAGAAAA | TGTTTTTAAA | GAAGCCAGCT | 3240 |
| CAAGCAATAT | TAATGAAGTA | GGTTCCAGTA | CTAATGAAGT | GGGCTCCAGT | ATTAATGAAA | 3300 |
| TAGGTTCCAG | TGATGAAAAC | ATTCAAGCAG | AACTAGGTAG | AAACAGAGGG | CCAAAATTGA | 3360 |
| ATGCTATGCT | TAGATTAGGG | GTTTTGCAAC | CTGAGGTCTA | TAAACAAAGT | CTTCCTGGAA | 3420 |
| GTAATTGTAA | GCATCCTGAA | ATAAAAAGC | AAGAATATGA | AGAAGTAGTT | CAGACTGTTA | 3480 |
| ATACAGATTT | CTCTCCATAT | CTGATTTCAG | ATAACTTAGA | ACAGCCTATG | GGAAGTAGTC | 3540 |
| ATGCATCTCA | GGTTTGTTCT | GAGACACCTG | ATGACCTGTT | AGATGATGGT | GAAATAAAGG | 3600 |
| AAGATACTAG | TTTTGCTGAA | AATGACATTA | AGGAAAGTTC | TGCTGTTTTT | AGCAAAAGCG | 3660 |
| TCCAGAAAGG | AGAGCTTAGC | AGGAGTCCTA | GCCCTTTCAC | CCATACACAT | TTGGCTCAGG | 3720 |
| GTTACCGAAG | AGGGGCCAAG | AAATTAGAGT | CCTCAGAAGA | GAACTTATCT | AGTGAGGATG | 3780 |
| AAGAGCTTCC | CTGCTTCCAA | CACTTGTTAT | TTGGTAAAGT | AAACAATATA | CCTTCTCAGT | 3840 |
| CTACTAGGCA | TAGCACCGTT | GCTACCGAGT | GTCTGTCTAA | GAACACAGAG | GAGAATTTAT | 3900 |
| TATCATTGAA | GAATAGCTTA | AATGACTGCA | GTAACCAGGT | AATATTGGCA | AAGGCATCTC | 3960 |
| AGGAACATCA | CCTTAGTGAG | GAAACAAAAT | GTTCTGCTAG | CTTGTTTTCT | TCACAGTGCA | 4020 |
| GTGAATTGGA | AGACTTGACT | GCAAATACAA | ACACCCAGGA | TCCTTTCTTG | ATTGGTTCTT | 4080 |
| CCAAACAAAT | GAGGCATCAG | TCTGAAAGCC | AGGGAGTTGG | TCTGAGTGAC | AAGGAATTGG | 4140 |
| TTTCAGATGA | TGAAGAAAGA | GGAACGGGCT | TGGAAGAAAA | TAATCAAGAA | GAGCAAAGCA | 4200 |
| TGGATTCAAA | CTTAGGTGAA | GCAGCATCTG | GGTGTGAGAG | TGAAACAAGC | GTCTCTGAAG | 4260 |
| ACTGCTCAGG | GCTATCCTCT | CAGAGTGACA | TTTTAACCAC | TCAGCAGAGG | GATACCATGC | 4320 |
| AACATAACCT | GATAAAGCTC | CAGCAGGAAA | TGGCTGAACT | AGAAGCTGTG | TTAGAACAGC | 4380 |
| ATGGGAGCCA | GCCTTCTAAC | AGCTACCCTT | CCATCATAAG | TGACTCTTCT | GCCCTTGAGG | 4440 |
| ACCTGCGAAA | TCCAGAACAA | AGCACATCAG | AAAAAGCAGT | ATTAACTTCA | CAGAAAAGTA | 4500 |
| GTGAATACCC | TATAAGCCAG | AATCCAGAAG | GCCTTTCTGC | TGACAAGTTT | GAGGTGTCTG | 4560 |
| CAGATAGTTC | TACCAGTAAA | AATAAAGAAC | CAGGAGTGGA | AAGGTCATCC | CCTTCTAAAT | 4620 |
| GCCCATCATT | AGATGATAGG | TGGTACATGC | ACAGTTGCTC | TGGGAGTCTT | CAGAATAGAA | 4680 |
| ACTACCCATC | TCAAGAGGAG | CTCATTAAGG | TTGTTGATGT | GGAGGAGCAA | CAGCTGGAAG | 4740 |
| AGTCTGGGCC | ACACGATTTG | ACGGAAACAT | CTTACTTGCC | AAGGCAAGAT | CTAGAGGGAA | 4800 |
| CCCCTTACCT | GGAATCTGGA | ATCAGCCTCT | TCTCTGATGA | CCCTGAATCT | GATCCTTCTG | 4860 |
| AAGACAGAGC | CCCAGAGTCA | GCTCGTGTTG | GCAACATACC | ATCTTCAACC | TCTGCATTGA | 4920 |
| AAGTTCCCCA | ATTGAAAGTT | GCAGAATCTG | CCCAGAGTCC | AGCTGCTGCT | CATACTACTG | 4980 |
| ATACTGCTGG | GTATAATGCA | ATGGAAGAAA | GTGTGAGCAG | GGAGAAGCCA | GAATTGACAG | 5040 |

```
CTTCAACAGA  AAGGGTCAAC  AAAAGAATGT  CCATGGTGGT  GTCTGGCCTG  ACCCCAGAAG    5100

AATTTATGCT  CGTGTACAAG  TTTGCCAGAA  AACACCACAT  CACTTTAACT  AATCTAATTA    5160

CTGAAGAGAC  TACTCATGTT  GTTATGAAAA  CAGATGCTGA  GTTTGTGTGT  GAACGGACAC    5220

TGAAATATTT  TCTAGGAATT  GCGGGAGGAA  AATGGGTAGT  TAGCTATTTC  TGGGTGACCC    5280

AGTCTATTAA  AGAAAGAAAA  ATGCTGAATG  AGCATGATTT  TGAAGTCAGA  GGAGATGTGG    5340

TCAATGGAAG  AAACCACCAA  GGTCCAAAGC  GAGCAAGAGA  ATCCCAGGAC  AGAAAGATCT    5400

TCAGGGGCT   AGAAATCTGT  TGCTATGGGC  CCTTCACCAA  CATGCCCACA  GATCAACTGG    5460

AATGGATGGT  ACAGCTGTGT  GGTGCTTCTG  TGGTGAAGGA  GCTTTCATCA  TTCACCCTTG    5520

GCACAGGTGT  CCACCCAATT  GTGGTTGTGC  AGCCAGATGC  CTGGACAGAG  GACAATGGCT    5580

TCCATGCAAT  TGGGCAGATG  TGTGAGGCAC  CTGTGGTGAC  CCGAGAGTGG  GTGTTGGACA    5640

GTGTAGCACT  CTACCAGTGC  CAGGAGCTGG  ACACCTAACC  TGATACCCCA  GATCCCCCAC    5700

AGCCACTACT  GA                                                            5712
```

( 2 ) INFORMATION FOR SEQ ID NO:13:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Met Asp Leu Ser Ala Leu Arg Val Glu Glu Val Gln Asn Val Ile Asn
1               5                   10                  15
Ala Met Gln Lys Ile Leu Glu Cys Pro Ile
            20                  25
```

( 2 ) INFORMATION FOR SEQ ID NO:14:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Met Asp Leu Ser Ala Leu Arg Val Glu Glu Val Gln Asn Val Ile Asn
1               5                   10                  15
Ala Met Gln Lys Ile Leu Glu Cys Pro Ile Cys Leu Glu Leu Ile Lys
            20                  25                  30
Glu Pro Val Ser Thr Val
            35
```

( 2 ) INFORMATION FOR SEQ ID NO:15:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met Asp Leu Ser Ala Leu Arg Val Glu Glu Val Gln Asn Val Ile Asn
1               5                   10                  15
```

```
Ala  Met  Gln  Lys  Ile  Leu  Glu  Cys  Pro  Ile  Cys  Leu  Glu  Leu  Ile  Lys
          20                       25                      30

Glu  Pro  Val  Ser  Thr  Lys  Cys  Asp  His  Ile  Phe  Cys  Lys  Phe  Cys  Met
               35                      40                      45

Leu  Lys  Leu  Leu  Asn  Gln  Lys  Lys  Gly  Pro  Ser  Gln  Cys  Pro  Leu
     50                       55                      60
```

( 2 ) INFORMATION FOR SEQ ID NO:16:

( i ) SEQUENCE CHARACTERISTICS:
       ( A ) LENGTH: 1863 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:16:

```
Met  Asp  Leu  Ser  Ala  Leu  Arg  Val  Glu  Glu  Val  Gln  Asn  Val  Ile  Asn
1              5                       10                      15

Ala  Met  Gln  Lys  Ile  Leu  Glu  Cys  Pro  Ile  Cys  Leu  Glu  Leu  Ile  Lys
          20                       25                      30

Glu  Pro  Val  Ser  Thr  Lys  Cys  Asp  His  Ile  Phe  Cys  Lys  Phe  Cys  Met
               35                      40                      45

Leu  Lys  Leu  Leu  Asn  Gln  Lys  Lys  Gly  Pro  Ser  Gln  Gly  Pro  Leu  Cys
     50                       55                      60

Lys  Asn  Asp  Ile  Thr  Lys  Arg  Ser  Leu  Gln  Glu  Ser  Thr  Arg  Phe  Ser
65                       70                      75                           80

Gln  Leu  Val  Glu  Glu  Leu  Leu  Lys  Ile  Ile  Cys  Ala  Phe  Gln  Leu  Asp
                    85                      90                      95

Thr  Gly  Leu  Glu  Tyr  Ala  Asn  Ser  Tyr  Asn  Phe  Ala  Lys  Lys  Glu  Asn
               100                     105                     110

Asn  Ser  Pro  Glu  His  Leu  Lys  Asp  Glu  Val  Ser  Ile  Ile  Gln  Ser  Met
               115                     120                     125

Gly  Tyr  Arg  Asn  Arg  Ala  Lys  Arg  Leu  Leu  Gln  Ser  Glu  Pro  Glu  Asn
          130                     135                     140

Pro  Ser  Leu  Gln  Glu  Thr  Ser  Leu  Ser  Val  Gln  Leu  Ser  Asn  Leu  Gly
145                     150                     155                          160

Thr  Val  Arg  Thr  Leu  Arg  Thr  Lys  Gln  Arg  Ile  Gln  Pro  Gln  Lys  Thr
               165                     170                     175

Ser  Val  Tyr  Ile  Glu  Leu  Gly  Ser  Asp  Ser  Ser  Glu  Asp  Thr  Val  Asn
               180                     185                     190

Lys  Ala  Thr  Tyr  Cys  Ser  Val  Gly  Asp  Gln  Glu  Leu  Leu  Gln  Ile  Thr
          195                     200                     205

Pro  Gln  Gly  Thr  Arg  Asp  Glu  Ile  Ser  Leu  Asp  Ser  Ala  Lys  Lys  Ala
     210                     215                     220

Ala  Cys  Glu  Phe  Ser  Glu  Thr  Asp  Val  Thr  Asn  Thr  Glu  His  His  Gln
225                     230                     235                          240

Pro  Ser  Asn  Asn  Asp  Leu  Asn  Thr  Thr  Glu  Lys  Arg  Ala  Ala  Glu  Arg
                    245                     250                     255

His  Pro  Glu  Lys  Tyr  Gln  Gly  Ser  Ser  Val  Ser  Asn  Leu  His  Val  Glu
               260                     265                     270

Pro  Cys  Gly  Thr  Asn  Thr  His  Ala  Ser  Ser  Leu  Gln  His  Glu  Asn  Ser
          275                     280                     285

Ser  Leu  Leu  Leu  Thr  Lys  Asp  Arg  Met  Asn  Val  Glu  Lys  Ala  Glu  Phe
     290                     295                     300
```

| Cys | Asn | Lys | Ser | Lys | Gln | Pro | Gly | Leu | Ala | Arg | Ser | Gln | His | Asn | Arg |
|-----|-----|-----|-----|-----|-----|-----|-----|-----|-----|-----|-----|-----|-----|-----|-----|
| 305 |     |     |     | 310 |     |     |     | 315 |     |     |     |     |     |     | 320 |
| Trp | Ala | Gly | Ser | Lys | Glu | Thr | Cys | Asn | Asp | Arg | Arg | Thr | Pro | Ser | Thr |
|     |     |     |     | 325 |     |     |     |     | 330 |     |     |     |     | 335 |     |
| Glu | Lys | Lys | Val | Asp | Leu | Asn | Ala | Asp | Pro | Leu | Cys | Glu | Arg | Lys | Glu |
|     |     |     | 340 |     |     |     |     | 345 |     |     |     |     | 350 |     |     |
| Trp | Asn | Lys | Gln | Lys | Leu | Pro | Cys | Ser | Glu | Asn | Pro | Arg | Asp | Thr | Glu |
|     |     |     | 355 |     |     |     |     | 360 |     |     |     |     | 365 |     |     |
| Asp | Val | Pro | Trp | Ile | Thr | Leu | Asn | Ser | Ser | Ile | Gln | Lys | Val | Asn | Glu |
|     |     | 370 |     |     |     |     | 375 |     |     |     |     | 380 |     |     |     |
| Trp | Phe | Ser | Arg | Ser | Asp | Glu | Leu | Leu | Gly | Ser | Asp | Asp | Ser | His | Asp |
| 385 |     |     |     |     | 390 |     |     |     |     | 395 |     |     |     |     | 400 |
| Gly | Glu | Ser | Glu | Ser | Asn | Ala | Lys | Val | Ala | Asp | Val | Leu | Asp | Val | Leu |
|     |     |     |     | 405 |     |     |     |     | 410 |     |     |     |     | 415 |     |
| Asn | Glu | Val | Asp | Glu | Tyr | Ser | Gly | Ser | Ser | Glu | Lys | Ile | Asp | Leu | Leu |
|     |     |     | 420 |     |     |     |     | 425 |     |     |     |     | 430 |     |     |
| Ala | Ser | Asp | Pro | His | Glu | Ala | Leu | Ile | Cys | Lys | Ser | Glu | Arg | Val | His |
|     |     |     | 435 |     |     |     |     | 440 |     |     |     |     | 445 |     |     |
| Ser | Lys | Ser | Val | Glu | Ser | Asn | Ile | Glu | Asp | Lys | Ile | Phe | Gly | Lys | Thr |
|     | 450 |     |     |     |     | 455 |     |     |     |     | 460 |     |     |     |     |
| Tyr | Arg | Lys | Lys | Ala | Ser | Leu | Pro | Asn | Leu | Ser | His | Val | Thr | Glu | Asn |
| 465 |     |     |     |     | 470 |     |     |     |     | 475 |     |     |     |     | 480 |
| Leu | Ile | Ile | Gly | Ala | Phe | Val | Thr | Glu | Pro | Gln | Ile | Ile | Gln | Glu | Arg |
|     |     |     |     | 485 |     |     |     |     | 490 |     |     |     |     | 495 |     |
| Pro | Leu | Thr | Asn | Lys | Leu | Lys | Arg | Lys | Arg | Arg | Pro | Thr | Ser | Gly | Leu |
|     |     |     | 500 |     |     |     |     | 505 |     |     |     |     | 510 |     |     |
| His | Pro | Glu | Asp | Phe | Ile | Lys | Lys | Ala | Asp | Leu | Ala | Val | Gln | Lys | Thr |
|     |     |     | 515 |     |     |     | 520 |     |     |     |     | 525 |     |     |     |
| Pro | Glu | Met | Ile | Asn | Gln | Gly | Thr | Asn | Gln | Thr | Glu | Gln | Asn | Gly | Gln |
|     | 530 |     |     |     |     | 535 |     |     |     |     | 540 |     |     |     |     |
| Val | Met | Asn | Ile | Thr | Asn | Ser | Gly | His | Glu | Asn | Lys | Thr | Lys | Gly | Asp |
| 545 |     |     |     |     | 550 |     |     |     |     | 555 |     |     |     |     | 560 |
| Ser | Ile | Gln | Asn | Glu | Lys | Asn | Pro | Asn | Pro | Ile | Glu | Ser | Leu | Glu | Lys |
|     |     |     |     |     | 565 |     |     |     | 570 |     |     |     |     | 575 |     |
| Glu | Ser | Ala | Phe | Lys | Thr | Lys | Ala | Glu | Pro | Ile | Ser | Ser | Ser | Ile | Ser |
|     |     |     | 580 |     |     |     |     | 585 |     |     |     |     | 590 |     |     |
| Asn | Met | Glu | Leu | Glu | Leu | Asn | Ile | His | Asn | Ser | Lys | Ala | Pro | Lys | Lys |
|     |     |     |     | 595 |     |     |     |     | 600 |     |     |     |     | 605 |     |
| Asn | Arg | Leu | Arg | Arg | Lys | Ser | Ser | Thr | Arg | His | Ile | His | Ala | Leu | Glu |
|     |     | 610 |     |     |     |     | 615 |     |     |     |     | 620 |     |     |     |
| Leu | Val | Val | Ser | Arg | Asn | Leu | Ser | Pro | Pro | Asn | Cys | Thr | Glu | Leu | Gln |
| 625 |     |     |     |     | 630 |     |     |     |     | 635 |     |     |     |     | 640 |
| Ile | Asp | Ser | Cys | Ser | Ser | Ser | Glu | Glu | Ile | Lys | Lys | Lys | Lys | Tyr | Asn |
|     |     |     |     | 645 |     |     |     |     | 650 |     |     |     |     | 655 |     |
| Gln | Met | Pro | Val | Arg | His | Ser | Arg | Asn | Leu | Gln | Leu | Met | Glu | Gly | Lys |
|     |     |     | 660 |     |     |     |     | 665 |     |     |     |     | 670 |     |     |
| Glu | Pro | Ala | Thr | Gly | Ala | Lys | Lys | Ser | Asn | Lys | Pro | Asn | Glu | Gln | Thr |
|     |     |     | 675 |     |     |     |     | 680 |     |     |     |     | 685 |     |     |
| Ser | Lys | Arg | His | Asp | Ser | Asp | Thr | Phe | Pro | Glu | Leu | Lys | Leu | Thr | Asn |
|     |     |     | 690 |     |     |     |     | 695 |     |     |     |     | 700 |     |     |
| Ala | Pro | Gly | Ser | Phe | Thr | Lys | Cys | Ser | Asn | Thr | Ser | Glu | Leu | Lys | Glu |
| 705 |     |     |     |     | 710 |     |     |     |     | 715 |     |     |     |     | 720 |
| Phe | Val | Asn | Pro | Ser | Leu | Pro | Arg | Glu | Glu | Lys | Glu | Glu | Lys | Leu | Glu |
|     |     |     |     | 725 |     |     |     |     | 730 |     |     |     |     | 735 |     |

```
Thr Val Lys Val Ser Asn Asn Ala Glu Asp Pro Lys Asp Leu Met Leu
        740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
        1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
            1045                1050                1055

Ser Ile Asn Glu Ile Gly Ser Ser Asp Glu Asn Ile Gln Ala Glu Leu
        1060                1065                1070

Gly Arg Asn Arg Gly Pro Lys Leu Asn Ala Met Leu Arg Leu Gly Val
        1075                1080                1085

Leu Gln Pro Glu Val Tyr Lys Gln Ser Leu Pro Gly Ser Asn Cys Lys
        1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
            1125                1130                1135

Met Gly Ser Ser His Ala Ser Gln Val Cys Ser Glu Thr Pro Asp Asp
            1140                1145                1150

Leu Leu Asp Asp Gly Glu Ile Lys Glu Asp Thr Ser Phe Ala Glu Asn
```

-continued

```
                    1155                    1160                    1165
Asp Ile Lys Glu Ser Ser Ala Val Phe Ser Lys Ser Val Gln Lys Gly
        1170                    1175                    1180
Glu Leu Ser Arg Ser Pro Ser Pro Phe Thr His Thr His Leu Ala Gln
1185                    1190                    1195                    1200
Gly Tyr Arg Arg Gly Ala Lys Lys Leu Glu Ser Ser Glu Glu Asn Leu
                    1205                    1210                    1215
Ser Ser Glu Asp Glu Glu Leu Pro Cys Phe Gln His Leu Leu Phe Gly
                    1220                    1225                    1230
Lys Val Asn Asn Ile Pro Ser Gln Ser Thr Arg His Ser Thr Val Ala
                    1235                    1240                    1245
Thr Glu Cys Leu Ser Lys Asn Thr Glu Glu Asn Leu Leu Ser Leu Lys
        1250                    1255                    1260
Asn Ser Leu Asn Asp Cys Ser Asn Gln Val Ile Leu Ala Lys Ala Ser
1265                    1270                    1275                    1280
Gln Glu His His Leu Ser Glu Glu Thr Lys Cys Ser Ala Ser Leu Phe
                    1285                    1290                    1295
Ser Ser Gln Cys Ser Glu Leu Glu Asp Leu Thr Ala Asn Thr Asn Thr
                    1300                    1305                    1310
Gln Asp Pro Phe Leu Ile Gly Ser Ser Lys Gln Met Arg His Gln Ser
                    1315                    1320                    1325
Glu Ser Gln Gly Val Gly Leu Ser Asp Lys Glu Leu Val Ser Asp Asp
        1330                    1335                    1340
Glu Glu Arg Gly Thr Gly Leu Glu Glu Asn Asn Gln Glu Glu Gln Ser
1345                    1350                    1355                    1360
Met Asp Ser Asn Leu Gly Glu Ala Ala Ser Gly Cys Glu Ser Glu Thr
                    1365                    1370                    1375
Ser Val Ser Glu Asp Cys Ser Gly Leu Ser Ser Gln Ser Asp Ile Leu
                    1380                    1385                    1390
Thr Thr Gln Gln Arg Asp Thr Met Gln His Asn Leu Ile Lys Leu Gln
                    1395                    1400                    1405
Gln Glu Met Ala Glu Leu Glu Ala Val Leu Glu Gln His Gly Ser Gln
        1410                    1415                    1420
Pro Ser Asn Ser Tyr Pro Ser Ile Ile Ser Asp Ser Ser Ala Leu Glu
1425                    1430                    1435                    1440
Asp Leu Arg Asn Pro Glu Gln Ser Thr Ser Glu Lys Ala Val Leu Thr
                    1445                    1450                    1455
Ser Gln Lys Ser Ser Glu Tyr Pro Ile Ser Gln Asn Pro Glu Gly Leu
                    1460                    1465                    1470
Ser Ala Asp Lys Phe Glu Val Ser Ala Asp Ser Ser Thr Ser Lys Asn
        1475                    1480                    1485
Lys Glu Pro Gly Val Glu Arg Ser Ser Pro Ser Lys Cys Pro Ser Leu
        1490                    1495                    1500
Asp Asp Arg Trp Tyr Met His Ser Cys Ser Gly Ser Leu Gln Asn Arg
1505                    1510                    1515                    1520
Asn Tyr Pro Ser Gln Glu Glu Leu Ile Lys Val Val Asp Val Glu Glu
                    1525                    1530                    1535
Gln Gln Leu Glu Glu Ser Gly Pro His Asp Leu Thr Glu Thr Ser Tyr
                    1540                    1545                    1550
Leu Pro Arg Gln Asp Leu Glu Gly Thr Pro Tyr Leu Glu Ser Gly Ile
                    1555                    1560                    1565
Ser Leu Phe Ser Asp Asp Pro Glu Ser Asp Pro Ser Glu Asp Arg Ala
        1570                    1575                    1580
```

```
Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
            1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
            1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
        1795                1800                1805

Val Val Gln Pro Asp Ala Trp Thr Glu Asp Asn Gly Phe His Ala Ile
1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
            1845                1850                1855

Gln Ile Pro His Ser His Tyr
            1860

( 2 ) INFORMATION FOR SEQ ID NO:17:

( i ) SEQUENCE CHARACTERISTICS:
            ( A ) LENGTH: 80 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:17:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Ser Val Leu Lys Arg Leu Ile Ile Thr Cys
```

(2) INFORMATION FOR SEQ ID NO:18:

(i) SEQUENCE CHARACTERISTICS:
    (A) LENGTH: 312 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:18:

```
Met Asp Leu Ser Ala Leu Arg Val Glu Glu Val Gln Asn Val Ile Asn
  1               5                  10                  15
Ala Met Gln Lys Ile Leu Glu Cys Pro Ile Cys Leu Glu Leu Ile Lys
             20                  25                  30
Glu Pro Val Ser Thr Lys Cys Asp His Ile Phe Cys Lys Phe Cys Met
         35                  40                  45
Leu Lys Leu Leu Asn Gln Lys Lys Gly Pro Ser Gln Cys Pro Leu Cys
 50                  55                  60
Lys Asn Asp Ile Thr Lys Arg Ser Leu Gln Glu Ser Thr Arg Phe Ser
 65                  70                  75                  80
Gln Leu Val Glu Glu Leu Leu Lys Ile Ile Cys Ala Phe Gln Leu Asp
             85                  90                  95
Thr Gly Leu Glu Tyr Ala Asn Ser Tyr Asn Phe Ala Lys Lys Glu Asn
            100                 105                 110
Asn Ser Pro Glu His Leu Lys Asp Glu Val Ser Ile Ile Gln Ser Met
        115                 120                 125
Gly Tyr Arg Asn Arg Ala Lys Arg Leu Leu Gln Ser Glu Pro Glu Asn
130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
            165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
    290                 295                 300
Cys Asn Lys Ser Lys Arg Leu Ala
305                 310
```

(2) INFORMATION FOR SEQ ID NO:19:

(i) SEQUENCE CHARACTERISTICS:
    (A) LENGTH: 765 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

```
Met Asp Leu Ser Ala Leu Arg Val Glu Glu Val Gln Asn Val Ile Asn
 1               5                  10                  15
Ala Met Gln Lys Ile Leu Glu Cys Pro Ile Cys Leu Glu Leu Ile Lys
                20                  25                  30
Glu Pro Val Ser Thr Lys Cys Asp His Ile Phe Cys Lys Phe Cys Met
            35                  40                  45
Leu Lys Leu Leu Asn Gln Lys Lys Gly Pro Ser Gln Cys Pro Leu Cys
    50                  55                  60
Lys Asn Asp Ile Thr Lys Arg Ser Leu Gln Glu Ser Thr Arg Phe Ser
65                  70                  75                  80
Gln Leu Val Glu Glu Leu Leu Lys Ile Ile Cys Ala Phe Gln Leu Asp
                85                  90                  95
Thr Gly Leu Glu Tyr Ala Asn Ser Tyr Asn Phe Ala Lys Lys Glu Asn
            100                 105                 110
Asn Ser Pro Glu His Leu Lys Asp Glu Val Ser Ile Ile Gln Ser Met
        115                 120                 125
Gly Tyr Arg Asn Arg Ala Lys Arg Leu Leu Gln Ser Glu Pro Glu Asn
130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
    370                 375                 380
```

| | | | | | | | | | | | | | | |
|---|---|---|---|---|---|---|---|---|---|---|---|---|---|---|
| Trp 385 | Phe | Ser | Arg | Ser | Asp 390 | Glu | Leu | Leu | Gly | Ser 395 | Asp | Asp | Ser | His | Asp 400 |
| Gly | Glu | Ser | Glu | Ser 405 | Asn | Ala | Lys | Val | Ala 410 | Asp | Val | Leu | Asp | Val 415 | Leu |
| Asn | Glu | Val | Asp 420 | Glu | Tyr | Ser | Gly | Ser 425 | Ser | Glu | Lys | Ile | Asp 430 | Leu | Leu |
| Ala | Ser | Asp 435 | Pro | His | Glu | Ala | Leu 440 | Ile | Cys | Lys | Ser | Glu 445 | Arg | Val | His |
| Ser | Lys 450 | Ser | Val | Glu | Ser | Asn 455 | Ile | Glu | Asp | Lys | Ile 460 | Phe | Gly | Lys | Thr |
| Tyr 465 | Arg | Lys | Lys | Ala | Ser 470 | Leu | Pro | Asn | Leu | Ser 475 | His | Val | Thr | Glu | Asn 480 |
| Leu | Ile | Ile | Gly | Ala 485 | Phe | Val | Thr | Glu | Pro 490 | Gln | Ile | Ile | Gln | Glu 495 | Arg |
| Pro | Leu | Thr | Asn 500 | Lys | Leu | Lys | Arg | Lys 505 | Arg | Arg | Pro | Thr | Ser 510 | Gly | Leu |
| His | Pro | Glu 515 | Asp | Phe | Ile | Lys | Lys 520 | Ala | Asp | Leu | Ala | Val 525 | Gln | Lys | Thr |
| Pro | Glu 530 | Met | Ile | Asn | Gln | Gly 535 | Thr | Asn | Gln | Thr | Glu 540 | Gln | Asn | Gly | Gln |
| Val 545 | Met | Asn | Ile | Thr | Asn 550 | Ser | Gly | His | Glu | Asn 555 | Lys | Thr | Lys | Gly | Asp 560 |
| Ser | Ile | Gln | Asn | Glu 565 | Lys | Asn | Pro | Asn | Pro 570 | Ile | Glu | Ser | Leu | Glu 575 | Lys |
| Glu | Ser | Ala | Phe 580 | Lys | Thr | Lys | Ala | Glu 585 | Pro | Ile | Ser | Ser | Ser 590 | Ile | Ser |
| Asn | Met | Glu 595 | Leu | Glu | Leu | Asn | Ile 600 | His | Asn | Ser | Lys | Ala 605 | Pro | Lys | Lys |
| Asn | Arg 610 | Leu | Arg | Arg | Lys | Ser 615 | Ser | Thr | Arg | His | Ile 620 | His | Ala | Leu | Glu |
| Leu 625 | Val | Val | Ser | Arg | Asn 630 | Leu | Ser | Pro | Pro | Asn 635 | Cys | Thr | Glu | Leu | Gln 640 |
| Ile | Asp | Ser | Cys | Ser 645 | Ser | Ser | Glu | Glu | Ile 650 | Lys | Lys | Lys | Lys | Tyr 655 | Asn |
| Gln | Met | Pro | Val 660 | Arg | His | Ser | Arg | Asn 665 | Leu | Gln | Leu | Met | Glu 670 | Gly | Lys |
| Glu | Pro | Ala 675 | Thr | Gly | Ala | Lys | Lys 680 | Ser | Asn | Lys | Pro | Asn 685 | Glu | Gln | Thr |
| Ser | Lys 690 | Arg | His | Asp | Ser | Asp 695 | Thr | Phe | Pro | Glu | Leu 700 | Lys | Leu | Thr | Asn |
| Ala 705 | Pro | Gly | Ser | Phe | Thr 710 | Lys | Cys | Ser | Asn | Thr 715 | Ser | Glu | Leu | Lys | Glu 720 |
| Phe | Val | Asn | Pro | Ser 725 | Leu | Pro | Arg | Glu | Glu 730 | Lys | Glu | Glu | Lys | Leu 735 | Glu |
| Thr | Val | Lys | Val 740 | Ser | Asn | Asn | Ala | Glu 745 | Asp | Pro | Lys | Asp | Leu 750 | Met | Leu |
| Ser | Gly | Glu | Arg 755 | Val | Leu | Gln | Thr | Glu 760 | Arg | Ser | Val | Glu 765 | | | |

( 2 ) INFORMATION FOR SEQ ID NO:20:

( i ) SEQUENCE CHARACTERISTICS:
        ( A ) LENGTH: 900 amino acids
        ( B ) TYPE: amino acid
        ( C ) STRANDEDNESS: single
        ( D ) TOPOLOGY: linear (ii) MOLECULE TYPE: protein (xi) SEQUENCE DESCRIPTION: SEQ ID NO:20:

| Met<br>1 | Asp | Leu | Ser | Ala<br>5 | Leu | Arg | Val | Glu | Glu<br>10 | Val | Gln | Asn | Val | Ile<br>15 | Asn |
|---|---|---|---|---|---|---|---|---|---|---|---|---|---|---|---|
| Ala | Met | Gln | Lys<br>20 | Ile | Leu | Glu | Cys | Pro<br>25 | Ile | Cys | Leu | Glu | Leu<br>30 | Ile | Lys |
| Glu | Pro | Val<br>35 | Ser | Thr | Lys | Cys | Asp<br>40 | His | Ile | Phe | Cys | Lys<br>45 | Phe | Cys | Met |
| Leu | Lys<br>50 | Leu | Leu | Asn | Gln | Lys<br>55 | Lys | Gly | Pro | Ser | Gln<br>60 | Cys | Pro | Leu | Cys |
| Lys<br>65 | Asn | Asp | Ile | Thr | Lys<br>70 | Arg | Ser | Leu | Gln | Glu<br>75 | Ser | Thr | Arg | Phe | Ser<br>80 |
| Gln | Leu | Val | Glu | Glu<br>85 | Leu | Leu | Lys | Ile | Ile<br>90 | Cys | Ala | Phe | Gln | Leu<br>95 | Asp |
| Thr | Gly | Leu | Glu<br>100 | Tyr | Ala | Asn | Ser | Tyr<br>105 | Asn | Phe | Ala | Lys | Lys<br>110 | Glu | Asn |
| Asn | Ser | Pro<br>115 | Glu | His | Leu | Lys | Asp<br>120 | Glu | Val | Ser | Ile | Ile<br>125 | Gln | Ser | Met |
| Gly | Tyr<br>130 | Arg | Asn | Arg | Ala | Lys<br>135 | Arg | Leu | Leu | Gln | Ser<br>140 | Glu | Pro | Glu | Asn |
| Pro<br>145 | Ser | Leu | Gln | Glu | Thr<br>150 | Ser | Leu | Ser | Val | Gln<br>155 | Leu | Ser | Asn | Leu | Gly<br>160 |
| Thr | Val | Arg | Thr | Leu<br>165 | Arg | Thr | Lys | Gln | Arg<br>170 | Ile | Gln | Pro | Gln | Lys<br>175 | Thr |
| Ser | Val | Tyr | Ile<br>180 | Glu | Leu | Gly | Ser | Asp<br>185 | Ser | Ser | Glu | Asp | Thr<br>190 | Val | Asn |
| Lys | Ala | Thr<br>195 | Tyr | Cys | Ser | Val | Gly<br>200 | Asp | Gln | Glu | Leu | Leu<br>205 | Gln | Ile | Thr |
| Pro | Gln<br>210 | Gly | Thr | Arg | Asp | Glu<br>215 | Ile | Ser | Leu | Asp | Ser<br>220 | Ala | Lys | Lys | Ala |
| Ala<br>225 | Cys | Glu | Phe | Ser | Glu<br>230 | Thr | Asp | Val | Thr | Asn<br>235 | Thr | Glu | His | His | Gln<br>240 |
| Pro | Ser | Asn | Asn | Asp<br>245 | Leu | Asn | Thr | Thr | Glu<br>250 | Lys | Arg | Ala | Ala | Glu<br>255 | Arg |
| His | Pro | Glu | Lys<br>260 | Tyr | Gln | Gly | Ser | Ser<br>265 | Val | Ser | Asn | Leu | His<br>270 | Val | Glu |
| Pro | Cys | Gly<br>275 | Thr | Asn | Thr | His | Ala<br>280 | Ser | Ser | Leu | Gln | His<br>285 | Glu | Asn | Ser |
| Ser | Leu<br>290 | Leu | Leu | Thr | Lys | Asp<br>295 | Arg | Met | Asn | Val | Glu<br>300 | Lys | Ala | Glu | Phe |
| Cys<br>305 | Asn | Lys | Ser | Lys | Gln<br>310 | Pro | Gly | Leu | Ala | Arg<br>315 | Ser | Gln | His | Asn | Arg<br>320 |
| Trp | Ala | Gly | Ser | Lys<br>325 | Glu | Thr | Cys | Asn | Asp<br>330 | Arg | Arg | Thr | Pro | Ser<br>335 | Thr |
| Glu | Lys | Lys | Val<br>340 | Asp | Leu | Asn | Ala | Asp<br>345 | Pro | Leu | Cys | Glu | Arg<br>350 | Lys | Glu |
| Trp | Asn | Lys<br>355 | Gln | Lys | Leu | Pro | Cys<br>360 | Ser | Glu | Asn | Pro | Arg<br>365 | Asp | Thr | Glu |
| Asp | Val<br>370 | Pro | Trp | Ile | Thr | Leu<br>375 | Asn | Ser | Ser | Ile | Gln<br>380 | Lys | Val | Asn | Glu |
| Trp<br>385 | Phe | Ser | Arg | Ser | Asp<br>390 | Glu | Leu | Leu | Gly | Ser<br>395 | Asp | Asp | Ser | His | Asp<br>400 |

-continued

| | | | | | | | | | | | | | | |
|---|---|---|---|---|---|---|---|---|---|---|---|---|---|---|
| Gly | Glu | Ser | Glu | Ser | Asn | Ala | Lys | Val | Ala | Asp | Val | Leu | Asp | Val | Leu |
| | | | 405 | | | | 410 | | | | | 415 | | | |
| Asn | Glu | Val | Asp | Glu | Tyr | Ser | Gly | Ser | Ser | Glu | Lys | Ile | Asp | Leu | Leu |
| | | | 420 | | | | 425 | | | | | 430 | | | |
| Ala | Ser | Asp | Pro | His | Glu | Ala | Leu | Ile | Cys | Lys | Ser | Glu | Arg | Val | His |
| | | 435 | | | | 440 | | | | | 445 | | | | |
| Ser | Lys | Ser | Val | Glu | Ser | Asn | Ile | Glu | Asp | Lys | Ile | Phe | Gly | Lys | Thr |
| | 450 | | | | | 455 | | | | | 460 | | | | |
| Tyr | Arg | Lys | Lys | Ala | Ser | Leu | Pro | Asn | Leu | Ser | His | Val | Thr | Glu | Asn |
| 465 | | | | | 470 | | | | | 475 | | | | | 480 |
| Leu | Ile | Ile | Gly | Ala | Phe | Val | Thr | Glu | Pro | Gln | Ile | Ile | Gln | Glu | Arg |
| | | | 485 | | | | | 490 | | | | | 495 | | |
| Pro | Leu | Thr | Asn | Lys | Leu | Lys | Arg | Lys | Arg | Arg | Pro | Thr | Ser | Gly | Leu |
| | | | 500 | | | | | 505 | | | | | 510 | | |
| His | Pro | Glu | Asp | Phe | Ile | Lys | Lys | Ala | Asp | Leu | Ala | Val | Gln | Lys | Thr |
| | | 515 | | | | | 520 | | | | | 525 | | | |
| Pro | Glu | Met | Ile | Asn | Gln | Gly | Thr | Asn | Gln | Thr | Glu | Gln | Asn | Gly | Gln |
| | 530 | | | | | 535 | | | | | 540 | | | | |
| Val | Met | Asn | Ile | Thr | Asn | Ser | Gly | His | Glu | Asn | Lys | Thr | Lys | Gly | Asp |
| 545 | | | | | 550 | | | | | 555 | | | | | 560 |
| Ser | Ile | Gln | Asn | Glu | Lys | Asn | Pro | Asn | Pro | Ile | Glu | Ser | Leu | Glu | Lys |
| | | | | 565 | | | | | 570 | | | | | 575 | |
| Glu | Ser | Ala | Phe | Lys | Thr | Lys | Ala | Glu | Pro | Ile | Ser | Ser | Ser | Ile | Ser |
| | | | 580 | | | | | 585 | | | | | 590 | | |
| Asn | Met | Glu | Leu | Glu | Leu | Asn | Ile | His | Asn | Ser | Lys | Ala | Pro | Lys | Lys |
| | | 595 | | | | | 600 | | | | | 605 | | | |
| Asn | Arg | Leu | Arg | Arg | Lys | Ser | Ser | Thr | Arg | His | Ile | His | Ala | Leu | Glu |
| | 610 | | | | | 615 | | | | | 620 | | | | |
| Leu | Val | Val | Ser | Arg | Asn | Leu | Ser | Pro | Pro | Asn | Cys | Thr | Glu | Leu | Gln |
| 625 | | | | | 630 | | | | | 635 | | | | | 640 |
| Ile | Asp | Ser | Cys | Ser | Ser | Ser | Glu | Glu | Ile | Lys | Lys | Lys | Lys | Tyr | Asn |
| | | | | 645 | | | | | 650 | | | | | 655 | |
| Gln | Met | Pro | Val | Arg | His | Ser | Arg | Asn | Leu | Gln | Leu | Met | Glu | Gly | Lys |
| | | | 660 | | | | | 665 | | | | | 670 | | |
| Glu | Pro | Ala | Thr | Gly | Ala | Lys | Lys | Ser | Asn | Lys | Pro | Asn | Glu | Gln | Thr |
| | | 675 | | | | | 680 | | | | | 685 | | | |
| Ser | Lys | Arg | His | Asp | Ser | Asp | Thr | Phe | Pro | Glu | Leu | Lys | Leu | Thr | Asn |
| | 690 | | | | | 695 | | | | | 700 | | | | |
| Ala | Pro | Gly | Ser | Phe | Thr | Lys | Cys | Ser | Asn | Thr | Ser | Glu | Leu | Lys | Glu |
| 705 | | | | | 710 | | | | | 715 | | | | | 720 |
| Phe | Val | Asn | Pro | Ser | Leu | Pro | Arg | Glu | Glu | Lys | Glu | Glu | Lys | Leu | Glu |
| | | | | 725 | | | | | 730 | | | | | 735 | |
| Thr | Val | Lys | Val | Ser | Asn | Asn | Ala | Glu | Asp | Pro | Lys | Asp | Leu | Met | Leu |
| | | | 740 | | | | | 745 | | | | | 750 | | |
| Ser | Gly | Glu | Arg | Val | Leu | Gln | Thr | Glu | Arg | Ser | Val | Glu | Ser | Ser | Ser |
| | | 755 | | | | | 760 | | | | | 765 | | | |
| Ile | Ser | Leu | Val | Pro | Gly | Thr | Asp | Tyr | Gly | Thr | Gln | Glu | Ser | Ile | Ser |
| | 770 | | | | | 775 | | | | | 780 | | | | |
| Leu | Leu | Glu | Val | Ser | Thr | Leu | Gly | Lys | Ala | Lys | Thr | Glu | Pro | Asn | Lys |
| 785 | | | | | 790 | | | | | 795 | | | | | 800 |
| Cys | Val | Ser | Gln | Cys | Ala | Ala | Phe | Glu | Asn | Pro | Lys | Gly | Leu | Ile | His |
| | | | | 805 | | | | | 810 | | | | | 815 | |
| Gly | Cys | Ser | Lys | Asp | Asn | Arg | Asn | Asp | Thr | Glu | Gly | Phe | Lys | Tyr | Pro |
| | | | 820 | | | | | 825 | | | | | 830 | | |

| | | | | | | | | | | | | | | |
|---|---|---|---|---|---|---|---|---|---|---|---|---|---|---|
| Leu | Gly | His | Glu | Val | Asn | His | Ser | Arg | Glu | Thr | Ser | Ile | Glu | Met | Glu |
| | | 835 | | | | 840 | | | | | | 845 | | | |
| Glu | Ser | Glu | Leu | Asp | Ala | Gln | Tyr | Leu | Gln | Asn | Thr | Phe | Lys | Val | Ser |
| | 850 | | | | | 855 | | | | | 860 | | | | |
| Lys | Arg | Gln | Ser | Phe | Ala | Pro | Phe | Ser | Asn | Pro | Gly | Asn | Ala | Glu | Glu |
| 865 | | | | | 870 | | | | | 875 | | | | | 880 |
| Glu | Cys | Ala | Thr | Phe | Ser | Ala | His | Ser | Gly | Ser | Leu | Lys | Thr | Lys | Ser |
| | | | | 885 | | | | | 890 | | | | | 895 | |
| Lys | Ser | His | Phe | | | | | | | | | | | | |
| | | | 900 | | | | | | | | | | | | |

( 2 ) INFORMATION FOR SEQ ID NO:21:

( i ) SEQUENCE CHARACTERISTICS:
        ( A ) LENGTH: 914 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

| | | | | | | | | | | | | | | | |
|---|---|---|---|---|---|---|---|---|---|---|---|---|---|---|---|
| Met | Asp | Leu | Ser | Ala | Leu | Arg | Val | Glu | Glu | Val | Gln | Asn | Val | Ile | Asn |
| 1 | | | | 5 | | | | | 10 | | | | | 15 | |
| Ala | Met | Gln | Lys | Ile | Leu | Glu | Cys | Pro | Ile | Cys | Leu | Glu | Leu | Ile | Lys |
| | | | 20 | | | | | 25 | | | | | 30 | | |
| Glu | Pro | Val | Ser | Thr | Lys | Cys | Asp | His | Ile | Phe | Cys | Lys | Phe | Cys | Met |
| | | | 35 | | | | | 40 | | | | | 45 | | |
| Leu | Lys | Leu | Leu | Asn | Gln | Lys | Lys | Gly | Pro | Ser | Gln | Cys | Pro | Leu | Cys |
| | 50 | | | | | 55 | | | | | 60 | | | | |
| Lys | Asn | Asp | Ile | Thr | Lys | Arg | Ser | Leu | Gln | Ser | Thr | Arg | Phe | Ser | |
| 65 | | | | | 70 | | | | | 75 | | | | | 80 |
| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |
| Thr | Gly | Leu | Glu | Tyr | Ala | Asn | Ser | Tyr | Asn | Phe | Ala | Lys | Lys | Glu | Asn |
| | | | 100 | | | | | 105 | | | | | 110 | | |
| Asn | Ser | Pro | Glu | His | Leu | Lys | Asp | Glu | Val | Ser | Ile | Ile | Gln | Ser | Met |
| | | 115 | | | | | 120 | | | | | 125 | | | |
| Gly | Tyr | Arg | Asn | Arg | Ala | Lys | Arg | Leu | Leu | Gln | Ser | Glu | Pro | Glu | Asn |
| | 130 | | | | | 135 | | | | | 140 | | | | |
| Pro | Ser | Leu | Gln | Glu | Thr | Ser | Leu | Ser | Val | Gln | Leu | Ser | Asn | Leu | Gly |
| 145 | | | | | 150 | | | | | 155 | | | | | 160 |
| Thr | Val | Arg | Thr | Leu | Arg | Thr | Lys | Gln | Arg | Ile | Gln | Pro | Gln | Lys | Thr |
| | | | | 165 | | | | | 170 | | | | | 175 | |
| Ser | Val | Tyr | Ile | Glu | Leu | Gly | Ser | Asp | Ser | Ser | Glu | Asp | Thr | Val | Asn |
| | | | 180 | | | | | 185 | | | | | 190 | | |
| Lys | Ala | Thr | Tyr | Cys | Ser | Val | Gly | Asp | Gln | Glu | Leu | Leu | Gln | Ile | Thr |
| | | 195 | | | | | 200 | | | | | 205 | | | |
| Pro | Gln | Gly | Thr | Arg | Asp | Glu | Ile | Ser | Leu | Asp | Ser | Ala | Lys | Lys | Ala |
| | 210 | | | | | 215 | | | | | 220 | | | | |
| Ala | Cys | Glu | Phe | Ser | Glu | Thr | Asp | Val | Thr | Asn | Thr | Glu | His | His | Gln |
| 225 | | | | | 230 | | | | | 235 | | | | | 240 |
| Pro | Ser | Asn | Asn | Asp | Leu | Asn | Thr | Thr | Glu | Lys | Arg | Ala | Ala | Glu | Arg |
| | | | | 245 | | | | | 250 | | | | | 255 | |
| His | Pro | Glu | Lys | Tyr | Gln | Gly | Ser | Ser | Val | Ser | Asn | Leu | His | Val | Glu |
| | | | 260 | | | | | 265 | | | | | 270 | | |

-continued

| | | | | | | | | | | | | | |
|---|---|---|---|---|---|---|---|---|---|---|---|---|---|
|Pro|Cys|Gly|Thr|Asn|Thr|His|Ala|Ser|Ser|Leu|Gln|His|Glu|Asn|Ser|
| |275| | | |280| | | | |285| | | | |
|Ser|Leu|Leu|Leu|Thr|Lys|Asp|Arg|Met|Asn|Val|Glu|Lys|Ala|Glu|Phe|
|290| | | | |295| | | | |300| | | | |
|Cys|Asn|Lys|Ser|Lys|Gln|Pro|Gly|Leu|Ala|Arg|Ser|Gln|His|Asn|Arg|
|305| | | | |310| | | | |315| | | | |320|
|Trp|Ala|Gly|Ser|Lys|Glu|Thr|Cys|Asn|Asp|Arg|Arg|Thr|Pro|Ser|Thr|
| | | | |325| | | | |330| | | | |335| |
|Glu|Lys|Lys|Val|Asp|Leu|Asn|Ala|Asp|Pro|Leu|Cys|Glu|Arg|Lys|Glu|
| | | |340| | | | |345| | | | |350| | |
|Trp|Asn|Lys|Gln|Lys|Leu|Pro|Cys|Ser|Glu|Asn|Pro|Arg|Asp|Thr|Glu|
| | |355| | | | |360| | | | |365| | | |
|Asp|Val|Pro|Trp|Ile|Thr|Leu|Asn|Ser|Ser|Ile|Gln|Lys|Val|Asn|Glu|
| |370| | | | |375| | | | |380| | | | |
|Trp|Phe|Ser|Arg|Ser|Asp|Glu|Leu|Leu|Gly|Ser|Asp|Ser|His|Asp|
|385| | | | |390| | | | |395| | | | |400|
|Gly|Glu|Ser|Glu|Ser|Asn|Ala|Lys|Val|Ala|Asp|Val|Leu|Asp|Val|Leu|
| | | | |405| | | | |410| | | | |415| |
|Asn|Glu|Val|Asp|Glu|Tyr|Ser|Gly|Ser|Ser|Glu|Lys|Ile|Asp|Leu|Leu|
| | | |420| | | | |425| | | | |430| | |
|Ala|Ser|Asp|Pro|His|Glu|Ala|Leu|Ile|Cys|Lys|Ser|Glu|Arg|Val|His|
| | |435| | | | |440| | | | |445| | | |
|Ser|Lys|Ser|Val|Glu|Ser|Asn|Ile|Glu|Asp|Lys|Ile|Phe|Gly|Lys|Thr|
| |450| | | | |455| | | | |460| | | | |
|Tyr|Arg|Lys|Lys|Ala|Ser|Leu|Pro|Asn|Leu|Ser|His|Val|Thr|Glu|Asn|
|465| | | | |470| | | | |475| | | | |480|
|Leu|Ile|Ile|Gly|Ala|Phe|Val|Thr|Glu|Pro|Gln|Ile|Ile|Gln|Glu|Arg|
| | | | |485| | | | |490| | | | |495| |
|Pro|Leu|Thr|Asn|Lys|Leu|Lys|Arg|Lys|Arg|Arg|Pro|Thr|Ser|Gly|Leu|
| | | |500| | | | |505| | | | |510| | |
|His|Pro|Glu|Asp|Phe|Ile|Lys|Lys|Ala|Asp|Leu|Ala|Val|Gln|Lys|Thr|
| | |515| | | | |520| | | | |525| | | |
|Pro|Glu|Met|Ile|Asn|Gln|Gly|Thr|Asn|Gln|Thr|Glu|Gln|Asn|Gly|Gln|
| |530| | | | |535| | | | |540| | | | |
|Val|Met|Asn|Ile|Thr|Asn|Ser|Gly|His|Glu|Asn|Lys|Thr|Lys|Gly|Asp|
|545| | | | |550| | | | |555| | | | |560|
|Ser|Ile|Gln|Asn|Glu|Lys|Asn|Pro|Asn|Pro|Ile|Glu|Ser|Leu|Glu|Lys|
| | | | |565| | | | |570| | | | |575| |
|Glu|Ser|Ala|Phe|Lys|Thr|Lys|Ala|Glu|Pro|Ile|Ser|Ser|Ser|Ile|Ser|
| | | |580| | | | |585| | | | |590| | |
|Asn|Met|Glu|Leu|Glu|Leu|Asn|Ile|His|Asn|Ser|Lys|Ala|Pro|Lys|Lys|
| | |595| | | | |600| | | | |605| | | |
|Asn|Arg|Leu|Arg|Arg|Lys|Ser|Ser|Thr|Arg|His|Ile|His|Ala|Leu|Glu|
| |610| | | | |615| | | | |620| | | | |
|Leu|Val|Val|Ser|Arg|Asn|Leu|Ser|Pro|Pro|Asn|Cys|Thr|Glu|Leu|Gln|
|625| | | | |630| | | | |635| | | | |640|
|Ile|Asp|Ser|Cys|Ser|Ser|Ser|Glu|Glu|Ile|Lys|Lys|Lys|Lys|Tyr|Asn|
| | | |645| | | | |650| | | | |655| | |
|Gln|Met|Pro|Val|Arg|His|Ser|Arg|Asn|Leu|Gln|Leu|Met|Glu|Gly|Lys|
| | |660| | | | |665| | | | |670| | | |
|Glu|Pro|Ala|Thr|Gly|Ala|Lys|Lys|Ser|Asn|Lys|Pro|Asn|Glu|Gln|Thr|
| |675| | | | |680| | | | |685| | | | |
|Ser|Lys|Arg|His|Asp|Ser|Asp|Thr|Phe|Pro|Glu|Leu|Lys|Leu|Thr|Asn|
| |690| | | | |695| | | | |700| | | | |

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu ( 2 ) INFORMATION FOR SEQ ID NO:22:

( i ) SEQUENCE CHARACTERISTICS:
        ( A ) LENGTH: 1202 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn

|     | 130 |     |     |     | 135 |     |     |     | 140 |     |     |     |
|-----|-----|-----|-----|-----|-----|-----|-----|-----|-----|-----|-----|-----|

Pro Ser Leu Gln Glu Thr Ser Leu Ser Val Gln Leu Ser Asn Leu Gly
145                     150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
    275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

| | | | | | | | | | | | | | | |
|---|---|---|---|---|---|---|---|---|---|---|---|---|---|---|
| Ser | Ile | Gln | Asn | Glu | Lys | Asn | Pro | Asn | Pro | Ile | Glu | Ser | Leu | Glu | Lys |
| | | | | 565 | | | | 570 | | | | | | 575 | |
| Glu | Ser | Ala | Phe | Lys | Thr | Lys | Ala | Glu | Pro | Ile | Ser | Ser | Ser | Ile | Ser |
| | | | 580 | | | | | 585 | | | | | 590 | | |
| Asn | Met | Glu | Leu | Glu | Leu | Asn | Ile | His | Asn | Ser | Lys | Ala | Pro | Lys | Lys |
| | | 595 | | | | | | 600 | | | | 605 | | | |
| Asn | Arg | Leu | Arg | Arg | Lys | Ser | Ser | Thr | Arg | His | Ile | His | Ala | Leu | Glu |
| | 610 | | | | | 615 | | | | 620 | | | | | |
| Leu | Val | Val | Ser | Arg | Asn | Leu | Ser | Pro | Pro | Asn | Cys | Thr | Glu | Leu | Gln |
| 625 | | | | | 630 | | | | | 635 | | | | | 640 |
| Ile | Asp | Ser | Cys | Ser | Ser | Ser | Glu | Glu | Ile | Lys | Lys | Lys | Lys | Tyr | Asn |
| | | | | 645 | | | | | 650 | | | | | 655 | |
| Gln | Met | Pro | Val | Arg | His | Ser | Arg | Asn | Leu | Gln | Leu | Met | Glu | Gly | Lys |
| | | | 660 | | | | | 665 | | | | | 670 | | |
| Glu | Pro | Ala | Thr | Gly | Ala | Lys | Lys | Ser | Asn | Lys | Pro | Asn | Glu | Gln | Thr |
| | | | 675 | | | | 680 | | | | | 685 | | | |
| Ser | Lys | Arg | His | Asp | Ser | Asp | Thr | Phe | Pro | Glu | Leu | Lys | Leu | Thr | Asn |
| | | 690 | | | | | 695 | | | | 700 | | | | |
| Ala | Pro | Gly | Ser | Phe | Thr | Lys | Cys | Ser | Asn | Thr | Ser | Glu | Leu | Lys | Glu |
| 705 | | | | | 710 | | | | | 715 | | | | | 720 |
| Phe | Val | Asn | Pro | Ser | Leu | Pro | Arg | Glu | Glu | Lys | Glu | Glu | Lys | Leu | Glu |
| | | | | 725 | | | | | 730 | | | | | 735 | |
| Thr | Val | Lys | Val | Ser | Asn | Asn | Ala | Glu | Asp | Pro | Lys | Asp | Leu | Met | Leu |
| | | | 740 | | | | | 745 | | | | | 750 | | |
| Ser | Gly | Glu | Arg | Val | Leu | Gln | Thr | Glu | Arg | Ser | Val | Glu | Ser | Ser | Ser |
| | | 755 | | | | | 760 | | | | | 765 | | | |
| Ile | Ser | Leu | Val | Pro | Gly | Thr | Asp | Tyr | Gly | Thr | Gln | Glu | Ser | Ile | Ser |
| | 770 | | | | | 775 | | | | | 780 | | | | |
| Leu | Leu | Glu | Val | Ser | Thr | Leu | Gly | Lys | Ala | Lys | Thr | Glu | Pro | Asn | Lys |
| 785 | | | | | 790 | | | | | 795 | | | | | 800 |
| Cys | Val | Ser | Gln | Cys | Ala | Ala | Phe | Glu | Asn | Pro | Lys | Gly | Leu | Ile | His |
| | | | | 805 | | | | | 810 | | | | | 815 | |
| Gly | Cys | Ser | Lys | Asp | Asn | Arg | Asn | Asp | Thr | Glu | Gly | Phe | Lys | Tyr | Pro |
| | | | 820 | | | | | 825 | | | | | 830 | | |
| Leu | Gly | His | Glu | Val | Asn | His | Ser | Arg | Glu | Thr | Ser | Ile | Glu | Met | Glu |
| | | 835 | | | | | 840 | | | | | 845 | | | |
| Glu | Ser | Glu | Leu | Asp | Ala | Gln | Tyr | Leu | Gln | Asn | Thr | Phe | Lys | Val | Ser |
| | 850 | | | | | 855 | | | | | 860 | | | | |
| Lys | Arg | Gln | Ser | Phe | Ala | Pro | Phe | Ser | Asn | Pro | Gly | Asn | Ala | Glu | Glu |
| 865 | | | | | 870 | | | | | 875 | | | | | 880 |
| Glu | Cys | Ala | Thr | Phe | Ser | Ala | His | Ser | Gly | Ser | Leu | Lys | Lys | Gln | Ser |
| | | | | 885 | | | | | 890 | | | | | 895 | |
| Pro | Lys | Val | Thr | Phe | Glu | Cys | Glu | Gln | Lys | Glu | Glu | Asn | Gln | Gly | Lys |
| | | | 900 | | | | | 905 | | | | | 910 | | |
| Asn | Glu | Ser | Asn | Ile | Lys | Pro | Val | Gln | Thr | Val | Asn | Ile | Thr | Ala | Gly |
| | | 915 | | | | | 920 | | | | | 925 | | | |
| Phe | Pro | Val | Val | Gly | Gln | Lys | Asp | Lys | Pro | Val | Asp | Asn | Ala | Lys | Cys |
| | 930 | | | | | 935 | | | | | 940 | | | | |
| Ser | Ile | Lys | Gly | Gly | Ser | Arg | Phe | Cys | Leu | Ser | Ser | Gln | Phe | Arg | Gly |
| 945 | | | | | 950 | | | | | 955 | | | | | 960 |
| Asn | Glu | Thr | Gly | Leu | Ile | Thr | Pro | Asn | Lys | His | Gly | Leu | Leu | Gln | Asn |
| | | | | 965 | | | | | 970 | | | | | 975 | |
| Pro | Tyr | Arg | Ile | Pro | Pro | Leu | Phe | Pro | Ile | Lys | Ser | Phe | Val | Lys | Thr |
| | | | 980 | | | | | 985 | | | | | 990 | | |

| Lys | Cys | Lys | Lys | Asn | Leu | Leu | Glu | Glu | Asn | Phe | Glu | Glu | His | Ser | Met |
|||||||||||||||||
| | | 995 | | | | | 1000 | | | | | 1005 | | | |

| Ser | Pro | Glu | Arg | Glu | Met | Gly | Asn | Glu | Asn | Ile | Pro | Ser | Thr | Val | Ser |
| | 1010 | | | | 1015 | | | | | 1020 | | | | | |

| Thr | Ile | Ser | Arg | Asn | Asn | Ile | Arg | Glu | Asn | Val | Phe | Lys | Glu | Ala | Ser |
| 1025 | | | | | 1030 | | | | | 1035 | | | | | 1040 |

| Ser | Ser | Asn | Ile | Asn | Glu | Val | Gly | Ser | Ser | Thr | Asn | Glu | Val | Gly | Ser |
| | | | | 1045 | | | | | 1050 | | | | | 1055 | |

| Ser | Ile | Asn | Glu | Ile | Gly | Ser | Ser | Asp | Glu | Asn | Ile | Gln | Ala | Glu | Leu |
| | | | 1060 | | | | | 1065 | | | | | 1070 | | |

| Gly | Arg | Asn | Arg | Gly | Pro | Lys | Leu | Asn | Ala | Met | Leu | Arg | Leu | Gly | Val |
| | | 1075 | | | | | 1080 | | | | | 1085 | | | |

| Leu | Gln | Pro | Glu | Val | Tyr | Lys | Gln | Ser | Leu | Pro | Gly | Ser | Asn | Cys | Lys |
| | | 1090 | | | | | 1095 | | | | | 1100 | | | |

| His | Pro | Glu | Ile | Lys | Lys | Gln | Glu | Tyr | Glu | Glu | Val | Val | Gln | Thr | Val |
| 1105 | | | | | 1110 | | | | | 1115 | | | | | 1120 |

| Asn | Thr | Asp | Phe | Ser | Pro | Tyr | Leu | Ile | Ser | Asp | Asn | Leu | Glu | Gln | Pro |
| | | | | 1125 | | | | | 1130 | | | | | 1135 | |

| Met | Gly | Ser | Ser | His | Ala | Ser | Gln | Val | Cys | Ser | Glu | Thr | Pro | Asp | Asp |
| | | | 1140 | | | | | 1145 | | | | | 1150 | | |

| Leu | Leu | Asp | Asp | Gly | Glu | Ile | Lys | Glu | Asp | Thr | Ser | Phe | Ala | Glu | Asn |
| | | 1155 | | | | | 1160 | | | | | 1165 | | | |

| Asp | Ile | Lys | Glu | Ser | Ser | Ala | Val | Phe | Ser | Lys | Ser | Val | Gln | Lys | Gly |
| | | 1170 | | | | | 1175 | | | | | 1180 | | | |

| Glu | Leu | Ser | Arg | Ser | Pro | Ser | Pro | Phe | Thr | His | Thr | His | Leu | Ala | Gln |
| 1185 | | | | | 1190 | | | | | 1195 | | | | | 1200 |

| Gly | Tyr |

( 2 ) INFORMATION FOR SEQ ID NO:23:

( i ) SEQUENCE CHARACTERISTICS:
        ( A ) LENGTH: 1363 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

| Met | Asp | Leu | Ser | Ala | Leu | Arg | Val | Glu | Glu | Val | Gln | Asn | Val | Ile | Asn |
| 1 | | | | 5 | | | | | 10 | | | | | 15 | |

| Ala | Met | Gln | Lys | Ile | Leu | Glu | Cys | Pro | Ile | Cys | Leu | Glu | Leu | Ile | Lys |
| | | | 20 | | | | | 25 | | | | | 30 | | |

| Glu | Pro | Val | Ser | Thr | Lys | Cys | Asp | His | Ile | Phe | Cys | Lys | Phe | Cys | Met |
| | | | 35 | | | | | 40 | | | | | 45 | | |

| Leu | Lys | Leu | Leu | Asn | Gln | Lys | Lys | Gly | Pro | Ser | Gln | Cys | Pro | Leu | Cys |
| | | 50 | | | | | 55 | | | | | 60 | | | |

| Lys | Asn | Asp | Ile | Thr | Lys | Arg | Ser | Leu | Gln | Glu | Ser | Thr | Arg | Phe | Ser |
| 65 | | | | | 70 | | | | | 75 | | | | | 80 |

| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |

| Thr | Gly | Leu | Glu | Tyr | Ala | Asn | Ser | Tyr | Asn | Phe | Ala | Lys | Lys | Glu | Asn |
| | | | 100 | | | | | 105 | | | | | 110 | | |

| Asn | Ser | Pro | Glu | His | Leu | Lys | Asp | Glu | Val | Ser | Ile | Ile | Gln | Ser | Met |
| | | | 115 | | | | | 120 | | | | | 125 | | |

| Gly | Tyr | Arg | Asn | Arg | Ala | Lys | Arg | Leu | Leu | Gln | Ser | Glu | Pro | Glu | Asn |

```
                    130                         135                         140
Pro  Ser  Leu  Gln  Glu  Thr  Ser  Leu  Ser  Val  Gln  Leu  Ser  Asn  Leu  Gly
145                      150                      155                      160
Thr  Val  Arg  Thr  Leu  Arg  Thr  Lys  Gln  Arg  Ile  Gln  Pro  Gln  Lys  Thr
                    165                      170                      175
Ser  Val  Tyr  Ile  Glu  Leu  Gly  Ser  Asp  Ser  Ser  Glu  Asp  Thr  Val  Asn
               180                      185                      190
Lys  Ala  Thr  Tyr  Cys  Ser  Val  Gly  Asp  Gln  Glu  Leu  Leu  Gln  Ile  Thr
          195                      200                      205
Pro  Gln  Gly  Thr  Arg  Asp  Glu  Ile  Ser  Leu  Asp  Ser  Ala  Lys  Lys  Ala
     210                      215                      220
Ala  Cys  Glu  Phe  Ser  Glu  Thr  Asp  Val  Thr  Asn  Thr  Glu  His  His  Gln
225                      230                      235                      240
Pro  Ser  Asn  Asn  Asp  Leu  Asn  Thr  Thr  Glu  Lys  Arg  Ala  Ala  Glu  Arg
                    245                      250                      255
His  Pro  Glu  Lys  Tyr  Gln  Gly  Ser  Ser  Val  Ser  Asn  Leu  His  Val  Glu
               260                      265                      270
Pro  Cys  Gly  Thr  Asn  Thr  His  Ala  Ser  Ser  Leu  Gln  His  Glu  Asn  Ser
          275                      280                      285
Ser  Leu  Leu  Leu  Thr  Lys  Asp  Arg  Met  Asn  Val  Glu  Lys  Ala  Glu  Phe
     290                      295                      300
Cys  Asn  Lys  Ser  Lys  Gln  Pro  Gly  Leu  Ala  Arg  Ser  Gln  His  Asn  Arg
305                      310                      315                      320
Trp  Ala  Gly  Ser  Lys  Glu  Thr  Cys  Asn  Asp  Arg  Arg  Thr  Pro  Ser  Thr
                    325                      330                      335
Glu  Lys  Lys  Val  Asp  Leu  Asn  Ala  Asp  Pro  Leu  Cys  Glu  Arg  Lys  Glu
               340                      345                      350
Trp  Asn  Lys  Gln  Lys  Leu  Pro  Cys  Ser  Glu  Asn  Pro  Arg  Asp  Thr  Glu
          355                      360                      365
Asp  Val  Pro  Trp  Ile  Thr  Leu  Asn  Ser  Ser  Ile  Gln  Lys  Val  Asn  Glu
     370                      375                      380
Trp  Phe  Ser  Arg  Ser  Asp  Glu  Leu  Leu  Gly  Ser  Asp  Asp  Ser  His  Asp
385                      390                      395                      400
Gly  Glu  Ser  Glu  Ser  Asn  Ala  Lys  Val  Ala  Asp  Val  Leu  Asp  Val  Leu
                    405                      410                      415
Asn  Glu  Val  Asp  Glu  Tyr  Ser  Gly  Ser  Ser  Glu  Lys  Ile  Asp  Leu  Leu
               420                      425                      430
Ala  Ser  Asp  Pro  His  Glu  Ala  Leu  Ile  Cys  Lys  Ser  Glu  Arg  Val  His
          435                      440                      445
Ser  Lys  Ser  Val  Glu  Ser  Asn  Ile  Glu  Asp  Lys  Ile  Phe  Gly  Lys  Thr
     450                      455                      460
Tyr  Arg  Lys  Lys  Ala  Ser  Leu  Pro  Asn  Leu  Ser  His  Val  Thr  Glu  Asn
465                      470                      475                      480
Leu  Ile  Ile  Gly  Ala  Phe  Val  Thr  Glu  Pro  Gln  Ile  Ile  Gln  Glu  Arg
                    485                      490                      495
Pro  Leu  Thr  Asn  Lys  Leu  Lys  Arg  Lys  Arg  Arg  Pro  Thr  Ser  Gly  Leu
               500                      505                      510
His  Pro  Glu  Asp  Phe  Ile  Lys  Lys  Ala  Asp  Leu  Ala  Val  Gln  Lys  Thr
          515                      520                      525
Pro  Glu  Met  Ile  Asn  Gln  Gly  Thr  Asn  Gln  Thr  Glu  Gln  Asn  Gly  Gln
     530                      535                      540
Val  Met  Asn  Ile  Thr  Asn  Ser  Gly  His  Glu  Asn  Lys  Thr  Lys  Gly  Asp
545                      550                      555                      560
```

-continued

| | | | | | | | | | | | | | |
|---|---|---|---|---|---|---|---|---|---|---|---|---|---|
| Ser | Ile | Gln | Asn 565 | Glu | Lys | Asn | Pro | Asn 570 | Pro | Ile | Glu | Ser | Leu | Glu 575 | Lys |
| Glu | Ser | Ala | Phe 580 | Lys | Thr | Lys | Ala | Glu 585 | Pro | Ile | Ser | Ser | Ser 590 | Ile | Ser |
| Asn | Met | Glu 595 | Leu | Glu | Leu | Asn | Ile 600 | His | Asn | Ser | Lys | Ala 605 | Pro | Lys | Lys |
| Asn | Arg 610 | Leu | Arg | Arg | Lys | Ser 615 | Ser | Thr | Arg | His | Ile 620 | His | Ala | Leu | Glu |
| Leu 625 | Val | Val | Ser | Arg | Asn 630 | Leu | Ser | Pro | Pro | Asn 635 | Cys | Thr | Glu | Leu | Gln 640 |
| Ile | Asp | Ser | Cys | Ser 645 | Ser | Ser | Glu | Glu | Ile 650 | Lys | Lys | Lys | Lys | Tyr 655 | Asn |
| Gln | Met | Pro | Val 660 | Arg | His | Ser | Arg | Asn 665 | Leu | Gln | Leu | Met | Glu 670 | Gly | Lys |
| Glu | Pro | Ala 675 | Thr | Gly | Ala | Lys | Lys 680 | Ser | Asn | Lys | Pro | Asn 685 | Glu | Gln | Thr |
| Ser | Lys 690 | Arg | His | Asp | Ser | Asp 695 | Thr | Phe | Pro | Glu | Leu 700 | Lys | Leu | Thr | Asn |
| Ala 705 | Pro | Gly | Ser | Phe | Thr 710 | Lys | Cys | Ser | Asn | Thr 715 | Ser | Glu | Leu | Lys | Glu 720 |
| Phe | Val | Asn | Pro | Ser 725 | Leu | Pro | Arg | Glu | Glu 730 | Lys | Glu | Glu | Lys | Leu 735 | Glu |
| Thr | Val | Lys | Val 740 | Ser | Asn | Asn | Ala | Glu 745 | Asp | Pro | Lys | Asp | Leu 750 | Met | Leu |
| Ser | Gly | Glu 755 | Arg | Val | Leu | Gln | Thr 760 | Glu | Arg | Ser | Val | Glu 765 | Ser | Ser | Ser |
| Ile | Ser 770 | Leu | Val | Pro | Gly | Thr 775 | Asp | Tyr | Gly | Thr | Gln 780 | Glu | Ser | Ile | Ser |
| Leu 785 | Leu | Glu | Val | Ser | Thr 790 | Leu | Gly | Lys | Ala | Lys 795 | Thr | Glu | Pro | Asn | Lys 800 |
| Cys | Val | Ser | Gln | Cys 805 | Ala | Ala | Phe | Glu | Asn 810 | Pro | Lys | Gly | Leu | Ile 815 | His |
| Gly | Cys | Ser | Lys 820 | Asp | Asn | Arg | Asn | Asp 825 | Thr | Glu | Gly | Phe | Lys 830 | Tyr | Pro |
| Leu | Gly | His 835 | Glu | Val | Asn | His | Ser 840 | Arg | Glu | Thr | Ser | Ile 845 | Glu | Met | Glu |
| Glu | Ser | Glu 850 | Leu | Asp | Ala | Gln | Tyr 855 | Leu | Gln | Asn | Thr | Phe 860 | Lys | Val | Ser |
| Lys 865 | Arg | Gln | Ser | Phe | Ala 870 | Pro | Phe | Ser | Asn | Pro 875 | Gly | Asn | Ala | Glu | Glu 880 |
| Glu | Cys | Ala | Thr | Phe 885 | Ser | Ala | His | Ser | Gly 890 | Ser | Leu | Lys | Lys | Gln 895 | Ser |
| Pro | Lys | Val | Thr 900 | Phe | Glu | Cys | Glu | Gln 905 | Lys | Glu | Glu | Asn | Gln 910 | Gly | Lys |
| Asn | Glu | Ser 915 | Asn | Ile | Lys | Pro | Val 920 | Gln | Thr | Val | Asn | Ile 925 | Thr | Ala | Gly |
| Phe | Pro 930 | Val | Val | Gly | Gln | Lys 935 | Asp | Lys | Pro | Val | Asp 940 | Asn | Ala | Lys | Cys |
| Ser 945 | Ile | Lys | Gly | Gly | Ser 950 | Arg | Phe | Cys | Leu | Ser 955 | Ser | Gln | Phe | Arg | Gly 960 |
| Asn | Glu | Thr | Gly | Leu 965 | Ile | Thr | Pro | Asn | Lys 970 | His | Gly | Leu | Leu | Gln 975 | Asn |
| Pro | Tyr | Arg | Ile 980 | Pro | Pro | Leu | Phe | Pro 985 | Ile | Lys | Ser | Phe | Val 990 | Lys | Thr |

-continued

| | | | | | | | | | | | | | |
|---|---|---|---|---|---|---|---|---|---|---|---|---|---|
|Lys|Cys|Lys|Lys|Asn|Leu|Leu|Glu|Glu|Asn|Phe|Glu|Glu|His|Ser|Met|
| | |995| | | |1000| | | |1005| | | |
|Ser|Pro|Glu|Arg|Glu|Met|Gly|Asn|Glu|Asn|Ile|Pro|Ser|Thr|Val|Ser|
| | |1010| | | |1015| | | |1020| | | |
|Thr|Ile|Ser|Arg|Asn|Asn|Ile|Arg|Glu|Asn|Val|Phe|Lys|Glu|Ala|Ser|
|1025| | | | |1030| | | | |1035| | | | |1040|
|Ser|Ser|Asn|Ile|Asn|Glu|Val|Gly|Ser|Ser|Thr|Asn|Glu|Val|Gly|Ser|
| | | |1045| | | |1050| | | | |1055| |
|Ser|Ile|Asn|Glu|Ile|Gly|Ser|Ser|Asp|Glu|Asn|Ile|Gln|Ala|Glu|Leu|
| | |1060| | | |1065| | | |1070| | | |
|Gly|Arg|Asn|Arg|Gly|Pro|Lys|Leu|Asn|Ala|Met|Leu|Arg|Leu|Gly|Val|
| | |1075| | | |1080| | | |1085| | | |
|Leu|Gln|Pro|Glu|Val|Tyr|Lys|Gln|Ser|Leu|Pro|Gly|Ser|Asn|Cys|Lys|
| | |1090| | | |1095| | | |1100| | | |
|His|Pro|Glu|Ile|Lys|Lys|Gln|Glu|Tyr|Glu|Glu|Val|Val|Gln|Thr|Val|
|1105| | | | |1110| | | | |1115| | | | |1120|
|Asn|Thr|Asp|Phe|Ser|Pro|Tyr|Leu|Ile|Ser|Asp|Asn|Leu|Glu|Gln|Pro|
| | | |1125| | | |1130| | | | |1135| |
|Met|Gly|Ser|Ser|His|Ala|Ser|Gln|Val|Cys|Ser|Glu|Thr|Pro|Asp|Asp|
| | | |1140| | | |1145| | | | |1150| |
|Leu|Leu|Asp|Asp|Gly|Glu|Ile|Lys|Glu|Asp|Thr|Ser|Phe|Ala|Glu|Asn|
| | | |1155| | | |1160| | | | |1165| |
|Asp|Ile|Lys|Glu|Ser|Ser|Ala|Val|Phe|Ser|Lys|Ser|Val|Gln|Lys|Gly|
| | |1170| | | |1175| | | |1180| | | |
|Glu|Leu|Ser|Arg|Ser|Pro|Ser|Pro|Phe|Thr|His|Thr|His|Leu|Ala|Gln|
|1185| | | | |1190| | | | |1195| | | | |1200|
|Gly|Tyr|Arg|Arg|Gly|Ala|Lys|Lys|Leu|Glu|Ser|Ser|Glu|Glu|Asn|Leu|
| | | |1205| | | |1210| | | | |1215| |
|Ser|Ser|Glu|Asp|Glu|Glu|Leu|Pro|Cys|Phe|Gln|His|Leu|Leu|Phe|Gly|
| | | |1220| | | |1225| | | | |1230| |
|Lys|Val|Asn|Asn|Ile|Pro|Ser|Gln|Ser|Thr|Arg|His|Ser|Thr|Val|Ala|
| | | |1235| | | |1240| | | | |1245| |
|Thr|Glu|Cys|Leu|Ser|Lys|Asn|Thr|Glu|Glu|Asn|Leu|Leu|Ser|Leu|Lys|
| | |1250| | | |1255| | | |1260| | | |
|Asn|Ser|Leu|Asn|Asp|Cys|Ser|Asn|Gln|Val|Ile|Leu|Ala|Lys|Ala|Ser|
|1265| | | | |1270| | | | |1275| | | | |1280|
|Gln|Glu|His|His|Leu|Ser|Glu|Glu|Thr|Lys|Cys|Ser|Ala|Ser|Leu|Phe|
| | | | |1285| | | | |1290| | | | |1295|
|Ser|Ser|Gln|Cys|Ser|Glu|Leu|Glu|Asp|Leu|Thr|Ala|Asn|Thr|Asn|Thr|
| | | |1300| | | |1305| | | | |1310| |
|Gln|Asp|Pro|Phe|Leu|Ile|Gly|Ser|Ser|Lys|Gln|Met|Arg|His|Gln|Ser|
| | |1315| | | |1320| | | |1325| | | |
|Glu|Ser|Gln|Gly|Val|Gly|Leu|Ser|Asp|Lys|Glu|Leu|Val|Ser|Asp|Asp|
| | |1330| | | |1335| | | |1340| | | |
|Glu|Glu|Arg|Gly|Thr|Gly|Leu|Glu|Glu|Asn|Lys|Lys|Ser|Lys|Ala|Trp|
|1345| | | | |1350| | | | |1355| | | | |1360|
|Ile|Gln|Thr| | | | | | | | | | | | | |

( 2 ) INFORMATION FOR SEQ ID NO:24:

( i ) SEQUENCE CHARACTERISTICS:
    ( A ) LENGTH: 1852 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:24:

| Met | Asp | Leu | Ser | Ala | Leu | Arg | Val | Glu | Glu | Val | Gln | Asn | Val | Ile | Asn |
|---|---|---|---|---|---|---|---|---|---|---|---|---|---|---|---|
| 1 | | | | 5 | | | | | 10 | | | | | 15 | |

| Ala | Met | Gln | Lys | Ile | Leu | Glu | Cys | Pro | Ile | Cys | Leu | Glu | Leu | Ile | Lys |
|---|---|---|---|---|---|---|---|---|---|---|---|---|---|---|---|
| | | | 20 | | | | | 25 | | | | | 30 | | |

| Glu | Pro | Val | Ser | Thr | Lys | Cys | Asp | His | Ile | Phe | Cys | Lys | Phe | Cys | Met |
|---|---|---|---|---|---|---|---|---|---|---|---|---|---|---|---|
| | | | 35 | | | | 40 | | | | | 45 | | | |

| Leu | Lys | Leu | Leu | Asn | Gln | Lys | Gly | Pro | Ser | Gln | Cys | Pro | Leu | Cys |
|---|---|---|---|---|---|---|---|---|---|---|---|---|---|---|
| | 50 | | | | | 55 | | | | | 60 | | | |

| Lys | Asn | Asp | Ile | Thr | Lys | Arg | Ser | Leu | Gln | Glu | Ser | Thr | Arg | Phe | Ser |
|---|---|---|---|---|---|---|---|---|---|---|---|---|---|---|---|
| 65 | | | | | 70 | | | | | 75 | | | | | 80 |

| Gln | Leu | Val | Glu | Glu | Leu | Leu | Lys | Ile | Ile | Cys | Ala | Phe | Gln | Leu | Asp |
|---|---|---|---|---|---|---|---|---|---|---|---|---|---|---|---|
| | | | | 85 | | | | | 90 | | | | | 95 | |

| Thr | Gly | Leu | Glu | Tyr | Ala | Asn | Ser | Tyr | Asn | Phe | Ala | Lys | Lys | Glu | Asn |
|---|---|---|---|---|---|---|---|---|---|---|---|---|---|---|---|
| | | | 100 | | | | | 105 | | | | | 110 | | |

| Asn | Ser | Pro | Glu | His | Leu | Lys | Asp | Glu | Val | Ser | Ile | Ile | Gln | Ser | Met |
|---|---|---|---|---|---|---|---|---|---|---|---|---|---|---|---|
| | | | 115 | | | | 120 | | | | | 125 | | | |

| Gly | Tyr | Arg | Asn | Arg | Ala | Lys | Arg | Leu | Leu | Gln | Ser | Glu | Pro | Glu | Asn |
|---|---|---|---|---|---|---|---|---|---|---|---|---|---|---|---|
| | 130 | | | | | 135 | | | | | 140 | | | | |

| Pro | Ser | Leu | Gln | Glu | Thr | Ser | Leu | Ser | Val | Gln | Leu | Ser | Asn | Leu | Gly |
|---|---|---|---|---|---|---|---|---|---|---|---|---|---|---|---|
| 145 | | | | | 150 | | | | | 155 | | | | | 160 |

| Thr | Val | Arg | Thr | Leu | Arg | Thr | Lys | Gln | Arg | Ile | Gln | Pro | Gln | Lys | Thr |
|---|---|---|---|---|---|---|---|---|---|---|---|---|---|---|---|
| | | | | 165 | | | | | 170 | | | | | 175 | |

| Ser | Val | Tyr | Ile | Glu | Leu | Gly | Ser | Asp | Ser | Ser | Glu | Asp | Thr | Val | Asn |
|---|---|---|---|---|---|---|---|---|---|---|---|---|---|---|---|
| | | | 180 | | | | | 185 | | | | | 190 | | |

| Lys | Ala | Thr | Tyr | Cys | Ser | Val | Gly | Asp | Gln | Glu | Leu | Leu | Gln | Ile | Thr |
|---|---|---|---|---|---|---|---|---|---|---|---|---|---|---|---|
| | | 195 | | | | | 200 | | | | | 205 | | | |

| Pro | Gln | Gly | Thr | Arg | Asp | Glu | Ile | Ser | Leu | Asp | Ser | Ala | Lys | Lys | Ala |
|---|---|---|---|---|---|---|---|---|---|---|---|---|---|---|---|
| | 210 | | | | | 215 | | | | | 220 | | | | |

| Ala | Cys | Glu | Phe | Ser | Glu | Thr | Asp | Val | Thr | Asn | Thr | Glu | His | His | Gln |
|---|---|---|---|---|---|---|---|---|---|---|---|---|---|---|---|
| 225 | | | | | 230 | | | | | 235 | | | | | 240 |

| Pro | Ser | Asn | Asn | Asp | Leu | Asn | Thr | Thr | Glu | Lys | Arg | Ala | Ala | Glu | Arg |
|---|---|---|---|---|---|---|---|---|---|---|---|---|---|---|---|
| | | | | 245 | | | | | 250 | | | | | 255 | |

| His | Pro | Glu | Lys | Tyr | Gln | Gly | Ser | Ser | Val | Ser | Asn | Leu | His | Val | Glu |
|---|---|---|---|---|---|---|---|---|---|---|---|---|---|---|---|
| | | | 260 | | | | | 265 | | | | | 270 | | |

| Pro | Cys | Gly | Thr | Asn | Thr | His | Ala | Ser | Ser | Leu | Gln | His | Glu | Asn | Ser |
|---|---|---|---|---|---|---|---|---|---|---|---|---|---|---|---|
| | | 275 | | | | | 280 | | | | | 285 | | | |

| Ser | Leu | Leu | Leu | Thr | Lys | Asp | Arg | Met | Asn | Val | Glu | Lys | Ala | Glu | Phe |
|---|---|---|---|---|---|---|---|---|---|---|---|---|---|---|---|
| | 290 | | | | | 295 | | | | | 300 | | | | |

| Cys | Asn | Lys | Ser | Lys | Gln | Pro | Gly | Leu | Ala | Arg | Ser | Gln | His | Asn | Arg |
|---|---|---|---|---|---|---|---|---|---|---|---|---|---|---|---|
| 305 | | | | | 310 | | | | | 315 | | | | | 320 |

| Trp | Ala | Gly | Ser | Lys | Glu | Thr | Cys | Asn | Asp | Arg | Arg | Thr | Pro | Ser | Thr |
|---|---|---|---|---|---|---|---|---|---|---|---|---|---|---|---|
| | | | 325 | | | | | 330 | | | | | 335 | | |

| Glu | Lys | Lys | Val | Asp | Leu | Asn | Ala | Asp | Pro | Leu | Cys | Glu | Arg | Lys | Glu |
|---|---|---|---|---|---|---|---|---|---|---|---|---|---|---|---|
| | | | 340 | | | | | 345 | | | | | 350 | | |

| Trp | Asn | Lys | Gln | Lys | Leu | Pro | Cys | Ser | Glu | Asn | Pro | Arg | Asp | Thr | Glu |
|---|---|---|---|---|---|---|---|---|---|---|---|---|---|---|---|
| | | 355 | | | | | 360 | | | | | 365 | | | |

| Asp | Val | Pro | Trp | Ile | Thr | Leu | Asn | Ser | Ser | Ile | Gln | Lys | Val | Asn | Glu |
|---|---|---|---|---|---|---|---|---|---|---|---|---|---|---|---|
| | 370 | | | | | 375 | | | | | 380 | | | | |

| Trp | Phe | Ser | Arg | Ser | Asp | Glu | Leu | Leu | Gly | Ser | Asp | Ser | His | Asp |
|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
| Gly | Glu | Ser | Glu | Ser | Asn | Ala | Lys | Val | Ala | Asp | Val | Leu | Asp | Val | Leu |
| | | | | 405 | | | | | 410 | | | | | 415 | |
| Asn | Glu | Val | Asp | Glu | Tyr | Ser | Gly | Ser | Ser | Glu | Lys | Ile | Asp | Leu | Leu |
| | | | 420 | | | | | 425 | | | | | 430 | | |
| Ala | Ser | Asp | Pro | His | Glu | Ala | Leu | Ile | Cys | Lys | Ser | Glu | Arg | Val | His |
| | | | 435 | | | | | 440 | | | | | 445 | | |
| Ser | Lys | Ser | Val | Glu | Ser | Asn | Ile | Glu | Asp | Lys | Ile | Phe | Gly | Lys | Thr |
| | | 450 | | | | | 455 | | | | | 460 | | | |
| Tyr | Arg | Lys | Lys | Ala | Ser | Leu | Pro | Asn | Leu | Ser | His | Val | Thr | Glu | Asn |
| 465 | | | | | | 470 | | | | | 475 | | | | 480 |
| Leu | Ile | Ile | Gly | Ala | Phe | Val | Thr | Glu | Pro | Gln | Ile | Ile | Gln | Glu | Arg |
| | | | | 485 | | | | | 490 | | | | | 495 | |
| Pro | Leu | Thr | Asn | Lys | Leu | Lys | Arg | Lys | Arg | Arg | Pro | Thr | Ser | Gly | Leu |
| | | | 500 | | | | | 505 | | | | | 510 | | |
| His | Pro | Glu | Asp | Phe | Ile | Lys | Lys | Ala | Asp | Leu | Ala | Val | Gln | Lys | Thr |
| | | | 515 | | | | | 520 | | | | | 525 | | |
| Pro | Glu | Met | Ile | Asn | Gln | Gly | Thr | Asn | Gln | Thr | Glu | Gln | Asn | Gly | Gln |
| | | 530 | | | | | 535 | | | | | 540 | | | |
| Val | Met | Asn | Ile | Thr | Asn | Ser | Gly | His | Glu | Asn | Lys | Thr | Lys | Gly | Asp |
| 545 | | | | | 550 | | | | | 555 | | | | | 560 |
| Ser | Ile | Gln | Asn | Glu | Lys | Asn | Pro | Asn | Pro | Ile | Glu | Ser | Leu | Glu | Lys |
| | | | | 565 | | | | | 570 | | | | | 575 | |
| Glu | Ser | Ala | Phe | Lys | Thr | Lys | Ala | Glu | Pro | Ile | Ser | Ser | Ser | Ile | Ser |
| | | | 580 | | | | | 585 | | | | | 590 | | |
| Asn | Met | Glu | Leu | Glu | Leu | Asn | Ile | His | Asn | Ser | Lys | Ala | Pro | Lys | Lys |
| | | 595 | | | | | 600 | | | | | 605 | | | |
| Asn | Arg | Leu | Arg | Arg | Lys | Ser | Ser | Thr | Arg | His | Ile | His | Ala | Leu | Glu |
| | 610 | | | | | 615 | | | | | 620 | | | | |
| Leu | Val | Val | Ser | Arg | Asn | Leu | Ser | Pro | Pro | Asn | Cys | Thr | Glu | Leu | Gln |
| 625 | | | | | 630 | | | | | 635 | | | | | 640 |
| Ile | Asp | Ser | Cys | Ser | Ser | Ser | Glu | Glu | Ile | Lys | Lys | Lys | Lys | Tyr | Asn |
| | | | | 645 | | | | | 650 | | | | | 655 | |
| Gln | Met | Pro | Val | Arg | His | Ser | Arg | Asn | Leu | Gln | Leu | Met | Glu | Gly | Lys |
| | | | 660 | | | | | 665 | | | | | 670 | | |
| Glu | Pro | Ala | Thr | Gly | Ala | Lys | Lys | Ser | Asn | Lys | Pro | Asn | Glu | Gln | Thr |
| | | | 675 | | | | | 680 | | | | | 685 | | |
| Ser | Lys | Arg | His | Asp | Ser | Asp | Thr | Phe | Pro | Glu | Leu | Lys | Leu | Thr | Asn |
| | 690 | | | | | 695 | | | | | 700 | | | | |
| Ala | Pro | Gly | Ser | Phe | Thr | Lys | Cys | Ser | Asn | Thr | Ser | Glu | Leu | Lys | Glu |
| 705 | | | | | 710 | | | | | 715 | | | | | 720 |
| Phe | Val | Asn | Pro | Ser | Leu | Pro | Arg | Glu | Glu | Lys | Glu | Glu | Lys | Leu | Glu |
| | | | | 725 | | | | | 730 | | | | | 735 | |
| Thr | Val | Lys | Val | Ser | Asn | Asn | Ala | Glu | Asp | Pro | Lys | Asp | Leu | Met | Leu |
| | | | 740 | | | | | 745 | | | | | 750 | | |
| Ser | Gly | Glu | Arg | Val | Leu | Gln | Thr | Glu | Arg | Ser | Val | Glu | Ser | Ser | Ser |
| | | 755 | | | | | 760 | | | | | 765 | | | |
| Ile | Ser | Leu | Val | Pro | Gly | Thr | Asp | Tyr | Gly | Thr | Gln | Glu | Ser | Ile | Ser |
| | 770 | | | | | 775 | | | | | 780 | | | | |
| Leu | Leu | Glu | Val | Ser | Thr | Leu | Gly | Lys | Ala | Lys | Thr | Glu | Pro | Asn | Lys |
| 785 | | | | | 790 | | | | | 795 | | | | | 800 |
| Cys | Val | Ser | Gln | Cys | Ala | Ala | Phe | Glu | Asn | Pro | Lys | Gly | Leu | Ile | His |
| | | | | 805 | | | | | 810 | | | | | 815 | |
| Gly | Cys | Ser | Lys | Asp | Asn | Arg | Asn | Asp | Thr | Glu | Gly | Phe | Lys | Tyr | Pro |
| | | | 820 | | | | | 825 | | | | | 830 | | |

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
            885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
            1045                1050                1055

Ser Ile Asn Glu Ile Gly Ser Ser Asp Glu Asn Ile Gln Ala Glu Leu
            1060                1065                1070

Gly Arg Asn Arg Gly Pro Lys Leu Asn Ala Met Leu Arg Leu Gly Val
            1075                1080                1085

Leu Gln Pro Glu Val Tyr Lys Gln Ser Leu Pro Gly Ser Asn Cys Lys
    1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
            1125                1130                1135

Met Gly Ser Ser His Ala Ser Gln Val Cys Ser Glu Thr Pro Asp Asp
            1140                1145                1150

Leu Leu Asp Asp Gly Glu Ile Lys Glu Asp Thr Ser Phe Ala Glu Asn
            1155                1160                1165

Asp Ile Lys Glu Ser Ser Ala Val Phe Ser Lys Ser Val Gln Lys Gly
    1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
            1205                1210                1215

Ser Ser Glu Asp Glu Glu Leu Pro Cys Phe Gln His Leu Leu Phe Gly
            1220                1225                1230

Lys Val Asn Asn Ile Pro Ser Gln Ser Thr Arg His Ser Thr Val Ala
        1235                1240                1245

Thr Glu Cys Leu Ser Lys Asn Thr Glu Glu Asn Leu Leu Ser Leu Lys

|  |  |  |
|---|---|---|
| 1250 | 1255 | 1260 |

Asn Ser Leu Asn Asp Cys Ser Asn Gln Val Ile Leu Ala Lys Ala Ser
1265             1270            1275                   1280

Gln Glu His His Leu Ser Glu Glu Thr Lys Cys Ser Ala Ser Leu Phe
                1285            1290            1295

Ser Ser Gln Cys Ser Glu Leu Glu Asp Leu Thr Ala Asn Thr Asn Thr
            1300            1305            1310

Gln Asp Pro Phe Leu Ile Gly Ser Ser Lys Gln Met Arg His Gln Ser
            1315            1320            1325

Glu Ser Gln Gly Val Gly Leu Ser Asp Lys Glu Leu Val Ser Asp Asp
            1330            1335            1340

Glu Glu Arg Gly Thr Gly Leu Glu Glu Asn Asn Gln Glu Gln Gln Ser
1345            1350            1355            1360

Met Asp Ser Asn Leu Gly Glu Ala Ala Ser Gly Cys Glu Ser Glu Thr
                1365            1370            1375

Ser Val Ser Glu Asp Cys Ser Gly Leu Ser Ser Gln Ser Asp Ile Leu
            1380            1385            1390

Thr Thr Gln Gln Arg Asp Thr Met Gln His Asn Leu Ile Lys Leu Gln
            1395            1400            1405

Gln Glu Met Ala Glu Leu Glu Ala Val Leu Glu Gln His Gly Ser Gln
1410            1415            1420

Pro Ser Asn Ser Tyr Pro Ser Ile Ile Ser Asp Ser Ser Ala Leu Glu
1425            1430            1435            1440

Asp Leu Arg Asn Pro Glu Gln Ser Thr Ser Glu Lys Ala Val Leu Thr
            1445            1450            1455

Ser Gln Lys Ser Ser Glu Tyr Pro Ile Ser Gln Asn Pro Glu Gly Leu
            1460            1465            1470

Ser Ala Asp Lys Phe Glu Val Ser Ala Asp Ser Ser Thr Ser Lys Asn
            1475            1480            1485

Lys Glu Pro Gly Val Glu Arg Ser Ser Pro Ser Lys Cys Pro Ser Leu
            1490            1495            1500

Asp Asp Arg Trp Tyr Met His Ser Cys Ser Gly Ser Leu Gln Asn Arg
1505            1510            1515            1520

Asn Tyr Pro Ser Gln Glu Glu Leu Ile Lys Val Val Asp Val Glu Glu
            1525            1530            1535

Gln Gln Leu Glu Glu Ser Gly Pro His Asp Leu Thr Glu Thr Ser Tyr
            1540            1545            1550

Leu Pro Arg Gln Asp Leu Glu Gly Thr Pro Tyr Leu Glu Ser Gly Ile
            1555            1560            1565

Ser Leu Phe Ser Asp Asp Pro Glu Ser Asp Pro Ser Glu Asp Arg Ala
            1570            1575            1580

Pro Glu Ser Ala Arg Val Gly Asn Ile Pro Ser Ser Thr Ser Ala Leu
1585            1590            1595            1600

Lys Val Pro Gln Leu Lys Val Ala Glu Ser Ala Gln Ser Pro Ala Ala
                1605            1610            1615

Ala His Thr Thr Asp Thr Ala Gly Tyr Asn Ala Met Glu Glu Ser Val
            1620            1625            1630

Ser Arg Glu Lys Pro Glu Leu Thr Ala Ser Thr Glu Arg Val Asn Lys
            1635            1640            1645

Arg Met Ser Met Val Val Ser Gly Leu Thr Pro Glu Glu Phe Met Leu
            1650            1655            1660

Val Tyr Lys Phe Ala Arg Lys His His Ile Thr Leu Thr Asn Leu Ile
1665            1670            1675            1680

| | | | | | | | | | | | | | | |
|---|---|---|---|---|---|---|---|---|---|---|---|---|---|---|
| Thr | Glu | Glu | Thr | Thr 1685 | His | Val | Val | Met | Lys 1690 | Thr | Asp | Ala | Glu | Phe Val 1695 |
| Cys | Glu | Arg | Thr 1700 | Leu | Lys | Tyr | Phe | Leu 1705 | Gly | Ile | Ala | Gly | Gly 1710 | Lys Trp |
| Val | Val | Ser | Tyr 1715 | Phe | Trp | Val | Thr | Gln 1720 | Ser | Ile | Lys | Glu | Arg 1725 | Lys Met |
| Leu | Asn 1730 | Glu | His | Asp | Phe | Glu 1735 | Val | Arg | Gly | Asp | Val 1740 | Val | Asn | Gly Arg |
| Asn 1745 | His | Gln | Gly | Pro | Lys 1750 | Arg | Ala | Arg | Glu | Ser 1755 | Gln | Asp | Arg | Lys Ile 1760 |
| Phe | Arg | Gly | Leu | Glu 1765 | Ile | Cys | Cys | Tyr | Gly 1770 | Pro | Phe | Thr | Asn | Met Pro 1775 |
| Thr | Asp | Gln | Leu 1780 | Glu | Trp | Met | Val | Gln 1785 | Leu | Cys | Gly | Ala | Ser 1790 | Val Val |
| Lys | Glu | Leu 1795 | Ser | Ser | Phe | Thr | Leu 1800 | Gly | Thr | Gly | Val | His 1805 | Pro | Ile Val |
| Val | Val 1810 | Gln | Pro | Asp | Ala | Trp 1815 | Thr | Glu | Asp | Asn | Gly 1820 | Phe | His | Ala Ile |
| Gly 1825 | Gln | Met | Cys | Glu | Ala 1830 | Pro | Val | Val | Thr | Arg 1835 | Glu | Trp | Val | Leu Asp 1840 |
| Ser | Val | Ala | Leu | Tyr 1845 | Gln | Cys | Gln | Glu | Leu 1850 | Asp | Thr | | | |

GENETIC MARKERS FOR BREAST, OVARIAN, AND PROSTATIC CANCER

The research carried out in the subject application was supported in part by grants from the National Institutes of Health. The government may have rights in any patent issuing on this application.

CROSS-REFERENCE TO RELATED APPLICATION

This application is a continuing application of U.S. patent application Ser. No. 08/326,983 filed Oct. 20, 1994, now abandoned, which is a continuing application of U.S. patent application Ser. No. 08/232,535 filed Apr. 18, 1994, now abandoned, which is a continuing application of U.S. patent application Ser. No. 08/163,959, filed Dec. 8, 1993, now abandoned.

INTRODUCTION

1. Field of the Invention

The field of the invention is genetic markers for inheritable breast cancer susceptibility.

2. Background

The largest proportion of inherited breast cancer described so far has been attributed to a genetic locus, the BRCA1 locus, on chromosome 17q21 (Hall et al. (1990) Science 250: 1684–1689; Narod et al. (1991) Lancet 338: 82–83; Easton et al. (1993) Am J Hum Genet 52: 678–701). Background material on the genetic markers for breast cancer screening is found in the Jan 29, 1993 issue of Science, vol 259, especially pages 622–625; see also King et al., (1993) J Amer Med Assoc 269: 1975–198. Other relevant research papers include King (1992) Nature Genet 2: 125–126; Merette et al. (1992) Amer J Human Genet 50: 515–519; NIH/CEPH Collaborative Mapping Group (1992) Science 258: 67–86.

Risks of breast cancer to women inheriting the locus are extremely high, exceeding 50% before age 50 and reaching 80% by age 65 (Newman et al. (1988) Proc Natl Acad Sci USA 85: 3044–3048; Hall et al. 1992 Amer J Human Genet 50: 1235–1242; Easton et al. (1993) supra. Epidemiological evidence for inherited susceptibility to ovarian cancer is even stronger (Cramer et at. (1983) J Natl Cancer Inst 71: 711–716; Schildkraut & Thompson (1988) Amer J Epidemiol 128: 456–466; Schildkraut et al. (1989) Amer J Hum Genet 45: 521–529). According to one study, more than 90% of families with multiple relatives with breast and ovarian cancer trace disease susceptibility to chromosome 17q21 (Easton et al. 1993 supra).

The link between increasing risk of breast and ovarian cancer and inherited susceptibility to these diseases lies in the application of genetics to diagnosis and prevention. Creating molecular tools for earlier diagnosis and developing ways to reverse the first steps of tumorigenesis may be the most effective means of breast and ovarian cancer control.

Our laboratory previously mapped the heritable breast cancer susceptibility gene locus (BRCA1 locus) to a 50 cM region of chromosome 17q (Hall et al. 1990, supra). More recently, we developed new polymorphisms at ERBB2 (Hall and King (1991) Nucl Acids Res 19: 2515), THRA1 (Bowcock et al. (1993) Amer J Human Genet 52: 718–722), EDH17B (Friedman et at. (1993) Hum Molec Genet 2: 821), and multiple anonymous loci (Anderson et al. (1993) Genomics 17: 616–623), ultimately developing a high density map of 17q12–q21 (Anderson et at. (1993 supra); see also, Simard et al. (1993) Human Molec Genet 2: 1193–1199). We also added families to the genetic study; there are now 100 families for whom transformed lymphocyte lines have been established and all informative relatives genotyped. We used our new markers and the many chromosome 17q polymorphisms developed in the past three years to test linkage in our families, refining the region first to 8 cM (Hall et al. (1992) supra, then to 4 cM (Bowcock et at. (1993 supra), then to 1 Mb based on polymorphisms from our high density map (Anderson et al. (1993supra); see also Flejter et al., (1993) Genomics 17: 624–631). We disclose here a number of mutations in BRCA1 which correlate with disease.

3. Relevant Literature

The predicted amino acid sequence for a BRCA1 cDNA and familial studies of this gene were described by Miki et al. (1994) Science 266, 66–71 and Futreal et al. (1994) Science 266, 120–122. A study of Canadian cancer families is described in Simard et al. (1994) Nature Genetics 8, 392–398. A collaborative survey of BRCA1 mutations is described in Shattuck-Eidens et al. (1995) JAMA 273, 535–541.

SUMMARY OF THE INVENTION

The invention discloses methods and compositions useful in the diagnosis and treatment of breast and ovarian cancer associated with mutations and/or rare alleles of BRCA1, a breast cancer susceptibility gene. Specific genetic probes diagnostic of inheritable breast cancer susceptibility and methods of use are provided. Labelled nucleic acid probes comprising sequences complementary to specified BRCA1 alleles are hybridized to clinical nucleic acid samples. Linkage analysis and inheritance patterns of the disclosed markers are used to diagnose genetic susceptibility. In addition, BRCA1 mutations and/or rare alleles are directly identified by hybridization, polymorphism and or sequence analysis. In another embodiment, labeled binding agents, such as antibodies, specific for peptides encoded by the subject nucleic acids are used to identify expression products of diagnostic mutations or alleles in patient derived fluid or tissue samples. For therapeutic intervention, the invention provides compositions which can functionally interfere with the transcription or translation products of the breast and ovarian cancer susceptibility associated mutations and/or rare alleles within BRCA1. Such products include anti-sense nucleic acids, competitive peptides encoded by the subject nucleic acids, and high affinity binding agents such as antibodies, specific for e.g. translation products of the disclosed BRCA1 mutations and alleles.

DESCRIPTION OF SPECIFIC EMBODIMENTS

We disclose here methods and compositions for determining the presence or absence of BRCA1 mutations and rare alleles or translation products thereof which are useful in the diagnosis of breast and ovarian cancer susceptibility. Tumorigenic BRCA1 alleles include BRCA1 allele #5803 (SEQUENCE ID NO: 1), 9601 (SEQUENCE ID NO: 2), 9815 (SEQUENCE ID NO: 3), 8403 (SEQUENCE ID NO: 4), 8203 (SEQUENCE ID NO: 5), 388 (SEQUENCE ID NO: 6), 6401 (SEQUENCE ID NO: 7), 4406 (SEQUENCE ID NO: 8), 10201 (SEQUENCE ID NO: 9), 7408 (SEQUENCE ID NO: 10), 582 (SEQUENCE ID NO: 11) or 77 (SEQUENCE ID NO: 12). These nucleic acids or fragments capable of specifically hybridizing with the corresponding allele in the presence of other BRCA1 alleles under stringent conditions find broad diagnostic and therapeutic application. Gene products of the disclosed mutant and/or rare BRCA1 alleles also find a broad range of therapeutic and diagnostic applications. For example, mutant and/or rare allelic BRCA1 peptides are used to generate specific binding compounds. Binding reagents are used diagnostically to distinguish non-tumorigenic wild-type and tumorigenic BRCA1 translation products.

The subject nucleic acids (including fragments thereof) may be single or double stranded and are isolated, partially purified, and/or recombinant. An "isolated" nucleic acid is present as other than a naturally occurring chromosome or transcript in its natural state and isolated from (not joined in sequence to) at least one nucleotide with which it is normally associated on a natural chromosome; a partially pure nucleic acid constitutes at least about 10%, preferably at least about 30%, and more preferably at least about 90% by weight of total nucleic acid present in a given fraction; and a recombinant nucleic acid is joined in sequence to at least one nucleotide with which it is not normally associated on a natural chromosome.

Fragments of the disclosed alleles are sufficiently long for use as specific hybridization probes for detecting endogenous alleles, and particularly to distinguish the disclosed critical rare or mutant alleles which correlate with cancer susceptibility from other BRCA1 alleles, including alleles encoding the BRCA1 translation product displayed in Miki et al (1994) supra, under stringent conditions. Preferred fragments are capable of hybridizing to the corresponding mutant allele under stringency conditions characterized by a hybridization buffer comprising 0% formamide in 0.9M saline/0.09M sodium citrate (SSC) buffer at a temperature of 37° C. and remaining bound when subject to washing at 42° C. with the SSC buffer at 37° C. More preferred fragments will hybridize in a hybridization buffer comprising 20% formamide in 0.9M saline/0.09M sodium citrate (SSC) buffer at a temperature of 42° C. and remaining bound when subject to washing at 42° C. with 2 X SSC buffer at 42° C. In any event, the fragments are necessarily of length sufficient to be unique to the corresponding allele; i.e. has a nucleotide sequence at least long enough to define a novel oligonucleotide, usually at least about 14, 16, 18, 20, 22, or 24 bp in length, though such fragment may be joined in sequence to other nucleotides which may be nucleotides which naturally flank the fragment.

In many applications, the nucleic acids are labelled with directly or indirectly detectable signals or means for amplifying a detectable signal. Examples include radiolabels, luminescent (e.g. fluorescent) tags, components of amplified tags such antigen-labelled antibody, biotin-avidin combinations etc. The nucleic acids can be subject to purification, synthesis, modification, sequencing, recombination, incorporation into a variety of vectors, expression, transfection, administration or methods of use disclosed in standard manuals such as *Molecular Cloning, A Laboratory Manual* (2nd Ed., Sambrook, Fritsch and Maniatis, Cold Spring Harbor), *Current Protocols in Molecular Biology* (Eds. Ausubel, Brent, Kingston, More, Feidman, Smith and Stuhl, Greene Publ. Assoc., Wiley-Interscience, NY, N.Y., 1992) or that are otherwise known in the art.

The subject nucleic acids are used in a wide variety of nucleic acid-based diagnostic method that are known to those in the art. Exemplary methods include their use as allele-specific oligonucleotide probes (ASOs), in ligase mediated methods for detecting mutations, as primers in PCR-based methods, direct sequencing methods wherein the clinical BRCA1 nucleic acid sequence is compared with the disclosed mutations and rare alleles, etc. The subject nucleic acids are capable of detecting the presence of a critical mutant or rare BRCA1 allele in a sample and distinguishing the mutant or rare allele from other BRCA1 alleles. For example, where the subject nucleic acids are used as PCR primers or hybridization probes the subject primer or probe comprises an oligonucleotide complementary to a strand of the mutant or rare allele of length sufficient to selectively hybridize with the mutant or rare allele. Generally, these primers and probes comprise at least 16 bp to 24 bp complementary to the mutant or rare allele and may be as large as is convenient for the hybridizations conditions.

Where the critical mutation is a deletion of wild-type sequence, useful primers/probes require wild-type sequences flanking (both sides) the deletion with at least 2, usually at least 3, more usually at least 4, most usually at least 5 bases. Where the mutation is an insertion or substitution which exceeds about 20 bp, it is generally not necessary to include wild-type sequence in the probes/primers. For insertions or substitutions of fewer than 5 bp, preferred nucleic acid portions comprise and flank the substitution/insertion with at least 2, preferably at least 3, more preferably at least 4, most preferably at least 5 bases. For substitutions or insertions from about 5 to about 20 bp, it is usually necessary to include both the entire insertion/substitution and at least 2, usually at least 3, more usually at least 4, most usually at least 5 basis of wild-type sequence of at least one flank of the substitution/insertion.

In addition to their use as diagnostic genetic probes and primers, BRCA1 nucleic acids are used to effect a variety of gene-based therapies. See, e.g. Zhu et al. (1993) Science 261, 209–211; Gutierrez et al. (1992) Lancet 339, 715–721; Nabel et al. (1993), Proc. Nat'l. Acad Sci USA 90: 11307–11311. For example, therapeutic nucleic acids are used to modulate cellular expression or intracellular concentration or availability of a tumorigenic BRCA1 translation product by introducing into cells complements of the disclosed nucleic acids. These nucleic acids are typically antisense: single-stranded sequences comprising complements of the disclosed relevant BRCA1 mutant. Antisense modulation of the expression of a given mutant may employ antisense nucleic acids operably linked to gene regulatory sequences. Cell are transfected with a vector comprising such a sequence with a promoter sequence oriented such that transcription of the gene yields an antisense transcript capable of binding to the endogenous tumorigenic BRCA1 allele or transcript. Transcription of the antisense nucleic acid may be constitutive or inducible and the vector may provide for stable extrachromosomal maintenance or integration. Alternatively, single-stranded antisense nucleic acids that bind to BRCA1 genomic DNA or mRNA may be administered to the target cell, in or temporarily isolated from a host, at a concentration that results in a substantial reduction in expression of the targeted translation product.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et al., *Trends in Biotech* 11, 205–210 (1993). In some situations it is desirable to provide the nucleic acid source with an agent which targets the target cells, such as an antibody specific for a surface membrane protein on the target cell, a ligand for a receptor on the target cell, etc.

Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the decoy concentration in the lumen will generally be in the range of about 0.1 µM to 20 µM. For other techniques, the application rate is determined empirically, using conventional techniques to determine desired ranges. Usually, application of the subject therapeutics will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Systemic administration of the nucleic acid using lipofection, liposomes with tissue targeting (e.g. antibody) may also be employed.

The invention also provides isolated translation products of the disclosed BRCA1 allele which distinguish the wild type BRCA1 gene product. For example, for alleles which encode truncated tumorigenic translation product, the C-terminus is used to differentiate wild-type BRCA1. Accordingly, the invention provides the translation product of BRCA1 allele #5803 (SEQUENCE ID NO: 13), 9601 (SEQUENCE ID NO: 14), 9815 (SEQUENCE ID NO: 15), 8203 (SEQUENCE ID NO: 17), 388 (SEQUENCE ID NO: 18), 6401 (SEQUENCE ID NO: 19), 4406 (SEQUENCE ID NO: 20), 10201 (SEQUENCE ID NO: 21), 7408 (SEQUENCE ID NO: 22), 582 (SEQUENCE ID NO: 23) or 77 (SEQUENCE ID NO: 24), or a C-terminus fragment thereof; and that of #8403 (SEQUENCE ID NO: 16), or a fragment thereof comprising Gly at position 61.

The subject mutant and/or rare allelic BRCA1 translation products comprise an amino acid sequence which provides a target for distinguishing the product from that of other BRCA1 alleles. Preferred fragments are capable of eliciting the production of a peptide-specific antibody, in vivo or in vitro, capable of distinguishing a protein comprising the immunogenic peptide from a wild-type BRCA1 translation product. The fragments are necessarily unique to the disclosed allele translation product in that it is not found in any previously known protein and has a length at least long enough to define a novel peptide, from about 5 to about 25 residues, preferably from 6 to 10 residues in length, depending on the particular amino acid sequence.

The subject translation products (including fragments) are either isolated, i.e. unaccompanied by at least some of the material with which they are associated in their natural state); partially purified, i.e. constituting at least about 1%, preferably at least about 10%, and more preferably at least about 50% by weight of the total translation product in a given sample; or pure, i.e. at least about 60%, preferably at least 80%, and more preferably at least about 90% by weight of total translation product. Included in the subject translation product weight are any atoms, molecules, groups, etc. covalently coupled to the subject translation products, such as detectable labels, glycosylations, phosphorylations, etc. The subject translation products may be isolated, purified, modified or joined to other compounds in a variety of ways known to those skilled in the art depending on what other components are present in the sample and to what, if anything, the translation product is covalently linked.

Binding agents specific for the disclosed tumorigenic BRCA1 genes and gene products find particular use in cancer diagnosis. The selected method of diagnosis will depend on the nature of the tumorigenic BRCA1 mutants/ rare allele and its transcription or translation product(s). For example, soluble secreted translation products of the disclosed alleles may be detected in a variety of physiologic fluids using a binding agent with a detectable label such as a radiolabel, fluorester etc. Detection of membrane bound or intracellular products generally requires preliminary isolation of cells (e.g. blood cells) or tissue (e.g. breast biopsy tissue). A wide variety of specific binding assays, e.g. ELISA, may be used BRCA1 gene product-specific binding agents are produced in a variety of ways using the compositions disclosed herein. For example, structural x-ray crystallographic and/or NMR data of the mutant and/or rare allelic BRCA1 translation products are used to rationally design binding molecules of determined structure or complementarity. Also, the disclosed mutant and/or rare allelic BRCA1 translation products are used as immunogens to generate specific polyclonal or monoclonal antibodies. See, Harlow and Lane (1988) *Antibodies, A Laboratory Manual*, Cold Spring Harbor Laboratory, for general methods. Specific antibodies are readily modified to a monovalent form, such as Fab, Fab', or Fv.

Other mutant and/or rare allelic BRCA1 gene-product specific agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful binding agents are identified with assays employing a compound comprising mutant and/or rare allelic BRCA1 peptides or encoding nucleic acids. A wide variety of in vitro, cell-free binding assays, especially assays for specific binding to immobilized compounds comprising the subject nucleic acid or translation product find convenient use. See, e.g. Fodor et al (1991) Science 251, 767, for the light directed parallel synthesis method. Such assays are amenable to scale-up, high throughput usage suitable for volume drug screening.

Useful agents are typically those that bind the targeted mutant and/or rare allelic BRCA1 gene product with high affinity and specificity and distinguish the tumorigenic BRCA1 mutants/rare alleles from the wild-type BRCA1 gene product. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, sterols, isoprenoids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means to enhance efficacy, stability, pharmaceutical compatibility, and the like. In addition, known pharmacological agents may be subject to directed or random chemical modifications, such as acylation, alkylation, esterification, amidification, etc., to produce structural analogs.

Therapeutic applications typically involve binding to and functional disruption of a tumorigenic BRCA1 gene product by an administered high affinity binding agent. For therapeutic uses, the compositions and agents disclosed herein may be administered by any convenient way. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration will generally be in the range of about 50 to 500 µg/ml in the dose administered. Other additives may be included, such as stabilizers, bactericides, etc. These additives will be present in conventional amounts.

The following examples are offered by way of illustration and not by way of limitation.

EXAMPLES

Example 1. Positional Cloning

Contig Construction

YACs.

Primers flanking polymorphic repeats in the 4 Mb region of linkage were used to amplify pools from the CEPH, Washington University, and CEPH megaYAC libraries available. 39 YACs were selected. Of these, 23 were tested for chimerism by FISH and 12 found to be chimeric. YACs were aligned to each other by attempting to amplify each YAC with primer pairs from known sequence tagged sites (STSes). More STSes were defined by sequencing the ends of YACs, and these new STSes used for further alignment and YAC identification.

Cosmids.

A gridded cosmid library of chromosome 17 was prepared. Alu-Alu PCR products of YACs were hybridized to the cosmid grids and positively hybridizing cosmids used for subsequent studies. Contigs were constructed in two ways. Cosmids with the same restriction patterns were aligned; and, the unique sequences flanking polymorphic markers and our sequenced cDNAs were used as STSes.

Physical Mapping by Pulsed Field Gel Electrophoresis.

Physical distances were estimated by pulsed field gel electrophoresis, using DNA from lymphocyte cell lines of BRCA1-linked patients and of controls. DNA samples were digested with NotI, MluI, RsrII, NruI, SacII, and EclXI. Filters were probed with single-copy sequences isolated from cosmids and later with eDNA clones. Multiple unrelated linked patients and controls were screened to detect large insertions or deletions associated with BRCA1. Results of PFGE were used to define the region first used to screen eDNA libraries as ~1 Mb and the current linked region as ≦500 kb.

Screening cDNA Libraries.

We began library screening when the linked region defined by meiotic recombination was ~1 Mb. The first question was what library would optimize the length of cDNA clones, representation of both 5' and 3' ends of genes, and the chances that BRCA1 would be expressed. We chose to use a random primed cDNA library cloned into 1gt10 from cultured (not transformed) fibroblasts from a human female. This library was selected because it had inserts averaging 1.8 kb, with 80% of inserts between 1 and 4 kb, was contructed from cultured fibroblasts known to be "leaky" in gene expression, and was known to include 5' ends of genes. We simultaneously screened three other libraries (from ovary, fetal brain, and mouse mammary epithelium). With one exception (described below), all transcripts from these libraries cross-hybridized to transcripts from the fibroblast library.

The fibroblast library was screened with YAC DNA isolated by PFGE. Pure YAC DNA (100 nanograms) was random primed with both aP32-dATP (6000 mCi/mmole) and $^{32}$P-dCTP (3000 mCi/mmole), and used immediately after labelling. Filters from the library were prehybridized with human placental DNA for 24–48 hours. Labelled YAC DNA was hybridized to the filters for 48 hours at 65° C. Approximately 250 transcripts were selected by screening with 7 YACs and then ross-hybridized. We also used pools of cosmids from the linked region to screen the fibroblast library. We selected 122 transcripts and cross-hybridized them to clones previously detected by the YACs.

Example 2. Cloning BRCA1 and its Characterization

A. Screening for Mutations in Candidate Genes.

We initially identified 24 genes in the 1 Mb BRCA1 region defined by meiotic recombination, respective locations on the YAC contig, sizes of representative cDNA clones, numbers of replicates in the library, sizes of transcripts, homologies to known genes, and variants detected. Candidate gene were characterized in the following ways:

(1) Cross-Hybridizing Clones.

cDNA clones isolated from the library are hybridized against each other. Cross-hybridizing clones are considered "siblings" of the clone used as a probe and represent the same gene.

(2) Mapping Back.

At least one clone from each sibship is mapped back to total human genomic DNA, to cosmids, to YACs, and to somatic cell hybrid lines, some of which contain deletions of 17q and one of which has chromosome 17 as its only human chromosome.

(3) Subcloning and Sequencing.

One of the longest clones from each sibship is subcloned into M13 and sequenced manually by standard methods, constructing new primers at the end of each fragment to continue sequencing until the end of the clone is reached.

(4) Extending Sequences with Sibs.

In order to find clones that contain more of the gene, the last sequencing primer for the clone and primers made from gt10 are used to amplify sibs of the first clone. Sibs that amplify the longest fragments are selected, subcloned, and sequenced. This process is continued until we reach the size of the transcript defined by Northern blot and/or until the 3' sequence is a polyA tail and the 5' sequence has features of the beginning of the coding region.

(5) Southerns.

To identify insertion or deletion mutations, genomic DNA from 20 unrelated patients from families with breast cancer linked to 17q (i.e. "linked patients") and controls are digested with BamHI/TaqI and independently with HindIII/HinfI. Each cDNA clone is used to screen Southern blots. Variants have been detected in two genes. Both of these variants are RFLPs, occuring in equal frequency in linked patients and in controls.

(6) Northerns.

To identify splice mutations and/or length mutations, we prepared total RNA and polyA+ RNA from germline DNA (from lymphoblast lines) of 20 unrelated linked patients, from ovarian and breast tissues, from fibroblasts, from a HeLa cell line, and from breast cancer cell lines. Northern blots are screened with each gene.

(7) Detection of Small Mutations.

To screen for germline point mutations in patients without encountering introns, we prepared cDNA from poly-A+ mRNA from lymphoblast cell lines of 20 unrelated linked patients and from controls. cDNA has also been made from 65 malignant ovarian cancers from patients not selected for family history. Primers are constructed every ~200 basepairs along the sequence and used to amplify these cDNAs. Genomic DNA has also been prepared from cell lines from all family members (linked and unlinked), from malignant and normal cells from paraffin blocks from their breast and ovarian surgeries, and from malignant and normal cells from 29 breast tumors not selected for family history. For sequences without introns, cDNA and gDNA lengths are equal, and the gDNA samples are amplified as well.

Two mutation detection methods are used to screen each sequence. Amplified products are screened for SSCPs using modifications that enable electrophoresis to be done with only one set of running conditions (Keen et at. (1991) Trends Genet 7: 5; Soto and Sukumar (1992) PCR Meth Appl 2: 96–98). In order to screen longer segments of DNA (100–1500 bp) and to detect variants missed by SSCP, sequences are also screened for point mutations by CCM (Cotton (1993) Mutation Res 285: 125–144) using essentially the protocol of Grompe et al. (1989) Proc Natl Acad Sci USA 86: 5888–5892. An endonuclease developed for mismatch detection reduces the toxicity of the method (Youil et al. (1993) Amer J Hum Genet 53 (supplement): abstract 1257).

(8) Polymorphism or Mutation.

Variants are screened in cases and controls to distinguish polymorphisms from a critical mutation. Linkage of breast cancer to each variant is tested in all informative families.

Example 3. Characterize BRCA1 Mutations in Germline DNA and Breast Cancer Patient Tumors A. BRCA1 Mutations in Chromosome 17q-Linked Families.

Our series of families includes 20 large extended kindreds in which breast and ovarian cancer (and in one family prostatic cancer) are linked to 17q21, with individual lod scores >1.5. Since linked patients in these families carry mutations in BRCA1, we have identified their mutations first.

TABLE 1 summarizes critical BRCA1 mutations and rare alleles:

| Family | Exon | U14680 nt | Mutation | Amino Acid change | Predicted effect |
| --- | --- | --- | --- | --- | --- |
| 5803 SEQ ID NO: 1 | 3 | 200–253 | exon 3 deleted (54 bp) | 27 Stop | protein truncation SEQ ID NO: 13 |
| 9601 SEQ ID NO: 2 | 3 | 230 | deletion AA | 39 Stop | protein truncation SEQ ID NO: 14 |
| 9815 SEQ ID NO: 3 | Intron 5 | splice donor, bp +1 | substitution G to A ->22 bp deletion (base pairs 310–331) in RNA | 64 Stop | protein truncation SEQ ID NO: 15 |
| 8403 SEQ ID NO: 4 | 5 | 300 | substitution T to G | Cys 61 Gly | lose zinc-binding motif SEQ ID NO: 16 |
| 8203 SEQ ID NO: 5 | Intron 5 | splice acceptor, bp −11 | substitution T to G ->59 bp insertion of intron into RNA (at base pair 331) | 81 Stop | protein truncation SEQ ID NO: 17 |
| 388 SEQ ID NO: 6 | 11 | 1048 | deletion A | 313 Stop | protein truncation SEQ ID NO: 18 |
| 6401 SEQ ID NO: 7 | 11 | 2415 | deletion AG | Ser 766 Stop | protein truncation SEQ ID NO: 19 |
| 4406 SEQ ID NO: 8 | 11 | 2800 | deletion AA | 901 Stop | protein truncation SEQ ID NO: 20 |
| 10201 SEQ ID NO: 9 | 11 | 2863 | deletion TC | Ser 915 Stop | protein truncation SEQ ID NO: 21 |
| 7408 SEQ ID NO: 10 | 11 | 3726 | substitution C to T | Arg 1203 Stop | protein truncation SEQ ID NO: 22 |
| 582 SEQ ID NO: 11 | 11 | 4184 | deletion TCAA | 1364 Stop | protein truncation SEQ ID NO: 23 |
| 77 SEQ ID NO: 12 | 24 | 5677 | Insertion A | Tyr 1853 Stop | protein truncation SEQ ID NO: 24 |

B. Germline BRCA Mutations Among Breast Cancer Patients in the General Population.

From each breast cancer patient, not selected for family history, a 30 ml sample of whole blood is drawn into acid citrate dextrose. DNA from the blood is extracted and stored at −70° C. in 3 aliquots. Germline mutations in BRCA1 are identified using the approaches described above and by directly sequencing new mutations. Paraffin-embedded tumor specimens from the same patients are screened for alterations of p53, HER2, PRAD 1, and ER. Germline BRCA1 mutations are tested in the tumor blocks.

A preliminary estimate of risk associated with different BRCA1 mutations is obtained from relatives of patients with germline alterations. For each patient with a germline BRCA1 mutation, each surviving sister and mother (and for older patients, brothers as well), DNA is extracted from a blood sample and tested for the presence of the proband's BRCA1 mutation. To ascertain men at risk for prostatic cancer, brothers of breast cancer patients diagnosed after age 55 are also interviewed and sampled. Paraffin blocks from deceased relatives who had cancer are also screened. The frequency of breast, ovarian, or prostatic cancer among relatives carrying BRCA1 mutations is a first estimate of risk of these cancers associated with different mutations.

C. Somatic Alterations of BRCA1 in Breast Tumors.

Malignant cells are dissected from normal cells from paraffin blocks. By identifying BRCA1 mutations in these series, we estimate the frequency of somatic BRCA1 alterations, determine BRCA1 mutations characteristic of any particular stage of tumor development, and evaluate their association with prognosis.

D. Characterizing Mutant and Rare Alleles of BRCA1.

Mutant or rare BRCA1 allele function and pattern of expression during development are characterized using transformed cells expressing the allele and knockout or transgenic mice. For example, phenotypic changes in the animal or cell line, such as growth rate and anchorage independence are determined. In addition, several methods are used to study loss-of-function mutations, including replacing normal genes with their mutant alleles (BRCA1-/BRCA1-) by homologous recombination in embryonic stem (ES) cells and replacing mutant alleles with their normal counterparts in differentiated cultured cells (Capecchi (1989) Science 244: 1288–1292; Weissman et al. (1987) Science 236: 175–180; Wang et al. (1993) Oncogene 8: 279–288). Breast carcinoma cell lines are screened for mutation at the BRCA1 locus and a mutant BRCA1 line is selected. Normal and mutant cDNAs of BRCA1 are subcloned into an expression vector carrying genes which confer resistance to ampicillin and geneticin (Baker et al. (1990)Nature 249: 912–915). Subclones are transfected into mutant BRCA1 breast cancer cells Geneticin-resistant colonies are isolated and examined for any change in tumorigenic phenotype, such as colony formation in soft agar, increased growth rate, and/or tumor formation in athymic nude mice. In vivo functional demonstrations involve introducing the normal BCRA1 gene into a breast carcinoma cell line mutant at BRCA1 and injecting these BRCA1+ cells into nude mice. Changes observed in tumorigenic growth compared to nude mice injected with BRCA1 mutant breast carcinoma cells are readily observed. For example, correcting the mutant gene decreases the ability of the breast carcinoma cells to form tumors in nude mice (Weissman et al. (1987) Science 236: 175–8, Wang et al. (1993) Oncogene 8: 279–88).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising BRCA1 allele #5803 (SEQUENCE ID NO: 1), 9601 (SEQUENCE ID NO: 2), 9815 (SEQUENCE ID NO: 3), 8403 (SEQUENCE ID NO: 4), 8203 (SEQUENCE ID NO: 5), 388 (SEQUENCE ID NO: 6), 6401 (SEQUENCE ID NO: 7), 4406 (SEQUENCE ID NO: 8), 10201 (SEQUENCE ID NO: 9), 7408 (SEQUENCE ID NO: 10), 582 (SEQUENCE ID NO: 11) or 77 (SEQUENCE ID NO: 12), or a fragment thereof, wherein said fragment is capable of specifically hybridizing with said allele in the presence of wild-type BRCA1.

2. An isolated nucleic acid according to claim 1, comprising BRCA1 allele #5803 (SEQUENCE ID NO: 1), or a fragment thereof, wherein said fragment is capable of specifically hybridizing with said allele in the presence of wild-type BRCA1.

3. An isolated nucleic acid according to claim 1, comprising BRCA1 allele #9601 (SEQUENCE ID NO: 2), or a fragment thereof, wherein said fragment is capable of specifically hybridizing with said allele in the presence of wild-type BRCA1.

4. An isolated nucleic acid according to claim 1, comprising BRCA1 allele #9815 (SEQUENCE ID NO: 3), or a fragment thereof, wherein said fragment is capable of specifically hybridizing with said allele in the presence of wild-type BRCA1.

5. An isolated nucleic acid according to claim 1, comprising BRCA1 allele #8403 (SEQUENCE ID NO: 4), or a fragment thereof, wherein said fragment is capable of specifically hybridizing with said allele in the presence of wild-type BRCA1.

6. An isolated nucleic acid according to claim 1, comprising BRCA1 allele #8203 (SEQUENCE ID NO: 5), or a fragment thereof, wherein said fragment is capable of specifically hybridizing with said allele in the presence of wild-type BRCA1.

7. An isolated nucleic acid according to claim 1, comprising BRCA1 allele #388 (SEQUENCE ID NO: 6), or a fragment thereof, wherein said fragment is capable of specifically hybridizing with said allele in the presence of wild-type BRCA1.

8. An isolated nucleic acid according to claim 1, comprising BRCA1 allele #6401 (SEQUENCE ID NO: 7), or a fragment thereof, wherein said fragment is capable of specifically hybridizing with said allele in the presence of wild-type BRCA1.

9. An isolated nucleic acid according to claim 1, comprising BRCA1 allele #4406 (SEQUENCE ID NO: 8), or a fragment thereof, wherein said fragment is capable of specifically hybridizing with said allele in the presence of wild-type BRCA1.

10. An isolated nucleic acid according to claim 1, comprising BRCA1 allele #10201 (SEQUENCE ID NO: 9), or a fragment thereof, wherein said fragment is capable of specifically hybridizing with said allele in the presence of wild-type BRCA1.

11. An isolated nucleic acid according to claim 1, comprising BRCA1 allele #7408 (SEQUENCE ID NO: 10), or a fragment thereof, wherein said fragment is capable of specifically hybridizing with said allele in the presence of wild-type BRCA1.

12. An isolated nucleic acid according to claim 1, comprising BRCA1 allele #582 (SEQUENCE ID NO: 11), or a fragment thereof, wherein said fragment is capable of specifically hybridizing with said allele in the presence of wild-type BRCA1.

13. An isolated nucleic acid according to claim 1, comprising BRCA1 allele #77 (SEQUENCE ID NO: 12), or a fragment thereof, wherein said fragment is capable of specifically hybridizing with said allele in the presence of wild-type BRCA1.

14. A method of screening a patient for a breast, ovarian or prostatic cancer susceptibility, said method comprising the steps of:

contacting a sample comprising a first nucleic acid with a second nucleic acid under conditions whereby said second nucleic acid is capable of specifically hybridizing with said first nucleic acid in the presence of wild-type BRCA1, said first nucleic acid comprising a sample BRCA1 allele, or a sample BRCA1 allele fragment thereof, wherein said sample BRCA1 allele fragment is capable of specifically hybridizing with its corresponding sample BRCA1 allele in the presence of wild-type BRCA1, and said second nucleic acid comprising an isolated nucleic acid comprising mutant BRCA1 allele #5803 (SEQUENCE ID NO: 1), 9601 (SEQUENCE ID NO: 2), 9815 (SEQUENCE ID NO: 3), 8403 (SEQUENCE ID NO: 4), 8203 (SEQUENCE ID NO: 5), 388 (SEQUENCE ID NO: 6), 6401 (SEQUENCE ID NO: 7), 4406 (SEQUENCE ID NO: 8), 10201 (SEQUENCE ID NO: 9), 7408 (SEQUENCE ID NO: 10), 582 (SEQUENCE ID NO: 11) or 77 (SEQUENCE ID NO: 12), or a mutant BRCA1 allele fragment thereof, wherein said mutant BRCA1 allele fragment is capable of specifically hybridizing with its corresponding mutant BRCA1 allele in the presence of wild-type BRCA1, detecting the presence or absence of specific hybridization of said second nucleic acid with said first nucleic acid;

wherein the presence of specific hybridization of said second nucleic acid with said first nucleic acid is indicative of breast, ovarian or prostatic cancer susceptibility for a patient having said sample BRCA1 allele.

15. A method according to claim 14, wherein said isolated nucleic acid comprises mutant BRCA1 allele #5803 (SEQUENCE ID NO: 1), or a fragment thereof, wherein stud fragment is capable of specifically hybridizing with said allele in the presence of wild-type BRCA1.

16. A method according to claim 14, wherein said isolated nucleic acid comprises mutant BRCA1 allele #9601 (SEQUENCE ID NO: 2), or a fragment thereof, wherein said fragment is capable of specifically hybridizing with said allele in the presence of wild-type BRCA1.

17. A method according to claim 14, wherein said isolated nucleic acid comprises mutant BRCA1 allele #9815 (SEQUENCE ID NO: 3), or a fragment thereof, wherein stud fragment is capable of specifically hybridizing with said allele in the presence of wild-type BRCA1.

18. A method according to claim 14, wherein said isolated nucleic acid comprises mutant BRCA1 allele #8403 (SEQUENCE ID NO: 4), or a fragment thereof, wherein said fragment is capable of specifically hybridizing with said allele in the presence of wild-type BRCA1.

19. A method according to claim 14, wherein said isolated nucleic acid comprises mutant BRCA1 allele #8203 (SEQUENCE ID NO: 5), or a fragment thereof, wherein stud fragment is capable of specifically hybridizing with said allele in the presence of wild-type BRCA1.

20. A method according to claim 14, wherein said isolated nucleic acid comprises mutant BRCA1 allele #388 (SEQUENCE ID NO: 6), or a fragment thereof, wherein said fragment is capable of specifically hybridizing with said allele in the presence of wild-type BRCA1.

21. A method according to claim 14, wherein said isolated nucleic acid comprises mutant BRCA1 allele #6401 (SEQUENCE ID NO: 7), or a fragment thereof, wherein said fragment is capable of specifically hybridizing with said allele in the presence of wild-type BRCA1.

22. A method according to claim 14, wherein said isolated nucleic acid comprises mutant BRCA1 allele #4406 (SEQUENCE ID NO: 8), or a fragment thereof, wherein said fragment is capable of specifically hybridizing with said allele in the presence of wild-type BRCA1.

23. A method according to claim 14, wherein said isolated nucleic acid comprises mutant BRCA1 allele #10201 (SEQUENCE ID NO: 9), or a fragment thereof, wherein said fragment is capable of specifically hybridizing with said allele in the presence of wild-type BRCA1.

24. A method according to claim 14, wherein said isolated nucleic acid comprises mutant BRCA1 allele #7408 (SEQUENCE ID NO: 10), or a fragment thereof, wherein said fragment is capable of specifically hybridizing with said allele in the presence of wild-type BRCA1.

25. A method according to claim 14, wherein said isolated nucleic acid comprises mutant BRCA1 allele #582 (SEQUENCE ID NO: 11), or a fragment thereof, wherein said fragment is capable of specifically hybridizing with said allele in the presence of wild-type BRCA1.

26. A method according to claim 14, wherein said isolated nucleic acid comprises mutant BRCA1 allele #77 (SEQUENCE ID NO: 12), or a fragment thereof, wherein said fragment is capable of specifically hybridizing with said allele in the presence of wild-type BRCA1.

* * * * *